(12) United States Patent
Bensussan et al.

(10) Patent No.: US 8,444,978 B2
(45) Date of Patent: May 21, 2013

(54) ANGIOGENIC AND IMMUNOLOGIC APPLICATIONS OF ANTI-CD160 SPECIFIC COMPOUNDS OBTAINABLE FROM MAB CL1-R2

(75) Inventors: Armand Bensussan, Paris (FR); Laurence Boumsell, Paris (FR); Phillipe Le Bouteiller, Blagnac (FR)

(73) Assignee: INSERM (Institut National de la Santé et de la Recherche Médicale), Paris (FR)

( * ) Notice: Subject to any disclaimer, the term of this patent is extended or adjusted under 35 U.S.C. 154(b) by 0 days.

(21) Appl. No.: 13/175,221

(22) Filed: Jul. 1, 2011

(65) Prior Publication Data

US 2012/0003224 A1 Jan. 5, 2012

Related U.S. Application Data

(62) Division of application No. 11/659,749, filed as application No. PCT/EP2005/009231 on Aug. 9, 2005, now abandoned.

(30) Foreign Application Priority Data

Aug. 9, 2004 (EP) .................................... 04292015

(51) Int. Cl.
*A61K 39/00* (2006.01)
(52) U.S. Cl.
USPC ...................................................... 424/139.1
(58) Field of Classification Search
None
See application file for complete search history.

(56) References Cited

U.S. PATENT DOCUMENTS

| | | | |
|---|---|---|---|
| 6,194,549 B1 | 2/2001 | Anderson et al. | |
| 2005/0032725 A1* | 2/2005 | Rao et al. ...................... | 514/44 |

FOREIGN PATENT DOCUMENTS

| | | |
|---|---|---|
| WO | WO-98/21240 A1 | 5/1998 |
| WO | WO-03/018048 | 3/2003 |

OTHER PUBLICATIONS

Translation of WO03018048, 2012, pp. 1-12.*
International Search Report relating to the corresponding International Patent Application No. PCT/EP2005/009231, dated Jan. 4, 2006.
Agrawal et al., Cutting Edge: MHC Class I Triggering by a Novel Cell Surface Ligand Costimulates Proliferation of Activated Human T Cells, Journal of Immunology 162:1223-1226 (1999).
Anukanth et al., "Cloning of BY55, a Novel Ig Superfamily Member Expressed on NK Cells, CTL, and Intestinal Intraepithelial Lymphocytes," Journal of Immunology 161:2780-2790 (1998).
Barakonyi et al., "Cutting Edge: Engagement of CD160 by its HLA-C Physiological Ligand Triggers a Unique Cytokine Profile Secretion in the Cytotoxic Peripheral Blook NK Cell Subset," Journal of Immunology 173:5349-5354 (2004).
BD Biosciences, "Fluorescein Isothiocyanate (FITC)-Conjugated Mouse Anti-Human Monoclonal Antibody," www.bdbiosciences. com/external_files/pn/doc/tds/human/live/web_enabled/38484X_ 551888.pdf, retrieved on Jan. 3, 2005.
Laso et al., "Alterations in Tumor Necrosis Factor-α, Interferon-γ, and Interleukin-6 Production by Natural Killer Cell-Enriched Peripheral Blood Mononuclear Cells in Chronic Alcoholism: Relationship with Liver Disease and Ethanol Intake," Alcoholism, Clinical and Experimental Research 21:1226-1231 (1997).
Le Bouteiller et al., "Engagement of CD160 Receptor by HLA-C is a Triggering Mechanism Used by Circulating Natural Killer (NK) Cells to Mediate Cytotoxicity," Proceedings of the National Academy of Sciences of the United States of America 99:16963-16968 (2002).
Klimka et al., "Human anti-CD30 recombinant antibodies by guided phage antibody selection using cell panning," Bri J. Cancer, vol. 83: 252-260 (2000).
Miller et al., "Design, Construction, and in Vitro Analyses of Multivalent Antibodies," J. of Immunology, 170: 4854-4861 (2003).
Nikolova et al., "BY55/CD160 Acts as a Co-Receptor in TCR Signal Transduction of a Human Circulating Cytotoxic Effector T Lymphcyte Subset Lacking CD28 Expression," International Immunology 14:445-451 (2002).

* cited by examiner

Primary Examiner — Amy Juedes
(74) Attorney, Agent, or Firm — Marshall, Gerstein & Borun LLP

(57) ABSTRACT

The present invention relates to biological and medical applications of an anti-CD160 monoclonal antibody (CL1-R2 CNCM I-3204) and of the conservative equivalents thereof. It more particularly relates to the applications of these anti-CD160 compounds in the fields of EC angiogenesis, and NK and T cytokine production.

11 Claims, 21 Drawing Sheets

A
FIG. 6A
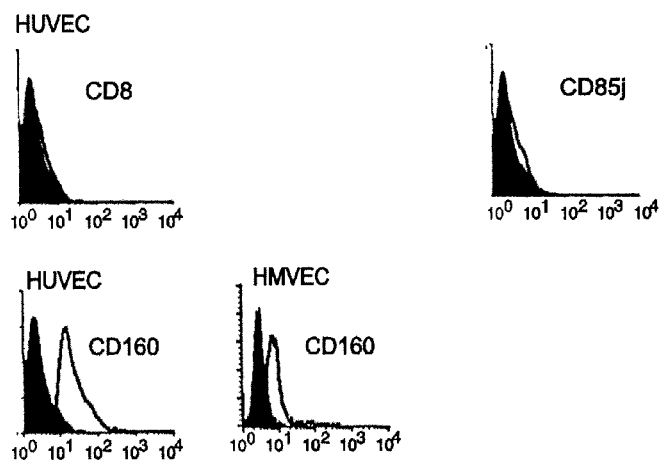
B
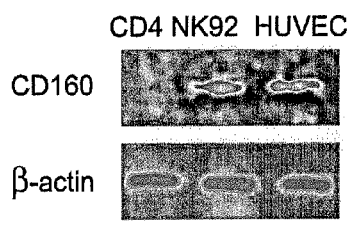
FIG. 6B
C
```
            Leader
CD160 NK92   MLLEPGRGCC ALAILLAIVD IQSGGCINIT SSASQEGTRL NLICTVWHKK    50
CD160 HUVEC  ---------- ---------- ---------- ---------- ----------
             EEAEGFVVFL CKDRSGDCSP ETSLKQLRLK RDPGIDGVGE ISSQLMFTIS   100
             ---------- Y--------- ---------- ---------- ----------
             QVTPLHSGTY QCCARSQKSG IRLQGHFFSI LFTETGNYTV TGLKQRQHLE   150
             ---------- ----G----- ---------- ---------- ----------
                                          GPI anchor
             FSHNEGTLSS GFLQEKVWVM LVTSLVALQAL 181
             ---------- ---------- -----------
```
FIG. 6C

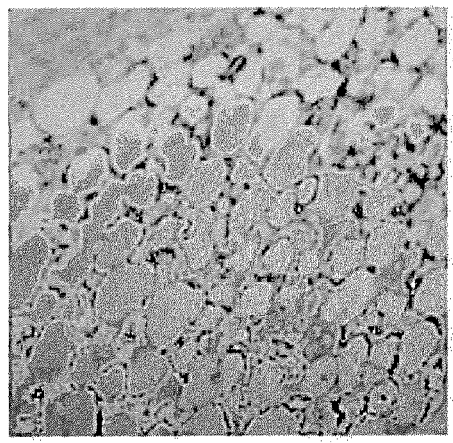 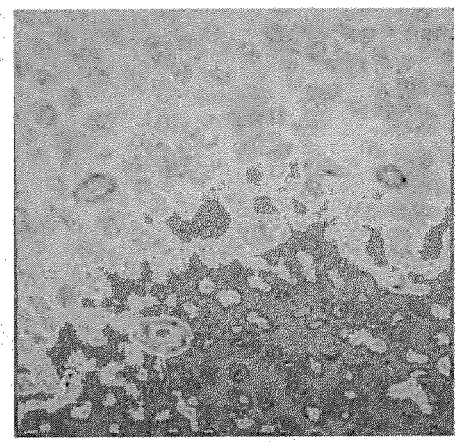
FIG. 10A  FIG. 10B
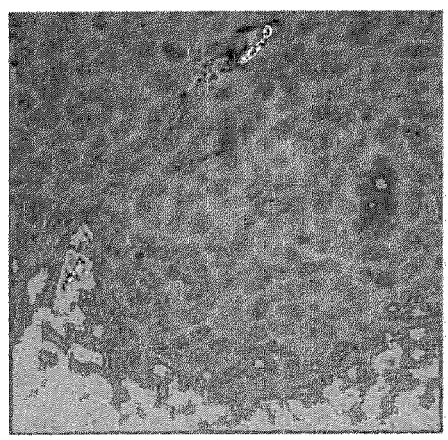 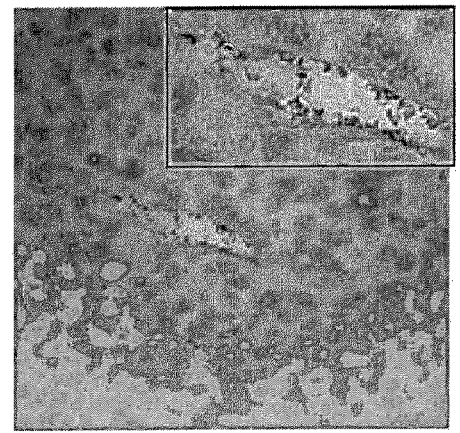
FIG. 10C  FIG. 10D

IL15-CD4+  NK92  PB-CD4+ a b c

```
                    Leader
CD160 NK92    MLLEPGRGCC ALAILLAIVD IQSGGCINIT SSASQEGTRL NLICTVWHKK   50
CD160 HUVEC   ---------- ---------- ---------- ---------- ----------

EEAEGFVVFL CKDRSGDCSP ETSLKQLRLK RDPGIDGVGE ISSQLMFTIS  100
              ---------- Y--------- ---------- ---------- ----------

QVTPLHSGTY QCCARSQKSG IRLQGHFFSI LFTETGNYTV TGLKQRQHLE  150
              ---------- ----G----- ---------- ---------- ----------
                                   GPI anchor
              FSHNEGTLSS GFLQEKVWVM LVTSLVALQAL 181
              ---------- ---------- -----------
```

ANGIOGENIC AND IMMUNOLOGIC APPLICATIONS OF ANTI-CD160 SPECIFIC COMPOUNDS OBTAINABLE FROM MAB CL1-R2

CROSS-REFERENCE TO RELATED APPLICATIONS

This application is a divisional application of U.S. application Ser. No. 11/659,749 filed Apr. 25, 2008 now abandoned, which is a U.S. National Phase Application pursuant to 35 U.S.C. 371 of International Application No. PCT/EP2005/009231 filed Aug. 9, 2005, claiming benefit of priority of European Patent Application No. 04292015.7 filed Aug. 9, 2004. The entire disclosure of each of the foregoing applications is incorporated herein by reference.

FIELD OF THE INVENTION

The present invention relates to an anti-CD160 specific mAb (CL1-R2 accessible under hybridoma deposit number CNCM I-3204), to anti-CD160 specific compounds deriving therefrom, and to the biological and medical applications of such anti-CD160 compounds and mAb.

BACKGROUND OF THE INVENTION

The present invention more particularly relates to means for specifically controlling and regulating:
- the angiogenesis of endothelial cells (EC), and
- the contribution of NK and T cells to the regulation of the immune system.

The different aspects of the invention share the common feature of implementing or requiring an anti-CD160 monoclonal antibody (mAb) of the present invention, namely the mAb referred to by the inventors as CL1-R2 (hybridoma Budapest Treaty deposit CNCM I-3204), or a conservative equivalent thereof.

The present invention indeed demonstrates that the receptor CD160 (previously also referred to as BY55), which is known to be expressed by cytotoxic NK and T subsets ($CD56^{dim}$ $CD16^{bright}$ $CD3^-$ NK; T CD8+; TCRγδ), is involved in both angiogenesis and immune system regulation. CD160 structure has been extensively described in prior art documents, see e.g. WO 98/21240 in the name of the DANA-FARBER CANCER INSTITUTE.

EC and Angiogenesis:

Angiogenesis, the formation of new capillaries from the preexisting blood vessels, is a crucial component of embryonic vascular development and differentiation, wound healing, and organ regeneration. It however also contributes to the progression of pathologies that depends on neovascularization, including tumor growth, diabetes, ischemic ocular diseases, and rheumatoid arthritis (Risau, 1997; Ferrara, 1997). While the most important mediators of angiogenesis, the vascular endothelial cell growth factor (VEGF) family and fibroblast growth factor family are well define, angiogenesis stands as a complex process involving multiple gene products expressed by different cell types all contributing to an integrated sequence of events.

WO 03/018048 in the name of ABTECH et al. relates to the use of two soluble HLA Class I molecules, namely sHLA-G1 and sHLA-B7, to inhibit angiogenesis or to detect angiogenic sites. Supportive to this anti-angiogenic effect is the demonstration that sHLA-G1 inhibits endothelial cells (EC) proliferation and migration. It is also shown that sHLA-G1 and sHLA-B7 may inhibit the progression of a tumor induced by grafting human prostate adenocarcinoma cells in nude mice.

WO 03/018048 also mentions that an anti-CD160 antibody referred to as CL1-R2 inhibits the action exerted by sHLA-G on EC migration. It is therefrom deduced that BY55 could be an endothelial receptor for sHLA-G (cf. WO 03/018048 as published, page 23 lines 3-8).

The skilled person would however notice that WO 03/018048 gives no publicly available source for the mentioned CL1-R2 antibody.

On the other hand, soluble HLA, such as sHLA-G1 and sHLA-B7, are natural ligands for numerous receptors.

Hence, there remains a need in prior art for means that would be sufficiently specific to the angiogenesis signaling pathways to enable the elucidation of the mechanisms they involve. Specificity is also needed to provide medically useful compounds that can exert a specific control on angiogenesis without necessarily disturbing other signaling pathways.

NK and T Cells and the Immune System:

NK cells constitute a subset of lymphocytes that play a role in innate immunity directed against virally-infected or tumor cells. Their effector functions are the killing of target cells and cytokine production. NK cells use a combination of inhibitory and activating receptors expressed at their cell surface to mediate target cell killing and cytokine release upon interaction with specific ligands. Upon specific engagement with these ligands present on target cells, they release cytolytic granules containing perforin and granzyme that contribute to target cell apoptosis. Upon contact with sensitive target cells, they also produce a number of cytokines, including IFN-γ, TNF-α and GM-CSF early in the innate immune response that modulate adaptive immunity by regulating T cell function. The release of IFN-γ by NK cells in both inflamed tissues and secondary lymphoid organs influence the dendritic cells-initiated adaptive immune response. IFN-γ secreted by uterine NK cells may also control placental development and vascularisation during pregnancy.

Yet, only few human activating NK cell receptors have been shown to induce cytokine production upon specific engagement.

KIR2☐L4 (CD158d) induces IFN-γ, production in resting and activated NK cells. CD16 is a low-affinity FcγRIII receptor responsible for Ab-dependent cellular cytotoxicity (ADCC). Signaling via CD16 triggers the production of cytokines, including IFN-γ, GM-CSF, and several chemokines. Incubation of activated NK cells with anti-NKp30 or anti-NKp46 mAb led to IFN-γ production by NK cells. Human NKG2D activating receptor that recognizes the stress-induced MICA and MICB molecules as well as the ULBP family of molecules and plays a major role in NK cell-mediated cytotoxicity is apparently unable to produce cytokines once triggered by specific mAbs.

T cells including CD8+ and CD4+ T cells also produce cytokines. Th1 cells produce IL-2 and IFNγ, whereas Th2 cells produce IL-4. The effector functions of CD8+ T cells partially overlap those of CD4+ T cells. Naïve T cells can differentiate into at least two subsets with distinct cytokine patterns: T-cytotoxic 1 cells secrete a Th1-like cytokine pattern, while T cytotoxic 2 cells secrete Th2 cytokines. Currently, it is customary to consider IFN-γ to represent a typical type 1 cytokine, whereas the signature cytokine of type 2 response is IL-4.

Cytokines intervene in the differentiation and stimulation of antibody-producing B cell clones and the cytopathic action of cytotoxic T cells Likewise, cytokine secretion influences the cell-destroying capacity of NK cells, and the capacity of macrophages to phagocytose different bacterial plaque components.

The present invention provides with means for specifically controlling up- or down-regulation of cytokine production. The means specifically acts on the CD160 signaling pathways.

Among the different activating NK cell receptors described to date, CD160 is the only non-clonally expressed receptor on the majority of circulating NK cells. CD160+ cells correspond to the non-proliferating, highly cytolytic, $CD56^{dim}$ CD16+ NK subset. CD160 engagement by HLA-C molecules mediates cytotoxic function.

CD160 is expressed by circulating $CD56^{dim}$ $CD16^{bright}$ CD3− NK, which constitute the majority of PB-NK cells.

$CD56^{dim}$ NK cell subset is more naturally cytotoxic and produces less abundant cytokines than $CD56^{bright}$ subset following activation by monocytes. $CD56^{dim}$ NK cell subset also expresses a specific pattern of chemokine receptors and adhesion molecules. Such phenotype is characteristic of terminally differentiated effector cells. CD160+ NK cells have a high cytotoxic activity potential, do not proliferate to IL-2, and mediate cell lysis upon interaction with HLA-C.

In contrast to other human NK cell receptors described to date, CD160 receptor appears unique for the following reasons. It is encoded by a gene located on human chromosome 1, it is a glycosyl phosphatydil inositol (GPI)-anchored molecule and its cell surface expression is down-modulated by NK cell activation mediated by cytokines including IL-2 and IL-15. As described for the killer cell Ig-like inhibitory receptors, CD160 is also expressed by γδ T cells, and a subset of αβ CD8+ T cell.

SUMMARY OF THE INVENTION

The present invention relates to an anti-CD160 monoclonal antibody (mAb CL1-R2 obtainable from hybridoma TM60 accessible under CNCM deposit number I-3204) and to the conservative anti-CD160 equivalents thereof.

It more particularly relates to the applications of these anti-CD160 compounds in the fields of EC angiogenesis, and NK and T cytokine production.

The present invention indeed demonstrates that CD160 is expressed by endothelial cells (EC), and the anti-CD160 compounds of the invention can act as CD160 activating ligands. Stimulation of the CD160 signaling pathway by the anti-CD160 compounds of the invention induces an anti-angiogenic effect.

The present invention also demonstrate that CD160 is expressed not only by the cytotoxic NK and T subsets, but also by CD4+ T cells cultured with IL-15 (expressing cytotoxic activity), and that CD160 stimulation by aggregated anti-CD160 compounds of the invention leads to cytokine production. The cytokine profile that is thus obtained is unique compared to those obtained by stimulation of other NK-expressed receptors. It is also unique in the sense that it is very closely mimicking the cytokine profile induced by CD160 stimulation with natural ligands (membrane bound HLA). These cytokines notably comprise IFN-γ, TNF-α and IL-6. It is the first time that there is provided compounds which are not natural ligands, but which can induce IL-6 production from NK cells. Cytokine production induced by cell membrane HLA molecules can be inhibited using either the anti-CD160 compounds of the invention in soluble form, or anti-CD160 compounds of the invention which comprise at least one CD158b binding site in addition to their CD160 binding site(s).

The present invention hence encompasses the hybridoma TM60 as such, the CL1-R2 monoclonal antibody (mAb), the anti-CD160 compounds of the invention, any composition or kit comprising them, and any drug containing at least one of them.

The present invention also relates to means enabling the identification of CD160 ligands, CD160 membrane-associated molecules, and CD160 cytosol second messengers.

DETAILED DESCRIPTION

The present invention gives a publicly available source of an anti-CD160 specific monoclonal antibody (mAb), which is referred to by the inventors as CL1-R2. A CL1-R2 producing hybridoma has been deposited at the Collection Nationale de Cultures de Microorganismes C.N.C.M. Institut Pasteur in accordance with the terms of the Budapest Treaty on Apr. 28th, 2004 (C.N.C.M. Institut Pasteur 25, rue du Docteur Roux F-75724 Paris Cedex 15 France). The deposited hybridoma has CNCM deposit number I-3204. The present invention hence relates to the hybridoma TM60 accessible under CNCM deposit number I-3204, as well as to the anti-CD160 mAb obtainable therefrom (CL1-R2).

The present invention also provides with anti-CD160 compounds obtainable from said CL1-R2 mAb, e.g. as CL1-R2 fragments or derivatives.

The inventors further provide demonstrations relating to:
endothelial cells (EC) and angiogenesis, and to
NK and T cells and cytokine production.

These demonstrations share the common feature of implementing said CL1-R2 mAb or conservative anti-CD160 compounds obtainable therefrom.

EC and Angiogenesis:

The present invention provides the demonstration that CD160, a receptor which up to now was known to be expressed by a cytotoxic subset of NK cells and by CD8+ and TCRγδ T cells, is also expressed by endothelial cells (EC) as a membrane receptor, and that CD160 mediates HLA anti-angiogenic signaling.

The present invention also demonstrates that the anti-CD160 mAb that was said in WO 03/018048 to inhibit HLA-G action on EC does in fact not inhibit it, but mimics it.

The present invention further demonstrates that the binding of, and preferably the cross-linking of CD160 by appropriate anti-CD160 compounds inhibit the vessel formation and growth that is induced by pro-angiogenic factors such as VEGF or FGF2 on EC. The present invention thus provides the first direct demonstration that the formation of new capillaries can actually be regulated and controlled, and also provides industrially effective means therefor. The present invention hence provides actual pharmaceutical and medical applications.

Such applications notably include the prevention, symptom alleviation or treatment of those pathologies or conditions which are due to, or favored by an activity of neo-vascularization. Under these circumstances, neo-vascularization is acting as a pro-pathologic component. The activity of neo-vascularization is then considered to represent an undesired activity, or to be at an excessive level.

Such neo-vascularization-feeded pathologies or conditions notably comprise tumor growth (e.g. the growth of tumors), diabetes, ischemic ocular diseases, and rheumatoid arthritis. They also include pre-eclampsia or eclampsia, which are characterized by an insufficient blood supply at the fetus-placenta interface (insufficient or inappropriate endovascular trophoblast invasion of maternal spiral arteries).

According to an advantageous aspect of the invention, appropriate means include those anti-CD160 compounds that have an affinity for binding to CD160 that is sufficiently high to compete with CL1-R2 for binding to CD160.

As mentioned above, CL1-R2 is the anti-CD160 mAb that is produced by the hybridoma accessible under CNCM deposit number I-3204.

When it relates to EC-expressed CD160, CL1-R2 can be used in soluble form, as well as in aggregated form. Both forms induce signal transduction upon binding to CD160 (i.e. transduction of a signal of angiogenesis inhibition). The aggregated form simply has a higher affinity for binding to CD160 than the soluble form.

Anti-CD160 mAb have the special technical advantage of having a specificity that HLA ligands do not have. If they were administered to a living organism, such as e.g. a human being, HLA ligands would bind to CD160 as well as to many other receptors, and would thereby induce completely uncontrolled chain reactions in said organism. On a therapeutic point of a view, HLA ligands hence have no proven industrial applicability.

Anti-CD160 mAbs such as CL1-R2 are specific of CD160, i.e. they have a CD160 affinity that is sufficient for them to bind essentially only to CD160, at least under in vivo-like conditions. Hence, contrary to HLA ligands, anti-CD160 mAbs have industrial applicability as therapeutic agents.

The present invention hence provides for the first time agents which are able to act on CD160 as activating ligands, and which are also usable as agents to be administered in a living organism in need of a CD160 activating treatment. In short, the present invention provides the first therapeutically-compliant CD160 activating agents.

Such appropriate anti-CD160 candidate ligands of course include CL1-R2 itself, as well as conservative fragments and derivatives thereof.

An aspect of the present invention also resides in the fact that it now provides the demonstration that CD160 is not expressed by tumor cells (Lewis lung carcinoma cells), but that those EC that surrounds or infiltrates tumors actually express CD160.

The anti-CD160 mAbs as well as conservative fragments and derivatives of the invention can be used as therapeutic agents against malignant cells such as B-cell chronic lymphocytic leukaemia (CLL) which expressed CD160 molecules at their cell membrane.

The anti-CD160 compounds of the invention hence are very useful means for preventing, treating, or alleviating the symptoms of a tumor development.

The present invention also provides means to identify pharmaceutically useful compounds by screening for binding to CD160, and/or by screening for CD160-specific membrane-bound or cytosolic effectors. Such effectors represent useful target for anti-angiogenic therapy.

CD160 belongs to the immunoglobulin supergene family. Descriptive information on CD160 can be found on http://www.ncbi.nlm.nih.gov/prow/guide/1660590458g.htm. The cDNA sequence of human CD160 is described as SEQ ID NO:1 (1361 bp) in WO 98/21240 (DANA-FARBER CANCER INSTITUTE).

The mRNA sequence of human CD160 is available from Genbank under AF060981 accession number; the mRNA sequence of mouse CD160 has AF060982 Genbank accession number.

The protein sequence of human CD160 is described as SEQ ID NO:2 in said WO 98/21240, and is also available from Genbank under AAC72302 accession number (181 aa).

CD160 nucleic acids can be isolated from CD160-expressing cells following any routine procedure that is available to the skilled person [see e.g. the procedures disclosed in Molecular Cloning, A Laboratory Manual ($2^{nd}$ Ed., Sambrook, Fritsch and Maniatis, Cold Spring Harbor); Current Protocols in Molecular Biology (Eds. Aufubel, Brent, Kingston, More, Feidman, Smith and Stuhl, Greene Publ. Assoc., Wiley-Interscience, NY, N.Y. 1992].

Naturally-occurring CD160-expressing cells can notably be found within cytolytic NK and T cells (such as $CD56^{dim}$ $CD16^+$ NK cells and $TCR\gamma\delta$ and $TCR\alpha\beta^+$ $CD8^{bright}$ $CD95^+$ $CD56^+CD28^-$ $CD27^-$ cells), as well as in accordance with the present invention within epithelial cells and cytotoxic CD4+ T cells.

Isolated CD160 proteins and polypeptides are available following any routine procedure that is available to the skilled person, such as by isolation from CD160-expressing cells, or by recombinant production (see the above-mentioned reference manuals—Molecular Cloning, A Laboratory Manual; Current Protocols in Molecular Biology).

CD160 protein is of course also available in non-isolated forms, as access to a CD160 protein can be achieved through the provision of a cell expressing CD160. Cells expressing CD160 as a membrane receptor thus also provide access to a non-isolated form of CD160.

For binding experiments and/or biological activity analysis, cells expressing CD160 as a membrane receptor are a preferred source of CD160 material. Examples of such cells notably include NK cells and T cells with cytolytic activity or EC cells or cytotoxic CD4+ T cells collected from human beings, as well as cell lines such as NK92 (ATCC CRL-2407), HUVEC or human microvascular endothelial cells (HM-VEC) (*Cambrex Bio Science*, Walkersville, Md.).

CD160 proteins or polypeptides can also be provided in a clustered form. CD160 proteins or polypeptides can for example be bound to a solid support, preferably a biologically-inactive solid support, e.g. CD160-coated beads.

The present invention hence relates to anti-CD160 compounds, and to the medical and/or biological applications thereof.

The anti-CD160 compounds of the invention bind to CD160 substantially on the same epitope than CL1-R2, and preferably are capable of competing with the anti-CD160 mAb CL1-R2 (obtainable from the hybridoma deposited as CNCM I-3204) for binding to CD160.

Preferably, the anti-CD160 compounds of the invention are sufficiently CD160-specific for binding to CD160 without binding to at least one HLA receptor other than CD160, such as e.g. $CD8\alpha\beta$.

The present invention further relates to a pharmaceutical composition comprising at least one anti-CD160 compound of the invention, wherein said composition is intended for use in an anti-angiogenic therapy, and notably to an anti-angiogenic drug.

The present invention also relates to a pharmaceutical composition comprising at least one anti-CD160 compound of the invention, wherein said composition is intended for the detection of anti-angiogenic sites, and/or for the diagnosis and/or prognosis of a disease or condition involving angiogenesis.

The anti-CD160 compounds of the invention include the anti-CD160 mAb CL1-R2 itself.

CL1-R2 has proven very effective in inducing an anti-angiogenic effect upon binding to CD160, whereas prior art anti-CD160 mAb has proven ineffective. It is hence believed that targeting the correct CD160 epitope on CD160 is crucial to obtain the desired effect, namely targeting an epitope essentially similar to the one onto which CL1-R2 binds.

Hence, the anti-CD160 compounds of the invention preferably bind to CD160 on an epitope that is essentially similar to the one onto which CL1-R2 binds. Preferably, the anti-CD160 compounds of the invention bind to human CD160.

Unspecific binding can induce undesired side effects in the organism receiving an anti-CD160 compound. More particularly, if a sHLA such as sHLA-G were to be administered to a patient in need of an anti-angiogenic effect (for example, a patient having a tumor), said sHLA would bind to CD160 and induce the desired anti-angiogenic effect on EC, but would also bind to many other receptors expressed by a diversity of different cells within said patient. A sHLA such as sHLA-G would notably bind to CD8αβ expressed by T cells, and induce apoptosis of these T cells. Such an anti-T effect is highly undesirable to the patient suffering from a disease such as cancer.

The present invention provides for the first time an anti-CD160 compound which is sufficiently CD160-specific to induce an anti-angiogenesis on EC, without inducing undesired or uncontrolled side effects, such as e.g. apoptosis of T cells.

Hence, the anti-CD160 compounds of the invention preferably do not bind to human CD8αβ.

From this mAb, conservative fragments and derivatives can be easily produced by the person of ordinary skill in the art following routine procedures.

Such conservative fragments and derivatives have retained the desired binding affinity and specificity, i.e. they are qualified to be "conservative" because they still bind to substantially the same epitope as CL1-R2 and/or can compete with CL1-R2 for binding to CD160, and have retained a sufficient CD160 specificity, such as e.g. a sufficient CD160 specificity for not binding to at least one HLA receptor other than CD160, such as CD8αβ.

According to an advantageous feature of the invention, the anti-CD160 compound of the invention does not bind to the T- and NK-expressed receptor CD85j (also referred to as ILT-2). Preferably, they do not bind to human CD85j.

Preferably, the anti-CD160 compound of the invention does not cross-react with any EC receptor other than CD160.

Most preferably, the anti-CD160 compounds of the invention are fully CD160-specific, in the sense that they do not cross-react with any classical and non classical HLA molecule receptor with either allele or broad specificity. These receptors include CD8αβ, CD94 associated with each of the NKG2 family gene products (located on chromosome 12), and all the products of the genes located on chromosome 19 including KIR and ILT/LIR families.

Binding or absence of binding of an anti-CD160 compound of the invention to a receptor is meant as binding or absence of binding as would be observed under physiological conditions, or under in vitro conditions mimicking in vivo conditions. Any mean and/or procedure that the skilled person would find appropriate to perform said binding assay is suitable for determining whether a compound binds to CD160, does not bind to any other EC receptor, does not bind to CD8αβ, and does not bind to CD85j.

Illustrative conditions comprise providing a cell expressing the desired target, such as an EC (expressing CD160 and other EC receptors), or a CD8+ T (expressing CD160 and CD8αβ), or as will be shown below CD4+ T cells (expressing CD160 as demonstrated by the present invention), and contacting said CD160-expressing cell with the compound under conditions of compound concentration, contact duration, pH, and temperature that would enable binding of the cell-expressed target by its natural ligand.

Illustrative techniques to assess whether a compound binds to CD160 but not to at least one other HLA receptor, such as CD8αβ notably comprise:
flow cytometry analyses with transfected cells expressing each of the gene products capable to bind HLA molecules (CD160, CD8αβ, etc.), and/or
sensor chips (such as the sensor chips BR-1000-14, BIACORE AB, Uppsala, Sweden), which can be coated by soluble recombinant HLA ligands such as CD160, CD8αβ, etc. using a Biacore (BIACORE AB, Uppsala, Sweden).

Sources of CD160-expressing cells comprise EC collected from a healthy individual, or EC from a cell line such as NK92 (ATCC Number CRL-2407), HUVEC, HMVEC (Cambrex Bio Science, Walkersville, Md., U.S.A.).

Sources of CD8αβ-expressing cells comprise CD8+ T cells, such as CD8+ T cells collected from a healthy individual, or CD8+ T cells from a cell line such as MOLT-4 (ATCC Number CRL-1582).

Sources of CD8αβ-expressing cells comprise CD8+ T cells, such as CD8+ T cells or monocytes collected from a healthy individual, or CD8+ T cells from a cell line such as NAMALWA (ATCC Number CRL-1432).

Preferred sources are those which express the human form of the target receptor.

The human sequence of CD160 is available from the NCBI data bank under accession numbers NM_007053 (nucleic acid) and CAG46686 (protein) The human sequence of CD8α is available from the NCBI data bank under accession numbers M27161 (nucleic acid) and AAA59674 (protein). The human sequence of CD813 is available from the NCBI data bank under accession numbers M36712 (nucleic acid) and AAA35664 (protein).

The human sequence of CD85j is available from the NCBI data bank under accession numbers BC015731 and NM_006669 (nucleic acid) and AAH15731 and NP_006660.1 (protein).

The anti-CD160 compounds of the invention are anti-angiogenic agents, and are thereby useful for preventing or treating a tumor, such as a carcinoma, or a leukaemia (e.g. B-cell chronic lymphocytic leukaemia).

They are also useful for preventing or treating pre-eclampsia or eclampsia, and/or for preventing or treating diabetes, an ischemic ocular disease, or rheumatoid arthritis.

An illustrative anti-CD160 compound of the invention comprises said CL1-R2 mAb. From this mAb conservative fragments and derivatives can be produced by the skilled person following routine procedures. Such conservative fragments and derivatives are functional equivalents of said CL1-R2 mAb.

An "antibody fragment" is a portion of an antibody such as a heavy chain, a light chain, a VH, a VL, Fab, a Fab', a F(ab)2, a F(ab')2, and the like, as well as each minimal recognition units consisting of the amino acid residues that mimic the hypervariable region (CDR1H, CDR2H, CDR3H, CDR1L, CDR2L, CDR3L). Such fragments are obtainable by routine procedures, such as proteolytic digestion (for example, pepsin digestion to generate F(ab')2; papain digestion to generate Fab).

Preferred fragments of the invention are those which are conservative, i.e. those CL1-R2 fragments which have retained said desired CD160 binding affinity and specificity (i.e. have retained the feature of binding to CD160 on substantially the same epitope as CL1-R2 and/or capable of competing with CL1-R2 for binding to CD160, and the feature of binding to CD160 without binding to at least one HLA receptor other than CD160, such as e.g. CD8αβ). Preferred conservative fragment of mAb CL1-R2 comprise Fab, Fab', F(ab)2, F(ab')2 or Fv fragments of said mAb CL1-R2.

Such conservative fragments may be used as such, for biological and/or medical applications.

Non conservative fragments such as a CL1-R2CDR in isolated form are nevertheless also an object of the present invention, as they can be combined together to form a conservative derivative of CL1-R2.

The anti-CD160 compounds of the invention also comprise the conservative derivatives of said mAb CL1-R2, i.e. any anti-CD160 compound:
which is a CL1-R2 derivative in the sense that it comprises at least one CL1-R2 fragment (preferably at least one CDR of CL1-R2, preferably at least one CDR3 of CL1-R2), and
which is also conservative in the sense that the resulting derivative has retained an affinity for binding to CD160, and has also retained said CD160 binding specificity (i.e. have retained the feature of binding to CD160 on substantially the same epitope as CL1-R2 and/or capable of competing with CL1-R2 for binding to CD160, and the feature of binding to CD160 without binding to at least one HLA receptor other than CD160, such as e.g. CD8αβ).

From CL1-R2, conservative derivatives are indeed obtainable by the skilled person through synthesis and/or genetic engineering. Illustrative conservative derivatives are obtainable by the skilled person pursuant to our routine procedures.

The conservative derivative of the invention may be monovalent (one CD160 binding site), or multivalent (at least two CD160 binding sites). Preferred multivalent conservative derivatives include tetravalent conservative derivatives.

They e.g. include derivatives which are chimaeric antibodies obtainable by grafting at least one Fv fragment of CL1-R2 to an Fc fragment derived from another antibody. The Fc fragment is preferably chosen to be as less immunoreactive as possible for the organism to which said drug is to be administered. For example, when the drug is intended for administration to a human being, said Fc fragment preferably is a human Fc fragment. Conservative derivatives of the invention also include humanized antibodies, obtainable by grafting at least one CL1-R2CDR onto a human antibody frame region (hFR). The objective is here also to provide the organism into which said drug is to be administered with a compound that induces as few as undesired immunogenic side effects as possible. Conservative derivatives of the invention also include derivatives obtainable by grafting at least one CL1-R2VH region to at least one VL region, optionally via a linker (L), such as a peptide linker. Such molecules are known to the skilled person as scFv. They can be monomeric or multimeric. Appropriate linkers are those which allow the VH and VL domains to fold into a single polypeptide chain which has a three dimensional structure very similar to the original structure of the whole antibody, and thus maintain the binding specificity. Such appropriate linkers are known to the skilled person. An illustrative method to produce such linkers is described in WO 88/01649 in the name of GENEX Corp. (U.S. Pat. Nos. 4,946,778 and 5,260,203).

Said conservative derivative of mAb CL1-R2 may be monovalent, or multivalent.

An illustrative conservative derivative of mAb CL1-R2 comprises at least one scFv compound comprising at least one CL1-R2VH region of CL1-R2 linked to at least one CL1-R2VL region of CL1-R2 via a peptide linker (L).

The scFv can have a VL-L-VH orientation (see e.g. WO 88/01649 in the name of GENEX Corp. U.S. Pat. Nos. 4,946,778 and 5,260,203), or a VH-L-VL orientation (see e.g. WO 88/09344 in the name of CREATIVE BIOMOLECULES Inc. U.S. Pat. Nos. 5,132,405; 5,091,513; 5,258,498; 5,476,786; 5,482,858; 6,207,804 B1).

The scFv can be monovalent or multivalent (aggregation of several scFv).

Illustrative conservative derivative notably comprises a scFv multimer derived from said CL1-R2 mAb, joined to a Fc fragment.

Another illustrative conservative derivative of mAb CL1-R2 is a compound comprising at least one Fv fragment of CL1-R2 linked to a human Fc.

Another illustrative conservative derivative of mAb CL1-R2 is obtainable by adding one or more Fab derived from said CL1-R2 mAb at the C-terminus of each H chain of the full length CL1-R2 mAb.

Another illustrative conservative derivative of mAb CL1-R2 is obtainable by covalently linking full-length CL1-R2 mAbs together to form an aggregated Ab form.

Another illustrative conservative derivative of mAb CL1-R2 is obtainable by linking two or more Fabs head-to-tail.

A multivalent scFv according to the present invention is obtainable by linking at least two scFv in a multimer. Linking can be achieved covalently or non-covalently. Illustrative multivalent scFv are tetrameric scFv. Multivalent scFv have more than one binding site. Hence, multimeric scFv having several CD160 binding sites can be produced, to provide an anti-CD160 compound with enhanced avidity for CD160. Such multimeric scFv are particularly advantageous according to the present invention.

Multimeric scFv can be monospecific, i.e. all of their binding sites target CD160. Alternatively, multimeric scFv can comprise one or more CD160 binding site(s), as well as one or more other binding site(s) for binding to a target different from CD160. Such other binding site(s) may e.g. target a compound that is different from CD160, but still expressed by EC, so as to direct the action of the compound towards EC more efficiently.

Examples of such other target(s) comprise VEGF receptors and all receptors that induce EC growth upon ligation with their physiological ligand.

Bi- or multi-specific multimeric scFv are particularly advantageous therapeutic means. Methods to produce multimeric scFv are known to the skilled person, see e.g. WO 94/13806 in the name of The DOW CHEMICAL Company (U.S. Pat. Nos. 5,877,291 and 5,892,020), WO 93/11161 in the name of ENZON Inc. (U.S. Pat. Nos. 6,515,110 B1; 6,121,424; 6,027,725; 5,869,620).

Other conservative multivalent derivatives are obtainable by:

- joining a scFv multimer to a Fc fragment, or by
- adding one or more Fab at the C-terminus of each H chain of the full length CL1-R2 IgG, or by
- covalently linking full-length CL1-R2 to form multivalent Ab, or by
- linking two or more Fabs head-to-tail (see e.g. Miller et al. 2003 *"Design, Construction, and in vitro analysis of multivalent antibodies"* The Journal of Immunology, 170:4854-4861).

The present invention provides a pharmaceutical composition comprising as an active ingredient an anti-CD160 compound of the invention, for use in diagnosis and/or prognosis and/or therapy.

Said composition may be in any pharmaceutical form suitable for administration to a patient, including but not limited to solutions, suspensions, lyophilized powders, capsule and tablets. The pharmaceutical compositions of the invention may further comprise any pharmaceutically acceptable diluent, carrier, excipient or auxiliary.

The pharmaceutical composition of the invention may be formulated for injection, e.g. local injection, transmucosal administration, inhalation, oral administration and more generally any formulation that the skilled person finds appropriate to achieve the desired prognosis and/or diagnosis and/or therapy.

The anti-CD160 compound of the invention is contained in said pharmaceutical composition in an amount effective to achieve the intended purpose, and in dosages suitable for the chosen route of administration. More specifically, a therapeutically effective dose means an amount of a compound effective to prevent, alleviate or ameliorate symptoms of the disease or condition of the subject being treated, or to arrest said disease or condition.

Depending on the intended application, the anti-CD160 compounds of the invention, whether as CL1-R2 fragments or as CL1-R2 derivatives, may further comprise additional constituents.

For example, when the anti-CD160 compound of the invention is intended for prognosis or diagnosis, it may further comprise a detectable label, such as a fluorochrom, or an entity with enzymatic activity, or with radioactivity, and more generally any entity enabling the detection of said compound.

When the compound is intended for therapeutic administration to an organism in need thereof, it may further comprise an immunotoxin and/or a radioelement.

The anti-CD160 compounds of the invention may of course alternatively be used for the detection of anti-angiogenic sites. The present invention hence also relates to a pharmaceutical composition or kit comprising at least one anti-CD160 compound of the invention, which is intended for the detection of anti-angiogenic sites.

The present invention also relates to the use of an anti-CD160 compound of the invention, for the identification of an anti-angiogenic compound.

The present invention indeed provides the demonstration that CD160 is expressed by endothelial cells (EC), and that the anti-CD160 compounds of the invention bind to EC-expressed CD160 and thereupon induce an anti-angiogenic effect on said EC.

The anti-CD160 compounds of the invention have the advantageous ability to act as an activating extracellular ligand of CD160.

Equivalents compounds can hence be found by isolation and/or identification of compounds that show equivalent affinity and specificity for binding to CD160, i.e. that have the ability to compete with an anti-CD160 compound of the invention (such as CL1-R2 itself) for binding to CD160, and that are sufficiently CD160-specific for binding to CD160 without binding to at least one HLA receptor other than CD160, such as CD8αβ.

Such an identification and/or isolation can be achieved by e.g. screening method, such as e.g. high throughput screening.

The present invention hence also relates to a pharmaceutical composition or a kit comprising at least one anti-CD160 compound of the invention, said pharmaceutical composition or kit being intended for the identification and/or isolation of an anti-angiogenic compound.

The present invention thus also relates to the use and more particularly the in vitro use of the anti-CD160 mAb CL1-R2 (obtainable from the hybridoma deposited as CNCM I-3204), or of a conservative fragment thereof, or of a conservative derivative thereof, for the identification and/or isolation of an anti-angiogenic compound, wherein said fragment or derivative is capable of competing with CL1-R2 for binding to CD160, and is sufficiently CD160-specific for binding to CD160 without binding to at least one HLA receptor other than CD160, such as CD8αβ, and wherein said derivative comprises at least one CL1-R2 fragment.

More particularly, the present invention encompasses a method to identify an anti-angiogenic compound, characterized in that it comprises:
  providing a candidate compound,
  determining whether said candidate compound:
    has the ability to compete with CL1-R2 for binding to CD160, and
    does not bind to at least one HLA receptor other than CD160, such as CD8αβ,
  identifying said candidate compound as being an anti-angiogenic specific compound If it actually has said CD160 binding affinity and specificity.

Any candidate compound that the skilled person finds appropriate may be provided for implementation of the method of the invention. Illustrative candidate compounds may e.g. be found in chemical or biological collections, such as e.g. viral peptides or peptides deriving from pathogens (for example Cytomegalovirus peptides).

The CD160 target to be used for implementation of the methods of the invention may be provided in any form that the skilled person finds appropriate. It may e.g. be provided in the form of a cell expressing CD160 as a functional membrane receptor. Illustrative cells notably comprise EC. EC are obtainable from cell lines such as HUVEC, HMVEC, NK92 (see example 2 below). EC are also obtainable by collection and isolation from a healthy individual. The CD160 target may also be provided in the form of soluble recombinant CD160 proteins (Flag-CD160 or GST-CD160).

The present invention also relates to the use, and more particularly the in vitro use of an anti-CD160 compound of the invention as a CD160 activating ligand to identify a CD160 molecular effector or transducer, i.e. the use of an anti-CD160 compound of the invention as a CD160 ligand to identify a molecule which is involved in the anti-angiogenic signal transduction mediated by an EC-expressed CD160.

Such effectors and transducers are preferred cell targets for anti-angiogenic drugs, such as anti-tumor drugs.

The present invention hence also relates to a pharmaceutical composition or a kit comprising at least one anti-CD160 compound of the invention, said pharmaceutical composition or kit being intended for the identification and/or isolation of lipid-RAFT associated membrane molecule that is involved in CD160 anti-angiogenic signal transduction, and/or of a secondary messenger that is involved in CD160 anti-angiogenic signal transduction.

The present invention also relates to a method to identify a lipid RAFT-associated membrane molecule which is involved in CD160 anti-angiogenic signaling pathway when expressed by an endothelial cell, characterized in that it comprises:
  activating a CD160 expressed on an EC with CL1-R2 or with a conservative fragment or derivative thereof, e.g. by providing a CD160-expressing EC and contacting it with CL1-R2 or with a conservative fragment or derivative thereof so as to aggregate CD160,
  lysing said cell so as to recover the lipid RAFT domain fraction of said cell, e.g. by lysing said cell so as to dissociate the membrane complexes (e.g. by using a strong detergent such as NP40), and recovering a fraction of said lysate comprising at least one lipid RAFT domain), identifying within said RAFT fraction at least one compound which appear CD160-specific:
  by comparison with those control compounds which are obtained under similar conditions but using a non-reactive isotype-matched control Ab instead of said CL1-R2 or conservative fragment or derivative, and
  by comparison with those control compounds which are obtained under similar conditions but using a compound which does not bind to CD160 but binds to another EC-expressed receptor,
optionally, recovering said at least one CD160-specific compound thus identified,
optionally, sequencing or micro-sequencing this (these) compound(s).
whereby said at least one CD160-specific compound thus identified is a lipid RAFT-associated membrane molecule that is involved in CD160 anti-angiogenic signaling pathway.

To achieve the required comparison with said controls, any mean and/or method that the skilled person may find appropriate to compare protein patterns can be used.

For example, said RAFT fraction may e.g. be placed for migration in a 2-dimension gel (pH/PM), and the protein spots revealed with silver nitrate.

Said non-reactive isotype-matched control Ab is a non-relevant Ab which has the same isotype as CL1-R2, but which does not bind to CD160, and does also not bind to any compound that may be found within or on said EC. Said non-reactive isotype-matched control Ab may e.g. be a non-relevant mouse Ig.

Said compound which does not bind to CD160 but binds to another EC-expressed receptor may e.g. be an Ab directed to an EC receptor other than CD160, such as an anti-VEGF receptor when EC is used.

Any CD160-expressing EC may be used. Illustrative cells notably comprise EC obtainable from cell lines such as HUVEC, HMVEC, NK92 (see example 2 below), or by collection and isolation from a healthy individual.

The present invention also relates to a method to identify a secondary messenger which is involved in CD160 anti-angiogenic signal transduction when expressed by an endothelia cell, characterized in that it comprises:
  activating a CD160 expressed on an EC with CL1-R2, e.g. by providing a CD160-expressing EC and contacting it with CL1-R2 so as to aggregate CD160,
  lysing said cell under mild conditions so as to essentially preserve the putative complexes formed on CD160 (e.g. by using a mild detergent such as BRIJ58® or BRIJ98®-SIGMA-),
  optionally pre-clearing the lysate,
  recovering CL1-R2 as well as any compound that may be associated thereto, e.g. by immunoprecipitation with a goat anti-mouse Ab,
  achieving an in vitro kinase assay,
  identifying at least one compound which has incorporated at least one phosphorus compound as a result of said in vitro kinase assay,
whereby said at least one identified compound is a secondary messenger that is involved in CD160 (anti-angiogenic) signal transduction,
  optionally recovering said at least one identified compound,
  when said at least one identified compound comprises a protein or a polypeptide constituent:
    optionally achieving a trypsin digestion of said at least one recovered compound,
    optionally sequencing or microsequencing said at least one recovered compound and comparing the peptide sequence thus obtained with those available on protein data banks, or following a mass spectrometry procedure such the one described by Bruyns E, Marie-Cardine A, Kirchgessner H, Sagolla K, Shevchenko A, Mann M, Autschbach F, Bensussan A, Meuer S, Schraven B. <<T cell receptor (TCR) interacting molecule (TRIM), a novel disulfide-linked dimer associated with the TCR-CD3-zeta complex, recruits intracellular signalling proteins to the plasma membrane>> J Exp Med. 1998 Aug. 3; 188(3):561-75, so as to obtain the sequence of said protein or polypeptide constituent.

In vitro kinase assays are well-known to the skilled person. A detectable phosphorus compound (such as radioactive phosphorus provided by e.g. $P^{32}$-ATP, a fluorescent or a luminescent phosphorus compound) is usually used for such in vitro kinase assay. An illustrative experimental procedure is described in Bruyns E, Marie-Cardine A, Kirchgessner H, Sagolla K, Shevchenko A, Mann M, Autschbach F, Bensussan A, Meuer S, Schraven B. <<T cell receptor (TCR) interacting molecule (TRIM), a novel disulfide-linked dimer associated with the TCR-CD3-zeta complex, recruits intracellular signalling proteins to the plasma membrane>> J Exp Med. 1998 Aug. 3; 188(3):561-75.

To identify said at least one compound which has incorporated at least one phosphorus compound, any mean and/or procedure that the skilled person finds appropriate may be used. It may e.g. be proceeded by migration of said fraction of CL1-R2 complex on a polyacrylamide gel, optionally western blotting with anti-phosphoTyr and/or phosphoSer and/or phosphoThr, and detecting incorporated phosphorylation (with a radioactivity scintillation counter when $P^{32}$ has been used), recovering the corresponding band (e.g. by elution).

An illustrative experimental procedure can also be found by the skilled person also in Nikolova et al. 2002 ("BY55/CD160 acts as a co-receptor in TCR signal transduction of a human circulating cytotoxic effector T lymphocyte subset lacking CD28 expression" International Immunology vol. 14, No. 5, p. 445-451).

Illustrative secondary messengers that are involved in CD160 (anti-angiogenic) signal transduction have been identified by the inventors. They notably comprise pi-3-kinase and lck (p56).

Inhibitors of membrane-associated molecules and/or of cytosolic second messenger may have therapeutic applicability. They may advantageously be associated with a compound increasing the specificity of their delivery.

NK and T Cells, and the Immune System:

The present invention provides the demonstration that cytokine production by NK and T cells uses the CD160 signaling pathway in NK and T cells, and that it can be controlled by aggregated anti-CD160 compounds for up-regulation, or by soluble anti-CD160 compounds or CD160-CD158b cross-linking agents for down-regulation.

The present invention provides with anti-CD160 specific compounds that can specifically exert these controls on CD160.

The present invention also demonstrates that cross-linking CD160 to CD158b induces an inhibition of CD160 activation, thereby resulting in an inhibition of the cytokine production.

The cytokine profile that is induced by stimulation of CD160 is unique compared to the one obtained by stimulation of other NK-expressed receptors such as CD16 or NKG2D. The CD160-triggered cytokine profile is unique also in the sense that it very closely mimics the one obtained by stimulation with the natural CD160 ligand (sHLA).

Stimulation of CD160 induces the production and secretion of IFNγ, TNFα and IL-6. Except for the natural ligand sHLA, it is the first that time that there is provided a ligand that induces IL-6 production from NK cells.

The CD160 ligands provided by the present invention are anti-CD160 specific compounds. They notably comprise the anti-CD160 monoclonal antibody referred to by the inventors as CL1-R2. A CL1-R2 producing hybridoma has been deposited within the Collection Nationale de Cultures de Microorganismes in accordance with the Budapest Treaty under CNCM deposit accession number I-3204 (C.N.C.M. Institut Pasteur 25, rue du Docteur Roux F-75724 Paris Cedex 15 France).

The present invention also describes that CD160 is expressed by CD4+ T cells. Such CD160 detections could and can be made because the present invention provides a publicly-available anti-CD160 specific compound. CD160+ CD4+ cells have notably been identified within a skin sample from a human patient suffering from atopic dermatitis.

The anti-CD160 compounds of the invention which are useful for regulating NK and T cells cytokine production are identical to those which have been above-described for EC and angiogenesis: they comprise the mAb CL1-R2 of the invention as well as the conservative fragments and derivatives thereof. The structural description, the affinity and specificity properties that have been described for the anti-CD160 compounds of the invention in the context of EC angiogenesis hence apply *mutatis mutandis* to the anti-CD160 compounds of the invention in the context of regulation of NK and T cell cytokine production.

Also, similarly to what has been described in detail in the context of EC angiogenesis regulation, unspecific binding or binding to undesired targets, i.e. HLA receptors other than CD160, such as CD8αβ and/or CD85j and/or CD4 is not advantageous, as such compounds would induce uncontrolled chain reaction in the organism to which they would be administered. They would notably induce T cell apoptosis if they were comprising an anti-CD8 ligand.

There however is a functional difference between the anti-CD160 compounds of the invention when used as ligands of CD160 expressed as an immune receptor on NK and/or T cells, and the anti-CD160 compounds of the invention when used as ligands of CD160 expressed as an endothelial cell receptor.

When it relates to NK and T cells and cytokine production, it should indeed be functionally discriminated between soluble and aggregated anti-CD160 compounds.

The soluble anti-CD160 compounds of the invention induce an inhibition of CD160 signalling pathway (i.e. inhibition of cytokine production), whereas the aggregated forms of the anti-CD160 compounds of the invention induces a CD160 stimulation (i.e. induction of, or stimulation of cytokine production).

The present invention hence also relates to anti-CD160 compounds which comprise with the anti-CD160 mAb CL1-R2 (obtainable from the hybridoma deposited as CNCM I-3204), and any compound which is capable of competing with CL1-R2 for binding to CD160, and which is sufficiently CD160-specific for binding to CD160 without binding to at least one HLA receptor other than CD160, such as and preferably CD8αβ.

Preferably, the anti-CD160 compounds of the invention do further not bind to CD85j and/or CD4.

Most preferably, the anti-CD160 compounds of the invention do not bind to any HLA receptor other than CD160.

The present invention also relates to a pharmaceutical composition, such as a drug, comprising an anti-CD160 compound of the invention.

Such a drug is useful for inducing or inhibiting, and/or up- or down-regulating the cytokine production of an individual. Said cytokines notably comprise IFNγ and/or TNFα and/or IL-6.

Such a drug is useful for the (curing and/or preventing and/or palliative) treatment of any disease or condition involving an excessive or an insufficient cytokine production.

Such a drug can thus be useful for inducing or inhibiting, and/or up- or down-regulating the adaptive immunity potential of said individual. It thus enables the regulation of a Th1 response.

Said drug may also be intended for the treatment or prevention of an infection.

Said drug may also be intended as an additional product, such as an adjuvant, in a vaccine procedure to induce and/or amplify specific cytotoxic T lymphocyte (CTL) responses.

Said drug may also be intended for inducing or inhibiting, and/or up- or down-regulating hematopoiesis in an individual, for the (curing or palliative or preventive) treatment of irradiated individuals and/or for the treatment or prevention of bone marrow aplasia. Such a drug would then be very useful to patients that have been submitted to irradiation in a pre-graft treatment or as an anti-tumor treatment: the anti-CD160 compounds of the invention can indeed help them in restoring their blood cell population.

Said drug may also be intended for inducing or inhibiting, and/or up- or down-regulating an inflammatory reaction in said individual, and/or for the treatment or prevention of an allergy in said individual, such as atopic dermatitis.

Said drug may also be intended to induce a vasodilatation.

When it is intended for inhibiting and/or down-regulating the cytokine production of an individual, an anti-CD160 compound of the invention may comprise at least one CD158b binding site in addition to its CD160 binding site(s). Cross-linking of CD160 and CD158b indeed induces an inhibition of CD160 signaling pathway.

Alternatively, the anti-CD160 of the invention may be provided in soluble form. When provided in soluble form, the anti-CD160 compounds of the invention indeed inhibit CD160 signaling pathway. By "soluble" form, it is herein meant a "soluble" form as intended by the skilled person in the field of immune system receptor-ligand interactions. More particularly, the fact that a ligand is in soluble form implies that said ligand has one or two, but no more than two, binding site(s) for the activating target, i.e. in the present for CD160.

Conversely, the fact that a ligand is in aggregated form implies that said ligand has at least two binding sites for the activating target, i.e. in the present for CD160.

The anti-CD160 compounds of the invention in soluble form comprise the anti-CD160 mAb obtainable from hybridoma CNCM I-3204 (IgG).

They also comprise the conservative fragments of CL1-R2, i.e. the CL1-R2 fragments that have retained an affinity for binding to CD160, and more particularly the ability to compete with CL1-R2 for binding to CD160, and that have retained a sufficient CD160-specificity for binding to CD160, without binding to at least CD8αβ. Such conservative fragments notably comprise the Fab, Fab', F(ab)2, F(ab')2 and Fv fragments of said mAb CL1-R2.

The anti-CD160 compounds of the invention in soluble form also comprise mono- or divalent conservative derivatives of CL1-R2, i.e. a compound:

which comprises at least one fragment of said CL1-R2 mAb, and which has retained an ability to compete with CL1-R2 for binding to CD160, and has also retained a sufficient CD160 specificity for binding to CD160 without binding to at least CD8αβ, wherein said derivative has one or two CD160 binding site(s).

Illustrative mono- or divalent conservative derivatives of CL1-R2 comprise:

any humanized Ab form of CL1-R2, or any chimaeric Ab form of CL1-R2, or any mono- or divalent scFv derived from CL1-R2, optionally joined to a Fc fragment, or a CL1-R2 Fv fragment linked to a Fc fragment, or a full length CL1-R2 Ab comprising one additional CL1-R2 Fab at each its H chain.

When it is intended for inducing and/or up-regulating the cytokine production of an individual, the anti-CD160 compounds of the invention may be provided in an aggregated form, i.e. as a compound comprising at least three CD160 binding sites and no CD158b binding site.

Such aggregated forms of the anti-CD160 compounds of the invention are obtainable by aggregation of the soluble forms of the anti-CD160 compounds of the invention. Aggregated forms can be obtained by genetic manipulation or chemically with linkers.

The present invention also relates to the use of the anti-CD160 mAb CL1-R2 (obtainable from the hybridoma TM60 deposited as CNCM I-3204), or of a conservative fragment thereof, or of a conservative derivative thereof, for the identification and/or isolation of a compound having the ability to induce or inhibit, and/or to up- or down-regulate the cytokine production of a NK and/or a T CD8+ and/or a T CD4+ cell, wherein said fragment or derivative is capable of competing with CL1-R2 for binding to CD160, and is sufficiently CD160-specific for binding to CD160 without binding to at least CD8αβ, and wherein said derivative comprises at least one CL1-R2 fragment.

More particularly, the present invention encompasses a method to identify a compound having the ability to induce or inhibit, and/or to down- or up-regulate the cytokine production of a NK cell and/or a T CD8+ cell and/or a T CD4+ cell, characterized in that it comprises:

providing a candidate compound, determining whether said candidate compound:

has the ability to compete with CL1-R2 for binding to CD160, and does not bind to at least CD8αβ, identifying said candidate compound as having the ability to induce or inhibit, and/or to down- or up-regulate the cytokine production of a NK cell and/or a T CD8+ cell and/or a T CD4+ cell compound if it actually has said CD160 binding affinity and specificity.

The present invention also encompasses the use of the anti-CD160 mAb CL1-R2 (obtainable from the hybridoma deposited as CNCM I-3204), or of a conservative fragment thereof, or of a conservative derivative thereof, as a CD160 ligand to identify a molecule which is involved in the CD160-mediated cytokine production of a NK cell and/or a T CD8+ cell and/or a T CD4+ cell, wherein said fragment or derivative is capable of competing with CL1-R2 for binding to CD160, and is sufficiently CD160-specific for binding to CD160 without binding to at least CD8α(3, and wherein said derivative comprises at least one CL1-R2 fragment.

More particularly, the present invention relates to a method to identify a molecule which is involved in the CD160-mediated cytokine production of a NK cell and/or a T CD8+ cell and/or a T CD4+ cell, and which is expressed by said cell as a lipid RAFT-associated membrane molecule, characterized in that it comprises:

activating a CD160 expressed by a NK cell and/or a T CD8+ cell and/or a T CD4+ cell, with CL1-R2 or with a conservative fragment or derivative thereof, e.g. by providing a CD160-expressing NK cell and/or a T CD8+ cell and/or a T CD4+ cell, and contacting it with CL1-R2 or with a conservative fragment or derivative thereof so as to aggregate CD160, lysing said cell so as to recover the lipid RAFT domain fraction of said cell, e.g. by lysing said cell so as to dissociate the membrane complexes (e.g. by using a strong detergent such as NP40), and recovering a fraction of said lysate comprising at least one lipid RAFT domain), identifying within said RAFT fraction at least one compound which appear CD160-specific:

by comparison with those control compounds which are obtained under similar conditions but using a non-reactive isotype-matched control Ab instead of said CL1-R2 or conservative fragment or derivative, and by comparison with those control compounds which are obtained under similar conditions but using a compound which does not bind to CD160 but binds to another receptor expressed by said cell, (such as anti-CD16 or an anti-CD2 antibody when a NK cell is used, an anti-CD8 antibody when a T CD8+ cell is used, an anti-CD4 antibody when a T CD4+ cell is used), optionally, recovering said at least one CD160-specific compound thus identified, optionally, sequencing or micro-sequencing this (these) compound(s), whereby said at least one CD160-specific compound thus identified is a molecule which is involved in the CD160-mediated cytokine production of said cell, and which is expressed by said cell as a lipid RAFT-associated membrane molecule.

The anti-CD160 compounds of the invention also allows for the identification of those molecules which are expressed in the cytolic compartment of an NK cell and which are involved in the CD160 signal transduction, thereby mediated an up- or down-regulation of the cytokine production of said NK cell.

The present invention hence also relates to a method to identify a secondary messenger which is involved in the CD160-mediated cytokine production of a NK cell and/or a T CD8+ cell and/or a T CD4+ cell, characterized in that it comprises:

activating a CD160 expressed on a NK cell and/or a T CD8+ cell and/or a T CD4+ cell, with CL1-R2, e.g. by providing a CD160-expressing NK (i.e. a cytotoxic NK and/or a T CD8+ cell and/or a T CD4+ cell and contacting it with CL1-R2 so as to aggregate CD160, lysing said cell under mild conditions so as to essentially preserve the putative complexes formed on CD160 (e.g. by using a mild detergent such as BRIJ58® or BRIJ98®-SIGMA-), optionally pre-clearing the lysate,
recovering CL1-R2 as well as any compound that may be associated thereto, e.g. by immunoprecipitation with a goat anti-mouse Ab,
achieving an in vitro kinase assay,
identifying at least one compound which has incorporated at least one phosphorus compound as a result of said in vitro kinase assay,
whereby said at least one identified compound is a secondary messenger which is involved in the CD160-mediated cytokine production of said cell,
optionally recovering said at least one identified compound, and
when said at least one identified compound comprises a protein or a polypeptide constituent:
optionally achieving a trypsin digestion of said at least one recovered compound,
optionally sequencing or microsequencing said at least one recovered compound and comparing the peptide sequence thus obtained with those available on protein data banks, or following a mass spectrometry procedure such the one described by Bruyns E, Marie-Cardine A, Kirchgessner H, Sagolla K, Shevchenko A, Mann M, Autschbach F, Bensussan A, Meuer S, Schraven B. <<T cell receptor (TCR) interacting molecule (TRIM), a novel disulfide-linked dimer associated with the TCR-CD3-zeta complex, recruits intracellular signalling proteins to the plasma membrane>> J Exp Med. 1998 Aug. 3; 188(3):561-75, so as to obtain the sequence of said protein or polypeptide constituent.

As above-mentioned, in vitro kinase assay are well-known to the skilled person. A detectable phosphorus compound (such as radioactive phosphorus provided by e.g. $P^{32}$-ATP, a fluorescent or a luminescent phosphorus compound) is usually used for such in vitro kinase assay.

An illustrative experimental procedure is described in Bruyns E, Marie-Cardine A, Kirchgessner H, Sagolla K, Shevchenko A, Mann M, Autschbach F, Bensussan A, Meuer S, Schraven B. <<T cell receptor (TCR) interacting molecule (TRIM), a novel disulfide-linked dimer associated with the TCR-CD3-zeta complex, recruits intracellular signalling proteins to the plasma membrane>> J Exp Med. 1998 Aug. 3; 188(3):561-75.

An illustrative experimental procedure can also be found in Nikolova et al. 2002 ("BY55/CD160 acts as a co-receptor in TCR signal transduction of a human circulating cytotoxic effector T lymphocyte subset lacking CD28 expression" International Immunology vol. 14, No. 5, p. 445-451).

Illustrative secondary messengers that are involved in CD160 (anti-angiogenic) signal transduction have been identified by the inventors. They notably comprise pi-3-kinase and lck (p56).

The present invention also relates to:
the use of a T CD4+ cell as a source of, or as a provider of CD160 receptor,
the use of CD160 as CD4 co-receptor, and
the use of CD160 as a receptor to induce or stimulate cytokine production by a NK cell, and/or by a T CD8+ cell, and/or a T CD4+ cell,
the use of a NK cell as an IL-6 producer.

The present invention also encompasses the use of an anti-CD160 compound of the invention to induce CTL differentiation.

BRIEF DESCRIPTION OF THE FIGURES

(FIG. 1A) IL-2 treated NK92 cells were co-cultured for 4 h with $K562_{class-I+}$ in the absence or presence of blocking concentrations of W6/32 anti-HLA-C mAb (lower panel). Cells were fixed, permeabilized, and stained for intracellular TNF-α expression, as described in Materials and Methods. $K562_{class-I+}$ or NK92 cells alone were used as controls (upper panel).

(FIG. 1B) $K562_{class-I+}$, K562, and K562-Cw5 were analyzed by flow cytometry for surface expression of HLA-C using W6/32 mAb, followed by PE-conjugate (open profiles). Dark profiles are Ig-isotype control staining.

(FIG. 1C) Simultaneous measurement of IL-4, IL-6, IL-10, TNF-α and IFN-γ production by PB-NK after 16 h of culture alone or co-culture with $K562_{class-I+}$, K562 or K562-Cw5. Supernatants were collected for CBA analysis. The samples were acquired using a dual-laser flow cytometer and data displayed as two-color dot plots. Each cytokine specific set of beads is assigned a unique fluorescence intensity that is resolved on the FL-3 channel. The presence of each cytokine bound by the specific anti-IL-4, -IL-6, -IL-10, -TNF-α, and -IFN-γ antibody coating the capture beads and detected by PE-conjugated anti-IL-4, -IL-6, -IL-10, -TNF-α and -IFN-γ mAbs is indicated by the FL-2 signal intensity. Data are from one representative experiment out of five.

(FIG. 3A) Freshly purified PB-NK were immediately analyzed by flow cytometry for surface expression of CD160, CD56, CD3, CD16, CD158b, and NKG2D using PE-Cy5-conjugated BY55 anti-CD160 mAb and/or PE-conjugated anti-CD56, -CD3, -CD16, -CD158b mAbs and/or anti-NKG2D mAb, followed by PE-conjugated F(ab')₂ goat anti-mouse IgG1 Ab. Upper panel, single staining (dark profiles); open profiles are PE-Cy5-IgM or PE-IgG isotype control staining. Lower panel, double staining: the percentage of cells positive for both CD160 and another marker is indicated. Results are representative of five different experiments.

(FIG. 3B) CD160, NKG2D, and CD158b NK cell receptors were cross-linked alone or co-cross-linked on PB-NK cells with specific mAbs using the appropriate concentrations, as described in Materials and Methods. Following 16 h receptor activation, sample supernatants were analyzed by CBA, as described in Materials and Methods. Data are taken from one representative experiment out of five performed with different donors.

(FIG. 4A) Inhibition of VEGF-mediated HUVEC proliferation by sHLA-G1. Cells were seeded at low density in the presence of VEGF and incubated with varying concentrations of sHLA-G1 (sG1) or control sHLA-G1-β2m monochain (sG1mono). After 7 days of culture, cells were trypsinized and counted.

(FIG. 4B) Inhibition of VEGF-induced HUVEC migration by sG1 or sG1mono. Growth arrested HUVEC monolayers were scrapped and were either not stimulated (−) or stimulated with VEGF, in the absence (−) or in the presence of sG1 or sG1mono. 18 h later cell monolayers were stained with May-Grunwald Giemsa and the migration of cells was counted as indicated in Mat. and Methods.

(FIGS. 4C and 4D) Inhibition of FGF-2-induced HUVEC in vitro angiogenesis by sHLA-G1. HUVEC were seeded on Matrigel diluted in collagen gel in the presence or absence of FGF-2 and/or sG1. 24 h later, photographs of each well was taken (FIG. 4C), and angiogenesis was quantified as described in Materials and Methods (FIG. 4D). Photomicrographs of representative wells show the decreased FGF-2-induced HUVEC tube formation after sHLA-G1 incubation, in comparison with FGF-2 alone or FGF-2 and control. The control for sHLA-G1 is culture supernatant from untransfected cells, passed through immunoaffinity column, eluted and pooled (10). Results in A, B and D are means +/−SD of triplicate wells and are representative of five independent experiments.

(FIG. 5A) HUVEC were incubated with $^{125}$I-sHLA-G1 in the absence (−) or presence of cold VEGF, FGF-2 or varying concentrations of sHLA-G1 (sG1). Unlabeled sHLA-G1 but not VEGF nor FGF-2 prevented $^{125}$I-sHLA-G1 binding.

(FIG. 5B) HUVEC were incubated with iodinated VEGF in the presence of cold sG1, FGF-2 or VEGF. Unlike cold VEGF, cold sG1 did not abrogate iodinated VEGF binding. Results are means+/−SD of triplicate wells and are representative of 5 independent experiments.

FIGS. 6A, 6B, 6C. sHLA-G1 binds to the CD160 receptor expressed by EC.

(FIG. 6A) HUVEC were analyzed by flow cytometry after incubation with CD8, ILT2 or CL1-R2 (CD160) specific mAbs (open profiles) or Ig-isotype control Ab (black profiles) followed by FITC-labeled conjugates, in the presence or not of VEGF or sG1. Results are representative of six independent experiments.

(FIG. 6B) CD160 mRNA expression in NK92, HUVEC and PB-CD4+ lymphocytes was measured by RT-PCR, using CD160 (top) or β-actin (bottom) primers.

(FIG. 6C) Predicted amino acid sequence alignment of CD160 expressed in NK92 (NK) and HUVEC. (−) indicate identity.

(FIG. 7A, upper), By flow cytometry, mAb CL1-R2 stained Jurkat-CD160 but not untransfected Jurkat (open profiles). Black profiles are Ig-isotype control stainings.

(FIG. 7A, lower), HLA-G1 tetramer cross-linked with W6/32 mAb, followed by incubation with streptavidin-PE, binds to Jurkat-CD160 but not to untransfected Jurkat, whereas not-cross-linked HLA-G1 tetramer, followed by incubation with streptavidin-PE, binds to HUVEC (open profiles). Black profiles are control staining with streptavidin-PE.

(FIG. 7B) HUVEC were incubated or not with sHLA-G1 (100 ng/ml) at 4° C. After 2 h, cells were incubated with CL1-R2 mAb followed by PE-conjugate and analyzed by flow cytometry (open profiles). Black profile is Ig-isotype control staining. Results are representative of 3 independent experiments.

HUVEC were seeded on Matrigel diluted in collagen gel in the presence or absence of FGF-2 and sHLA6G1 and/or mAb CD160 or Ig-isotype control. 24 h later, photography of each well was taken and angiogenesis quantified as described in Materials and Methods. Results are mean+/6 SD of triplicate wells and are representative of 5 independent experiments.

Figures 9A, 9B:
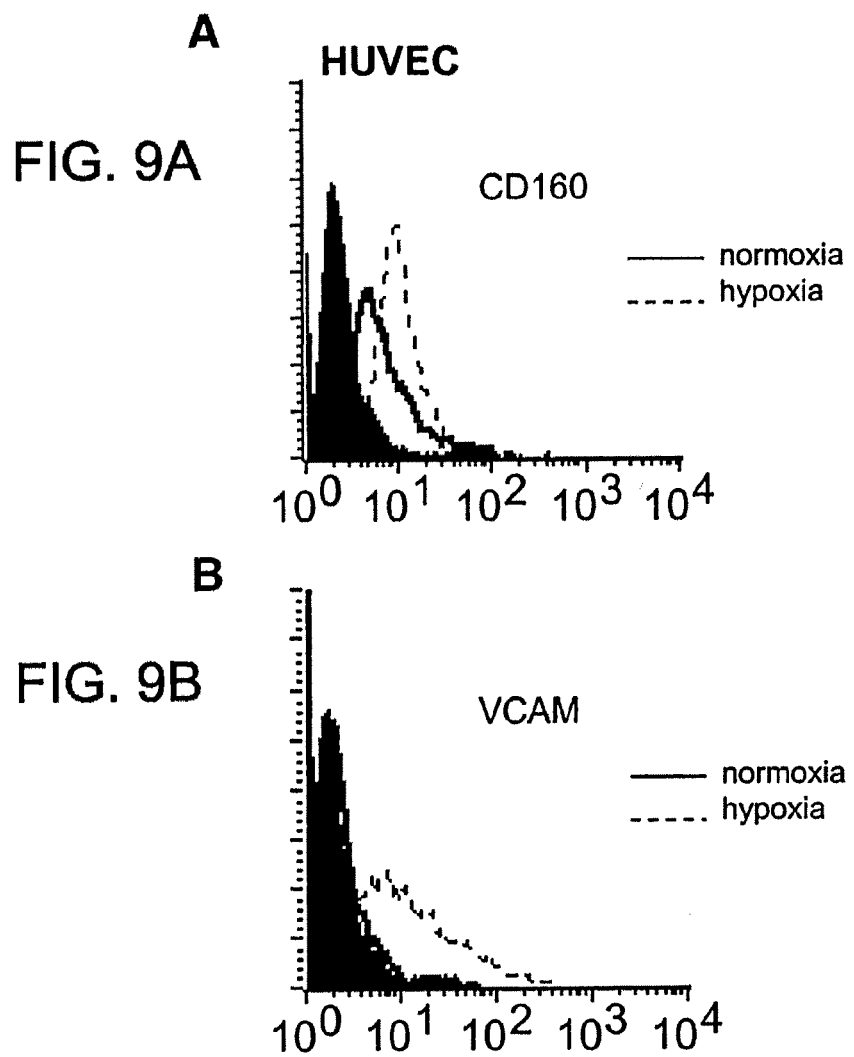

FIGS. 9A, 9B. Effect of hypoxia on EC CD160 expression.

HUVEC were incubated in normoxia or hypoxia (5% O2) conditions during 24 h and analyzed for surface expression of CD160 using CL1-R2 mAb (FIG. 9A), or VCMAM, using anti-CD106 mAb (FIG. 9B), followed by PE-labeled conjugate. Black profiles are Ig-isotype control stainings. Results are representative of 3 independent experiments.

FIGS. 10A, 10B, 10C, 10D. CL1-R2 mAb immunohistochemistry on tumor sections, showing that CD160 is not expressed by tumor cells, but is expressed at a high level by EC of lymphatic vessels at the periphery of the tumor and EC of microvessels inside the tumor.

(FIGS. 10A and 10B) CD160 staining of lymphatic microvessels at the periphery of the tumor.

(FIGS. 10C and 10D) CD160 staining of microvessels inside the tumor.

Figure 11:
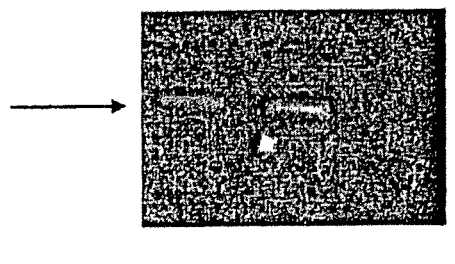

FIG. 11. Induction of CD160 transcripts in CD4+ lymphocytes with IL-15.

FIG. 12a, 12b, 12c, 12d. sHLA-G1 inhibits VEGF- or FGF2-mediated endothelial cell proliferation, migration and capillary-like tube formation. (a) Proliferative response of HUVEC to VEGF. Effects of recombinant sHLA-G1 (sG1) or control sHLA-G1-☐2m monochain (sG1mono). (b) Inhibition of VEGF-induced HUVEC migration by sHLA-G1. Growth arrested HUVEC monolayers were scraped and were either not stimulated (untreated) or stimulated with VEGF, in the absence (−) or in the presence of sG1 or sG1mono. 16 h later cell monolayers were stained with May-Grunwald Giemsa and the migration of cells was counted as indicated in Methods. (c, d) sHLA-G1 inhibits FGF-2-induced angiogenesis. HUVEC were seeded on Matrigel in the presence or absence of FGF-2 and/or sG1. Photographs of each well were taken after 24 h. (c), and angiogenesis was quantified as described in Materials and Methods (d). The control is culture supernatant from untransfected cells, passed through immunoaffinity column, eluted and pooled[34]. ***P<0.001, ANOVA test. Results in (a, b, and d) are means+/−SEM of triplicate wells and are representative of five independent experiments.

FIG. 13a, 13b, 13c, 13d, 13e. sHLA-G1 induces apoptosis of endothelial cells. (a) Kinetics curve of apoptosis induction. SGHEC-7 cells were incubated with conditioned media from PC3 cells transfected with sHLA-G1 (G1s) or empty vector (neo). Time lapse microscopy was carried out to assess the appearance of apoptotic morphology. Mean±SEM of pooled data from seven experiments is shown. Although data were obtained every 15 min, data points are only shown every 2 h for clarity. (b) Images of endothelial cells after treatment with sG1 or neo conditioned media (Supplementary FIG. 2 video clip online). (c) Kinetics curve of apoptosis induction by recombinant sHLA-G1 in the presence or absence of the caspase inhibitor zVAD-fmk assessed by time-lapse microscopy. Mean±SEM of pooled data from four experiments is shown. (d) The area under the curve was calculated from the kinetics curves shown in (c). **P<0.003 Mann Whitney U test. (e) Western blot analysis of p85 cleaved PARP expression. SGHEC-7 cells were incubated in the absence (control) or presence of sHLA-G1.

Figure 14:
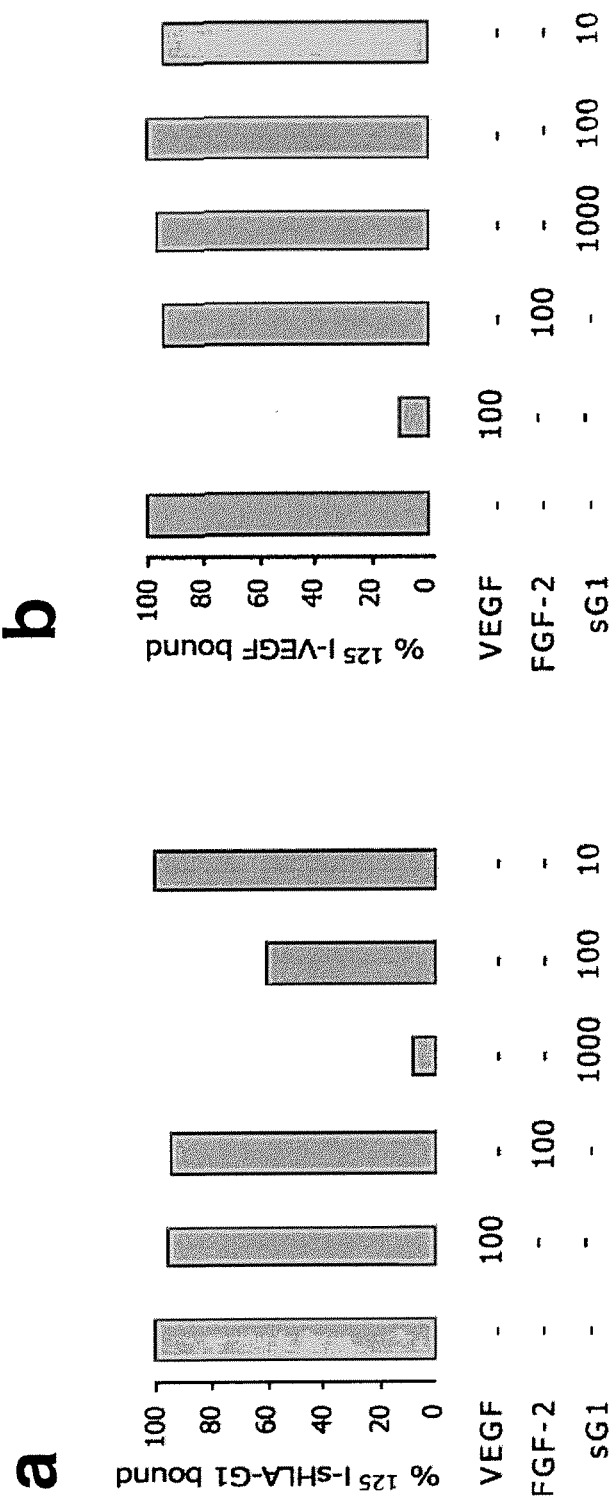

FIG. 14a, 14b. sHLA-G1 does not interfere with VEGF receptors. (a) HUVEC were incubated with $^{125}$I-sHLA-G1 in the absence (−) or presence of cold VEGF, FGF-2 or varying concentrations of sHLA-G1 (sG1). Unlabeled sHLA-G1 but not VEGF nor FGF-2 prevented $^{125}$I-sHLA-G1 binding. (b) HUVEC were incubated with $^{125}$I-VEGF in the presence of cold sG1, FGF-2 or VEGF. Unlike cold VEGF, cold sG1 did not abrogate iodinated VEGF binding. Results are means+/−SEM of triplicate wells and are representative of three independent experiments.

Figure 15:
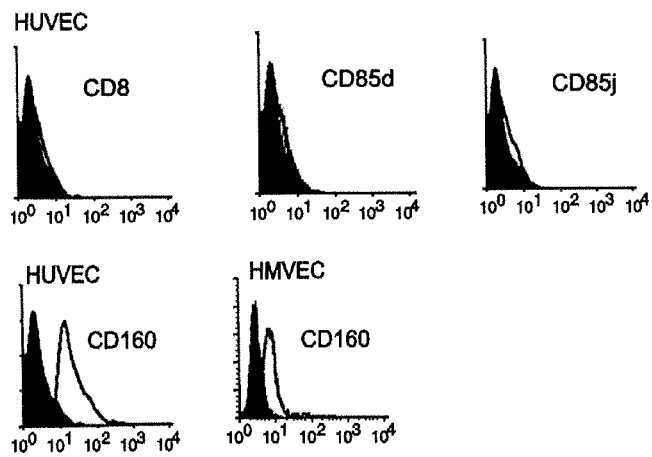
Figure 15:
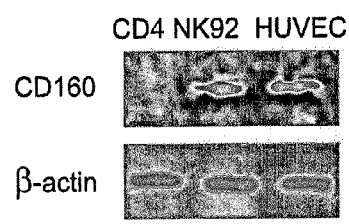
Figure 16:
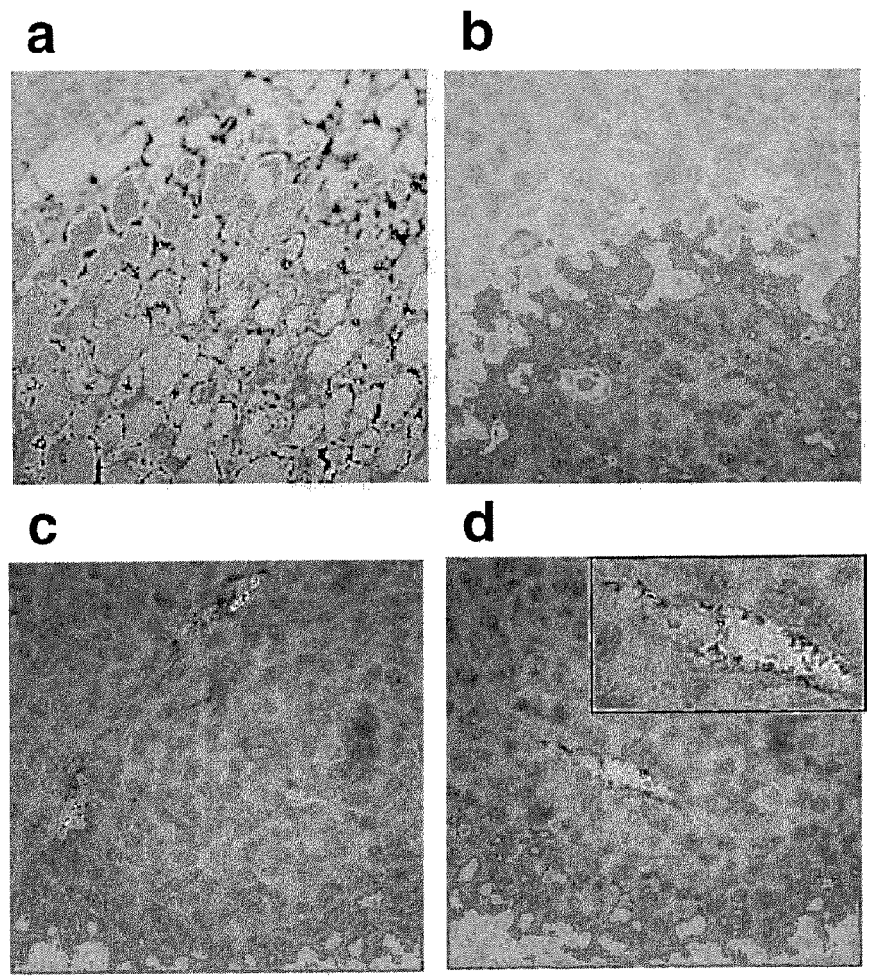

FIG. 15a, 15b, 15c. HUVEC express the CD160 receptor. (a) HUVEC and HMVEC were analyzed by flow cytometry after incubation with CD8, CD85d, CD85j or CL1-R2 (CD160) specific mAbs (open profiles) or Ig isotype controls (black profiles) followed by FITC-labeled conjugates. Results are representative of six independent experiments. (b) CD160 mRNA expression by HUVEC. (c) Predicted amino acid sequence alignment of CD160 expressed in HUVEC and NK92. (−) indicates identity.

FIG. 16a, 16b, 16c, 16d. Immunohistochemical staining of Lewis lung carcinoma tumor sections with anti-CD160 mAb demonstrating CD160 positive vessels in brown. Vessel network staining was localized at the periphery of the tumor (a). Blood vessels in the periphery (b) and the centre of the tumor (c,d) were also stained with CD160 mAb, whereas tumor cells remained unstained. Magnification, ×400.

FIG. 17a, 17b, 17c, 17d. sHLA-G1 binds to the CD160 receptor expressed by endothelial cells. (a, upper), anti-CD160 mAb stains Jurkat-CD160 but not untransfected Jurkat (black profiles, isotype control). (a, lower), HLA-G1 tetramer binds to HUVEC and Jurkat-CD160 control transfectant but not to untransfected Jurkat cells (black profiles, control staining with streptavidin-PE). (b) Recombinant sHLA-G1 blocks CD160 mAb binding to HUVEC (black profile, isotype control). Results are representative of three independent experiments. (c) Soluble CL1-R2 anti-CD160 mAb triggers inhibition of in vitro angiogenesis. HUVEC were seeded on Matrigel in the presence or absence of FGF-2 and sHLA-G1 and/or mAb CD160 (+++, 10 µg/ml; +, 1 µg/ml) or IgG1-isotype control (10 µg/ml). Photographs of each well were taken after 24 h and angiogenesis quantified. Results are mean+/−SD of triplicate wells and are representative of five independent experiments. ***P<0.001, *P<0.005 by ANOVA test, compared to FGF-2-treated cells. (d) Soluble CL1-R2 anti-CD160 mAb induces endothelial apoptosis. SGHEC-7 cells were incubated with CL1-R2 (+, 1 µg/ml, ++, 5 µg/ml, +++, 10 µg/ml) or IgG1 isotype control (10 µg/ml) and time lapse microscopy was carried out to assess the appearance of apoptotic morphology. Levels of apoptosis after 50 h are shown with mean±SD of pooled data from 3 experiments. *P<0.05, P<0.01, *P<0.001 by ANOVA test, compared to control.

Figure 18A:
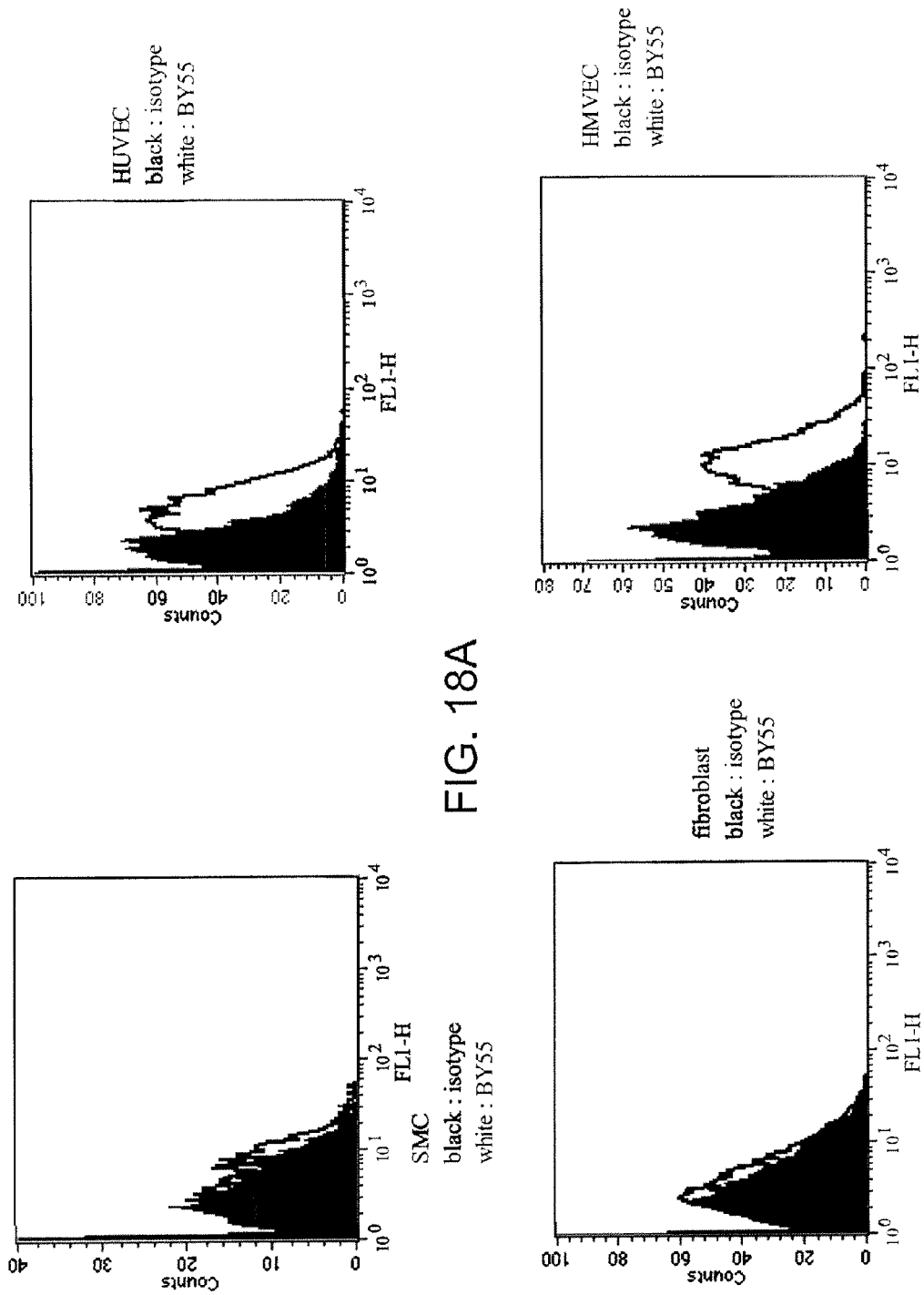

FIG. 18a: Expression of CD160 on HUVEC and HMVEC as compared to negative control cells (Smooth muscle cells and human fibroblast in primary culture). Flow cytometry analysis using BY55 anti-CD160 mAb (IgM) as compared to IgM isotype control. Cells were incubated with either of these antibodies, washed and incubated with an anti-IgM-FITC conjugate.

Figure 18B:
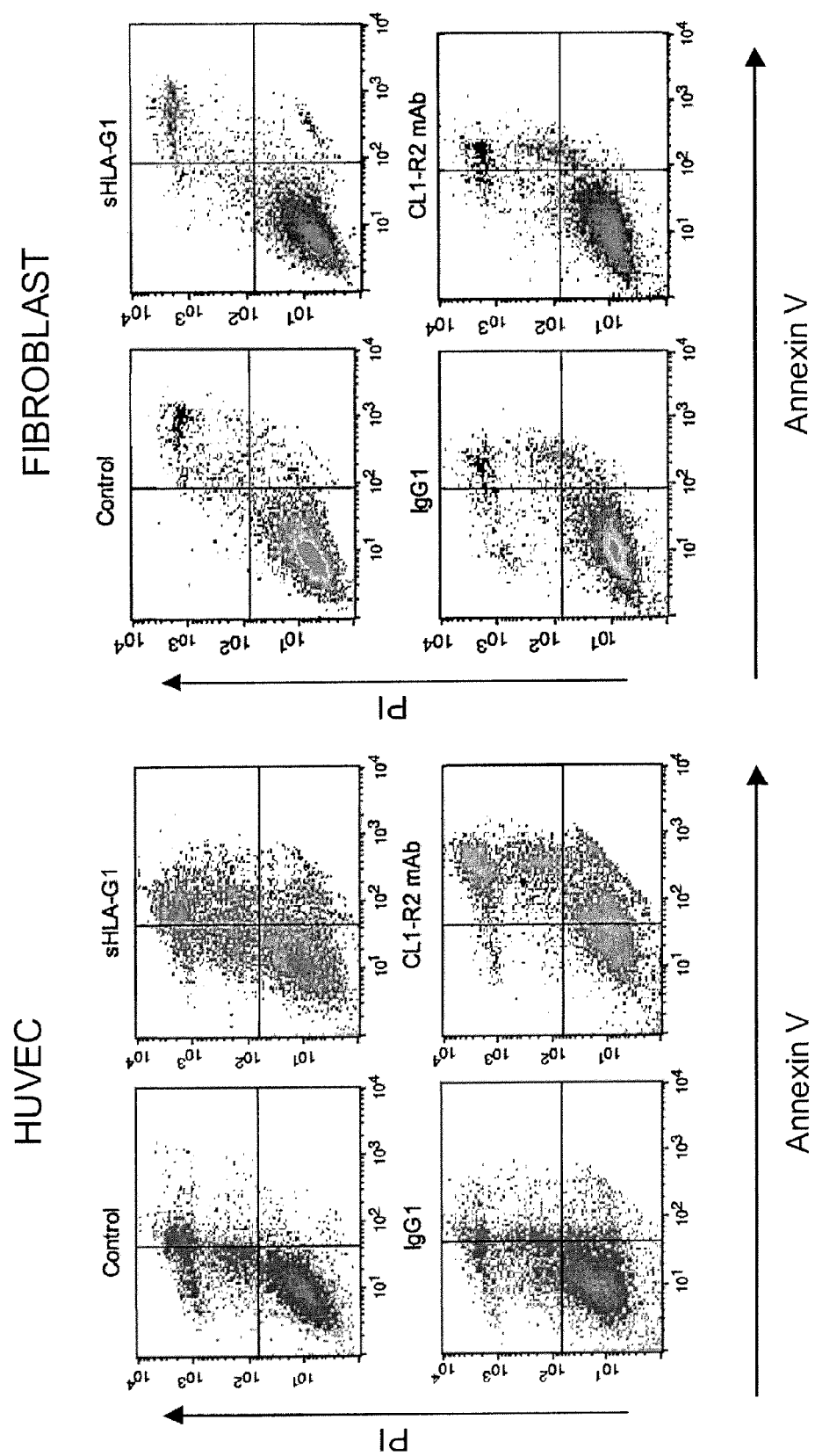

FIG. 18b: CL1-R2 mAb induces apoptosis of HUVEC but not of fibroblast (Assessment by annexin-V and PI double-staining flow cytometry)

Figure 18C:
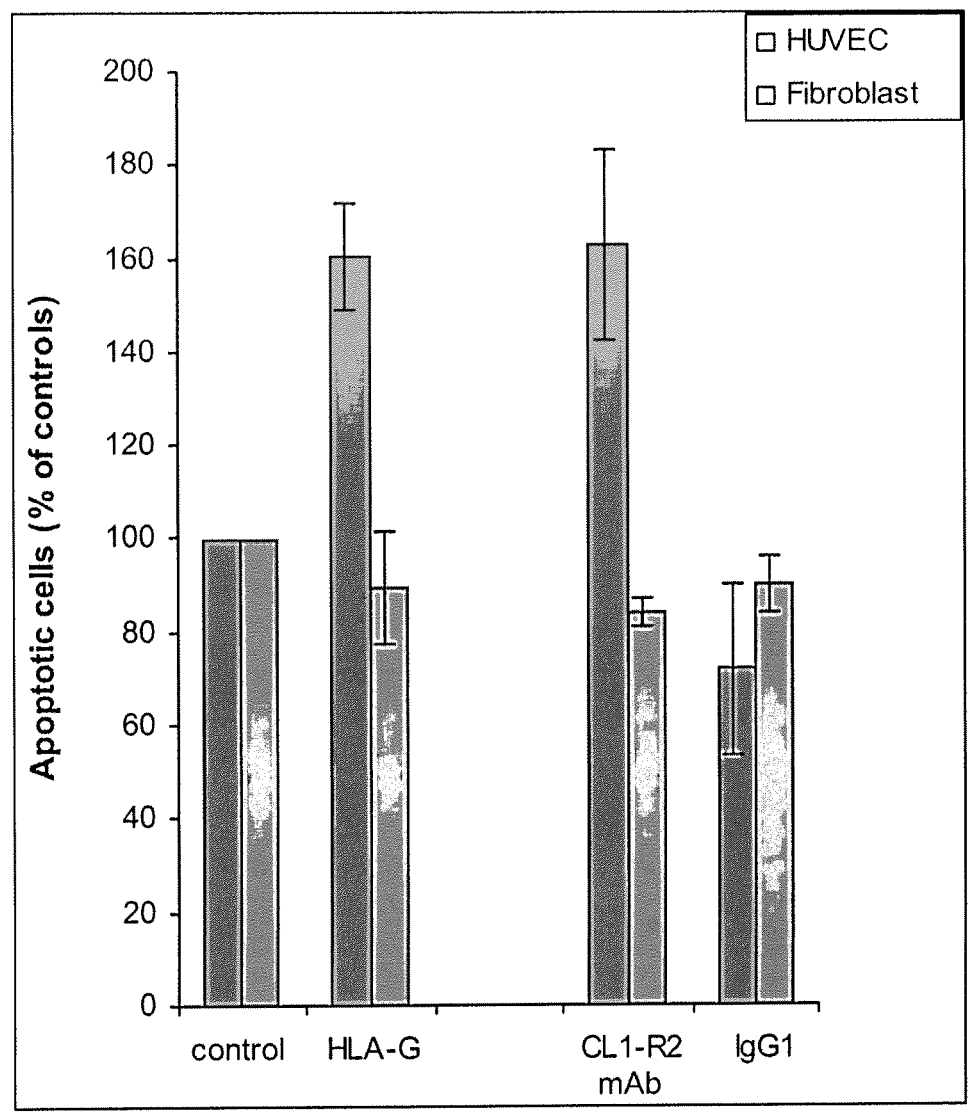

FIG. 18c: Same method as in FIG. 18b. Mean of 2 different experiments (5 different wells for each experiment)

EXAMPLES

Example 1

Engagement of CD160 by its HLA-C Physiological Ligand Triggers a Unique Cytokine Profile Secretion in the Cytotoxic Peripheral Blood NK Cell Subset Materials and Methods Cells. Effector cells were the human CD160$^+$ NK92 line (ATCC Number CRL-2407) cultured with IL-2 for several days, and fresh human peripheral blood (PB)-NK cells derived from normal donors, purified by immunomagnetic NK cell isolation kit (Miltenyi Biotec). PB-NK purity was shown to be >90% CD3$^-$CD56$^+$ by flow cytometry and >90% of purified PB-NK were CD160$^+$.

Two variants of human K562 erythroleukemia cells were used as target cells: one variant (K562$_{class\ I+}$) expressed HLA-C when cultured with IFN-γ (publication under reference 14; ATCC CCL-243) whereas the other (K562 cultured with IFN-γ, ATCC CCL-243) did not. K562-HLA-Cw5 transfectants (K562-Cw5) were obtained by transfection of HLA-Cw5 cDNA in K562 MHC class I negative parental cells.

Antibodies and flow cytometry analysis. mAbs used included:
- CL1-R2 (anti-CD160 IgG1; hybridoma TM60 available from C.N.C.M. Institut Pasteur 25, rue du Docteur Roux F-75724 PARIS CEDEX 15 FRANCE under C.N.C.M. deposit number=I-3204),
- BY55 (anti-CD160 IgM; Beckman-Coulter),
- W6/32 anti-HLA (IgG2a; ATCC Number HB-95), referred here as anti-HLA-C,
- PE-conjugated 3G8 anti-CD16 (IgG1; Beckman-Coulter),
- GL183 anti-CD158b (IgG1; Beckman-Coulter),
- anti-CD3 (UCHT1 from Beckman-Coulter)
- anti-CD56 (Beckman-Coulter), and
- anti-NKG2D clone 149810 (IgG1, R & D Systems).

For single staining flow cytometry analysis, cells were incubated with PE-Cy5-conjugated BY55 anti-CD160 mAb or with the other PE-conjugated mAbs. For the NKG2D staining, cells were incubated with anti-NKG2D mAb followed by PE-conjugated F(ab')$_2$ goat anti-mouse IgG1 Ab (Cliniscience). For double staining, cells were incubated with PE-Cy5-conjugated BY55, followed by PE-conjugated anti-CD56, -CD3, -CD16, -CD158b mAbs, or by anti-NKG2D mAb followed by PE-conjugated F(ab')$_2$ goat anti-mouse IgG1 Ab. PE-Cy5-IgM or PE-IgG (Beckman-Coulter) were used as isotype controls. Samples were analyzed on an EPICS XL4C flow cytometer (Beckman-Coulter).

Receptor specific mAb-mediated cross-linking. Cross-linking of CD160, NKG2D, CD16, or CD158b receptors on PB-NK cells was performed in the final concentration of 1-10 µg/ml during 16 h incubation at 37° C. in 5% CO$_2$. IgG1 isotype control was also used at the same conditions. 100 U/ml IL-2 was added during the incubation time. Supernatants were collected and stored at −80° C. until further analysis.

NK cells and CD160 ligand-expressing cells co-cultures. NK92 or PB-NK cells were incubated alone or co-incubated either with K562$_{class\ I+}$, K562 or K562-Cw5 at a ratio of 10:1 during 4 h (NK92) or 16 h (PB-NK) at 37° C. in the presence or not of blocking concentrations (25-50 µg/ml) of W6/32 or CL1-R2 mAbs or Ig-isotype controls. 100 U/ml IL-2 was added during the incubation times.

Intracellular TNF-α detection. NK92 cells treated as above were washed, fixed in 2% paraformaldehyde, permeabilized with 0.1% saponin for 10 min, stained by PE-conjugated anti-TNF-α mAb or mouse IgG1-PE (Coulter-Immunotech) and analyzed by an EPICS XL4C flow cytometer (Coulter).

Cytokine measurement by Cytometric Bead Array. The Th1/Th2 Cytometric Bead Array (CBA) kit (BD Biosciences) was used for simultaneous measurement of IL-2, IL-4, IL-6, IL-10, TNF-α and IFN-γ according to the manufacturer's instructions (Cook, E. B., J. L. Stahl, L. Lowe, R. Chen, E. Morgan, J. Wilson, R. Varro, A. Chan, F. M. Graziano, and N. P. Barney. 2001. Simultaneous measurement of six cytokines in a single sample of human tears using microparticle-based flow cytometry: allergics vs. non-allergics. J. Immunol. Meth. 254:109-118). Briefly, CBA uses a series of uniform-size beads with discrete fluorescence intensity (FL3). Each series of beads is coated with a mAb against a single cytokine (IL-2, IL-4, IL-6, IL-10, TNF-α or IFN-γ and the mixture of beads detects six cytokines in one sample. A cytokine standard containing a mixture of predetermined amounts of all six cytokines was used to prepare standard curves. 10 µl aliquot of each capture bead specific for IL-2, IL-4, IL-6, IL-10, TNF-α and IFN-γ was mixed for each assay tube to be analyzed. Then 50 µl of such mixed capture beads, 50 µl of human Th1/Th2-PE detection reagent and 50 µl of appropriate test sample (frozen supernatants from different treated PB-NK cells, thawed and centrifuged prior analysis) were added to each assay tube. Tubes were incubated for 3 h at room temperature, washed and reconstituted in 300 µl of wash buffer. Finally, IL-2, IL-4, IL-6, IL-10, TNF-α and IFN-γ cytokine-bound cytometric beads were analyzed on a FACScalibur flow cytometer (Becton Dickinson) using CELLQuest (Becton Dickinson). The mean fluorescence was compared with standard curves and cytokine concentrations (pg/ml) calculated by using the CBA software provided (BD Biosciences). IL-2 measurements were excluded from analysis because the culture medium in which NK cells were incubated during the different assays always contained IL-2.

Statistics. Statistical analyses were performed using either the two-tailed Student-T test or Student paired-T test with p 0.05 defined as significant.

Results and Discussion

Figure 1A:
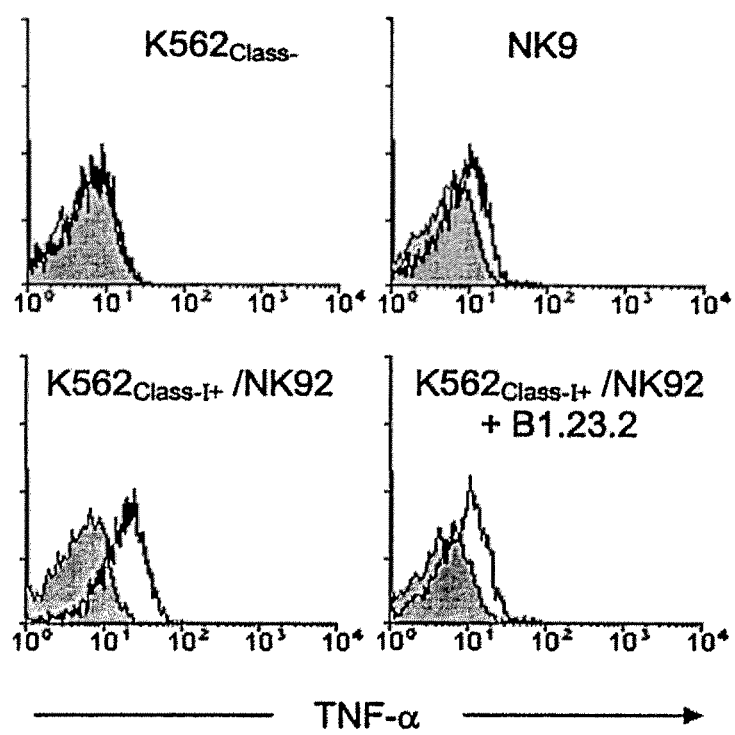
FIGS. 1A, 1B, 1C. HLA-C triggers cytokine production by NK92 and PB-NK cells.

HLA-C Expressing K562 Target Cell Lines Trigger Cytokine Production by PB-NK Cells We investigated whether TNF-α production could be obtained in the NK92 cell line which expresses high amount of CD160. Intracellular expression of this cytokine was evaluated by flow cytometry in NK92 co-cultured with HLA-C expressing K562 ($K562_{class\ I+}$) target cells. We found that such co-culture stimulated TNF-α production, as compared with the moderate secretion of this cytokine by NK92 cultured alone (FIG. 1A). Absence of TNF-α production by $K562_{class\ I+}$ alone indicated that TNF-α release was produced solely by NK92. Furthermore, addition in the culture medium of mAb W6/32-mediated HLA-C-masking on target cells resulted in a diminishment of TNF-α production by NK92 (FIG. 1A). These results indicate that HLA-C was capable to trigger NK92 to secrete TNF-α.

Figure 1B:
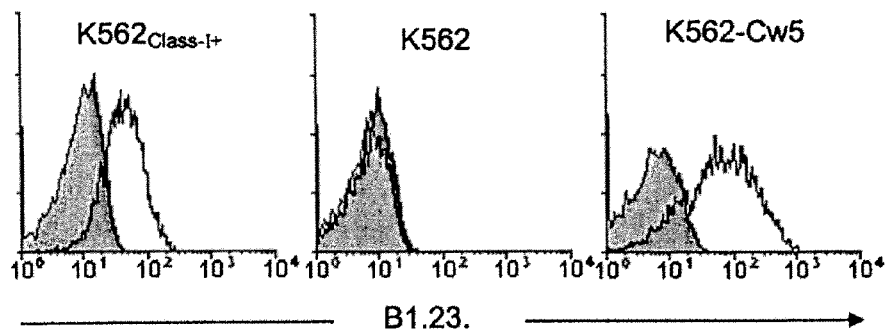

Next, we evaluated whether cytotoxic PB-NK could also produce TNF-α upon specific HLA-C-mediated triggering. PB-NK were co-cultured for 16 h either with $K562_{class\ i+}$, K562-Cw5 transfectant, which both express HLA-C molecules at their cell surface, or with K562 which is entirely MHC class I negative (FIG. 1B). Using the CBA kit and flow cytometry, TNF-α and four other Th1/Th2 cytokines were measured in the cell-free supernatant fluid (FIG. 1C for one representative experiment and Table I for 5 independent experiments).

TABLE I

IFN-γ, TNF-α and IL-6 production by PB-NK cells co-cultured with HLA-C expressing K562 cells

| Cells | IFN-γ (pg/ml) | TNF-α (pg/ml) | IL-4 (pg/ml) | IL-6 (pg/ml) | IL-10 (pg/ml) |
|---|---|---|---|---|---|
| NK | 185 ± | 16 ± | 0 | 16 ± | 0 |
| NK/$K562_{Class-I+}$ | $29,441^d$ ± | $334^b$ ± | 0 | $620^b$ ± | 0 |
| NK/K562 | 296 ± | 19 ± | 0 | 33 ± | 0 |
| NK/K562-Cw5 | $20,089^c$ ± | $3896^b$ ± | 0 | $689^a$ ± | 0 |

Purified PB-NK cells were cultured alone (NK) or co-cultured with $K562_{Class-I+}$, K562, or K562-Cw5 cells. After 16 h, culture supernatants were collected and cytokine concentrations measured by Cytometric Bead Array, as described in Materials and Methods. Less than 10 pg/ml concentration was considered as 0. Results are expressed as mean ± SE of five independent experiments performed with different donors which were selected according to the absence of cytokine production when PB-NK were co-cultured with K562.
$^a$P < 0.03, as compared to the NK group (Paired Student T-test).
$^b$P < 0.02
$^c$P < 0.01
$^d$P < 0.008

Figure 1C:
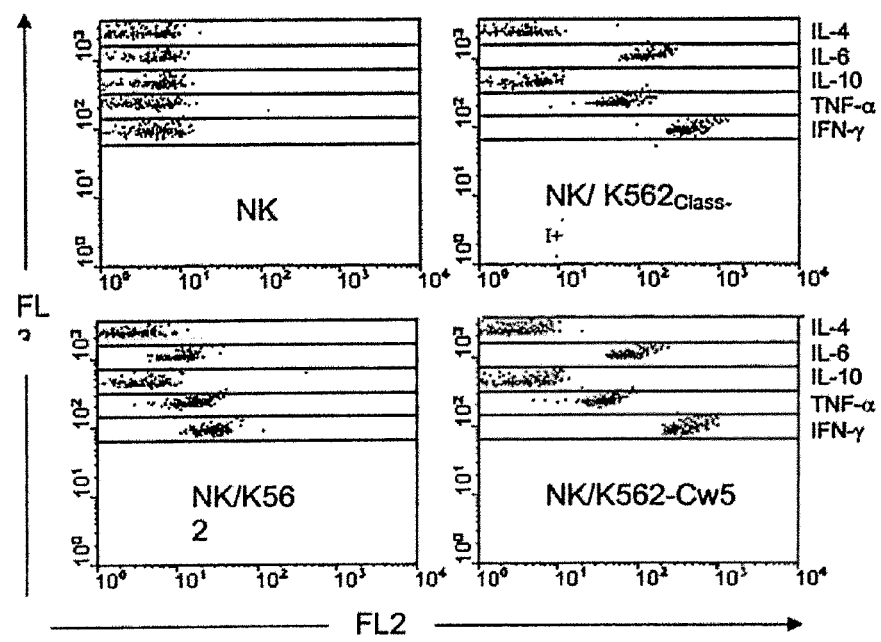

When PB-NK from different donors were co-cultured with $K562_{class\ i+}$ or K562-Cw5, a large amount of IFN-γ, TNF-α and IL-6 was detected and neither IL-4 nor IL-10. By comparison, PB-NK co-cultured with class I negative K562 produced very low amounts of IFN-γ and only marginal amounts of TNF-α and IL-6, not significantly different from those observed when PB-NK cells were cultured alone (FIG. 1C and Table I). No spontaneous cytokine release was ever produced when K562 or $K562_{class\ I+}$ were cultured alone. However, we should mention that, in some donors, PB-NK did produce cytokines when co-cultured with K562. This suggested that MHC class I-independent activating receptors could be also involved. Altogether, these data indicate that HLA-C physiological ligand recognition by cytotoxic PB-NK cell subset could trigger specific cytokine secretion.

Specific Engagement of CD160 by its Physiological Ligand HLA-C Results in IFN-γ, TNF-α and IL-6 Production by PB-NK We investigated whether CD160 receptor triggered specific cytokine secretion by PB-NK upon engagement with HLA-C. PB-NK were co-cultured with $K562_{class\ i+}$ in the presence of blocking concentrations of mAbs to either CD160 or HLA-C, or of 1g-isotype controls (Table II).

TABLE II

Anti-CD160 and -HLA-C blocking mAbs prevent production of IFN-γ, TNF-α and IL-6 by PB-NK co-cultured with $K562_{ClassI+}$

| Type | IFN-γ (pg/m | TNF-α (pg/m | IL-4 (pg/m | IL-6 (pg/m | IL-10 (pg/m |
|---|---|---|---|---|---|
| NK | 186 ± | 18 ± | 0 | 20 ± | 0 |
| NK/$K562_{Class-I+}$ + IgG1 | 23,054 ± | 200 ± | 0 | 414 ± | 0 |
| NK/$K562_{Class-I+}$ + anti-CD160 mAb | $1,083^a$ ± | $58^c$ ± | 0 | $143^b$ ± | 0 |
| NK/$K562_{Class-I+}$ + IgG2a | 16,125 ± | 215 ± | 0 | 478 ± | 0 |

TABLE II-continued

Anti-CD160 and -HLA-C blocking mAbs prevent
production of IFN-γ, TNF-α and IL-6 by PB-NK co-cultured with K562$_{Class-I+}$

| Type | IFN-γ (pg/m | TNF-α (pg/m | IL-4 (pg/m | IL-6 (pg/m | IL-10 (pg/m |
|---|---|---|---|---|---|
| NK/K562$_{Class-I+}$ + anti-HLA-C mAb | 1,149$^c$ ± | 64$^c$ ± | 0 | 370 ± | 0 |

Purified PB-NK cells were cultured alone (NK) or co-cultured with K562$_{Class-I+}$ in the presence of anti-CD160, or anti-HLA-C mAbs at blocking concentrations or Ig isotype controls. After 16 h of incubation, culture supernatants were collected and cytokine concentrations measured by Cytometric Bead Array, as described in Materials and Methods. Less than 10 pg/ml concentration was considered as 0. Results are expressed as mean ± SE of four independent experiments performed with different donors.
$^a$P < 0.04, as compared to the control NK/K562$_{Class-I+}$ + IgG1 group (Student T-test).
$^b$P < 0.03
$^c$P < 0.01

Figure 2:
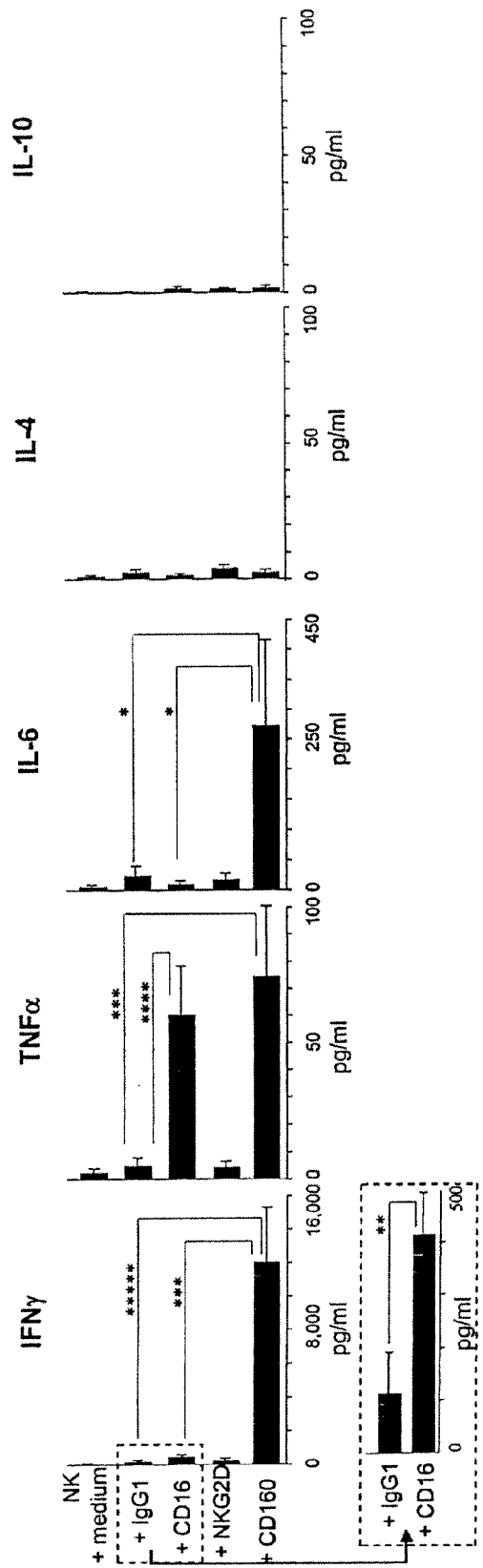
FIG. 2. CD160 mAb cross-linking triggers TNF-α, IFN-γ and IL-6 cytokine production by PB-NK cells. After cross-linking of CD160, CD16, NKG2D, and NK cell receptors by specific mAbs during 16 h incubation, sample supernatants were analyzed by CBA for cytokine production, as described in Materials and Methods. Cytokine concentrations in the samples were calculated relative to the appropriate calibration curves with standard dilutions for each cytokine. Results are expressed as mean±SE of nine independent experiments performed with different donors. *P≦0.05, P≦0.03, *P≦0.01, **P<0.003, ***P≦0.008 (Student T-test).
Figure 3A:
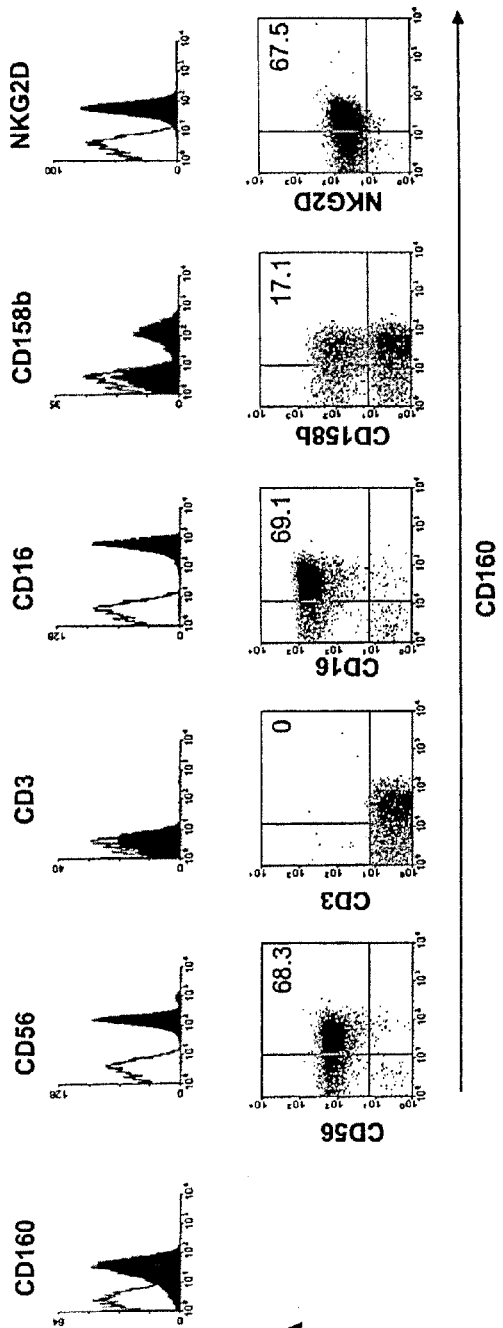
FIGS. 3A and 3B. Inhibition of CD160-mediated TNF-α, IFN-γ and IL-6 cytokine production by the CD158b inhibitory receptor.
Figure 3B:
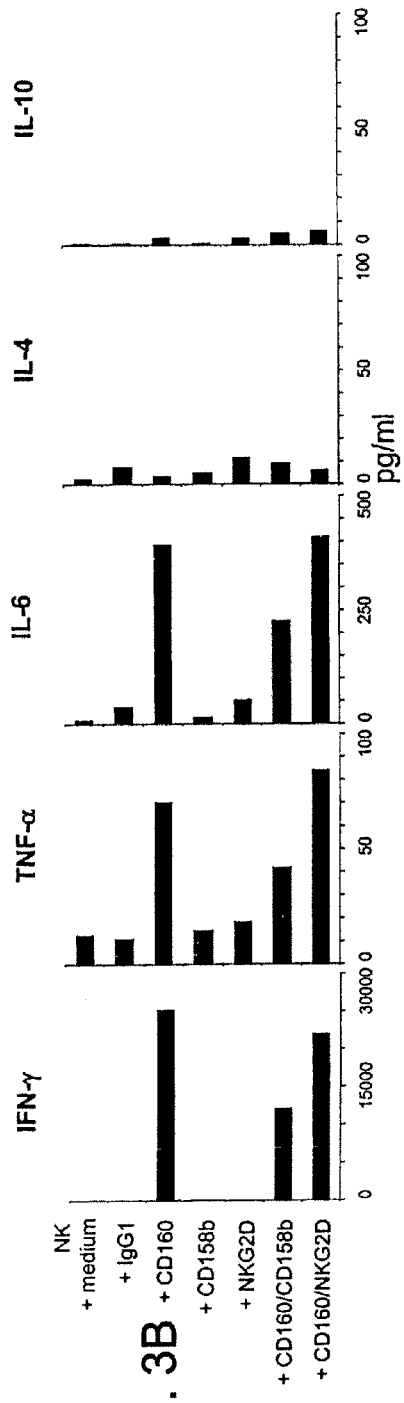

Masking HLA-C ligand or CD160 receptor by their specific mAbs significantly diminished the IFN-γ, TNF-α and IL-6 production. These results show that this PB-NK cytokine production is mainly attributable to CD160-HLA-C interaction. However, for an unknown reason, the use of W6/32 anti-HLA-C mAb did not significantly inhibit IL-6 secretion.
Antibody Cross-Linking of CD160 Expressed by Cytotoxic PB-NK Triggers a Unique Cytokine Production Profile Different from the One Obtained after CD16 or NKG2D Engagement We then compared the cytokines produced by CD160 triggering with the CD16 activating receptor whose expression is also restricted to the cytotoxic NK cell subset. The activating natural cytotoxic receptors (NCR) and 2B4/CD244 co-receptor were excluded from this comparison as they are equally distributed on both cytotoxic and non-cytotoxic PB-NK lymphocytes (Ferlazzo, G., and C. Münz. 2004. NK cell compartments and their activation by dendritic cells. J. Immunol. 172:1333-1339). NKG2D activating receptor triggering was used as negative control for its inability to mediate cytokine production by itself in human NK cells (André, P., R. Castriconi, M. Espeli, N. Anfossi, T. Juarez, S. Hue, H. Conway, F. Romagne, A. Dondero, M. Nanni, S. Caillat-Zucman, D. H. Raulet, C. Bottino, E. Vivier, A. Moretta, and P. Paul. 2004. Comparative analysis of human NK cell activation induced by NKG2D and natural cytotoxicity receptors. Eur. J. Immunol. 34:961-971; Raulet, D. H. 2003. Roles of the NKG2D immunoreceptor and its ligands. Nat. Rev. Immunol. 3:781-790). The results indicate that CD160-mAb cross-linking leads PB-NK to produce the same pattern of cytokine release, namely high levels of IFN-γ, and lower amounts of TNF-α and IL-6, but no IL-4 nor IL-10 (FIG. 2), than the HLA-C physiological ligand triggering (Table I). The use of an isotype-matched control Ig did not lead to such secretion. Next, we analyzed the cytokine production after cross-linking of CD16 receptor with the specific 3G8 mAb. This triggered both IFN-γ and TNF-α production but no IL-6 (FIG. 2). Importantly, whereas the amount of TNF-α was comparable after CD160 or CD16 engagement, the production of IFN-γ mediated by CD16 cross-linking was ~30 fold less than the secretion obtained after CD160 engagement. As expected, Ab cross-linking of NKG2D did not trigger significant cytokine production. These data further demonstrate that Ab cross-linking of CD160 receptor on cytotoxic PB-NK cells results in a unique cytokine profile similar to that observed after interaction with HLA-C physiological ligand. It should be of note that IL-6 production by a cytotoxic NK cell subset, upon triggering of activating receptors, has not been reported yet. IL-6 is a multifunctional cytokine that acts in the immune system and a recent report has shown that some tumor-infiltrating lymphocytes produced high concentrations of IL-6, blocking the anti-LAK activity of tumor cell TGF-β1 (Hsiao, Y. W., K. W. Liao, S. W. Hung, and R. M. Chu. 2004. Tumor-Infiltrating Lymphocyte Secretion of IL-6 Antagonizes Tumor-Derived TGF-beta1 and Restores the Lymphokine-Activated Killing Activity. J. Immunol. 172:1508-1514).
Inhibition of CD160-Mediated NK Cell Cytokine Production by CD158b Inhibitory Receptor Activation of NK cells is dependent on activating receptors that are normally functionally silenced by inhibitory receptors, including the killer immunoglobulin-like receptors (KIRs) that recognize different allelic groups of HLA-A, -B or -C molecules. We previously reported that cytotoxic activity triggered upon CD160 engagement was inhibited by the co-engagement of CD158b inhibitory receptor (Le Bouteiller, P., A. Barakonyi, J. Giustiniani, F. Lenfant, A. Marie-Cardine, M. Aguerre-Girr, M. Rabot, I. Hilgert, F. Mami-Chouaib, J. Tabiasco, L. Boumsell, and A. Bensussan. 2002. Engagement of CD160 receptor by HLA-C is a triggering mechanism used by circulating natural killer (NK) cells to mediate cytotoxicity. Proc. Natl. Acad. Sci. USA 99:16963-16968). We thus investigated whether inhibitory receptors also controlled CD160-mediated cytokine production. We used PB-NK from donors who express variable percentages of cell population bearing CD158b inhibitory receptor. We analyzed cell surface expression of CD160, as well as CD158b, NKG2D and other NK cell markers by flow cytometry on freshly isolated, purified PB-NK. FIG. 3A shows the results obtained with one representative donor. A major subset of PB-NK expresses CD160, whereas all of them are CD56$^+$, CD3$^-$, and CD16$^+$ (FIG. 3A, upper panel). Whereas the whole PB-NK population is NKG2D$^+$, only a subset expresses CD158b inhibitory receptor. Double staining confirms that CD160$^+$PB-NK were CD3$^-$, and mostly CD56$^{dim}$ and CD16$^+$ (FIG. 3A, lower panel). In addition, we found that only subpopulations of CD160$^+$ cells also expressed CD158b or NKG2D (FIG. 3A, lower panel). As expected, we found that mAb-mediated cross-linking of CD160 and not of NKG2D receptor led to the production of IFN-γ, TNF-α, and IL-6 and that, the co-cross-linking of both CD158b inhibitory receptor and CD160 reduced significantly the cytokine production (FIG. 3B). Such a reduction did not occur when an isotype-matched control Ab substituted CD158b mAb. Similar results were obtained with five different PB-NK donors that contained variable percentages (~8-30%) of CD158b$^+$NK subset among the purified PB-NK cells. As only a sub-population of PB-NK did express CD158b, it may explain why the down-modulation of cytokine secretion was only partial in our experiments. One can speculate that other KIRs, which interact with different HLA alleles, may also contribute to such control of CD160 inducing cytokine production and thus participate to NK cell tolerance in normal physiological situation. We also examined whether NKG2D co-engagement could synergize with CD160 to produce an augmented stimulatory signal. We found that simultaneous cross-linking of NKG2D, whose level is up-regulated following IL-2 activation, and CD160 activating receptors did not induce a cumulative positive signal compared with stimulation through the CD160 receptor alone (FIG. 3B). This confirms previous results showing that human NKG2D triggering by specific mAb cross-linking did not induce activation of cytokine secretion (André, P., R. Castriconi, M. Espeli, N. Anfossi, T. Juarez, S. Hue, H. Conway, F. Romagne, A. Dondero, M. Nanni, S. Caillat-Zucman, D. H. Raulet, C. Bottino, E. Vivier, A. Moretta, and P. Paul. 2004. Comparative analysis of human NK cell activation induced by NKG2D and natural cytotoxicity receptors. Eur. J. Immunol. 34:961-971). However, stimulation of polyclonal activated NK cells with plastic-bound recombinant MICA or ULBP physiological ligands could trigger GM-CSF and IFN-γ production (André, P., R. Castriconi, M. Espeli, N. Anfossi, T. Juarez, S. Hue, H. Conway, F. Romagne, A. Dondero, M. Nanni, S. Caillat-Zucman, D. H. Raulet, C. Bottino, E. Vivier, A. Moretta, and P. Paul. 2004. Comparative analysis of human NK cell activation induced by NKG2D and natural cytotoxicity receptors. Eur. J. Immunol. 34:961-971).

CD160 receptor, whose expression is restricted to the effector cytotoxic $CD56^{dim}$ $CD16^{bright}$ PB-NK cell subset, appears as a unique MHC class I-dependent activating receptor capable to promote cytokine secretion upon specific ligation. Firstly, HLA-C major ligand of CD160 is constitutively expressed, which differs from the inducible self-ligands or pathogens induced ligands of the other NK triggering receptors expressed on both cytotoxic and non-cytotoxic NK lymphocyte subsets. Human NKG2D ligands are the stress-induced MICA and MICB molecules that are expressed predominantly by cells of epithelial origin or pathogen encoded ULBP (Raulet, D. H. 2003. Roles of the NKG2D immunoreceptor and its ligands. Nat. Rev. Immunol. 3:781-790). In addition, NKG2D is unable to trigger by itself IFN-γ production in human (Carayannopoulos, L., and W. Yokoyama. 2004. Recognition of infected cells by natural killer cells. Curr. Opin. Immunol. 16:26-33). The recently described Poliovirus receptor (CD155) and Nectin-2 (CD112) ligands of the DNAM-1 co-activating receptor are also mostly expressed in stressed tissues (Moretta, L., and A. Moretta. 2004. Unravelling natural killer cell function: triggering and inhibitory human NK receptors. Embo J. 23:255-259). NCR ligands are non-MHC molecules, including SV hemaglutinin-neuraminidase for NKp44 and NKp46 (Carayannopoulos, L., and W. Yokoyama. 2004. Recognition of infected cells by natural killer cells. Curr. Opin. Immunol. 16:26-33). In contrast to the above-mentioned receptors, CD16 is present only on effector cytotoxic PB-NK lymphocyte subset and its ligand is the Fc portion of IgG. Secondly, stimulatory KIRs and CD94/NKG2C activating receptor that are only expressed by a subset of cytotoxic PB-NK lymphocytes, also interact with constitutive HLA class I molecules, including HLA-C for the former, have short cytoplasmic domains with no known signaling motif (Cerwenka, A., and L. Lanier. 2001. Natural Killer cells, viruses and cancer. Nat. Rev. Immunol. 1:41-49). In addition, these activating receptors associate with adaptor molecules to initiate signaling (Lanier, L. 2003. Natural killer cell receptor signaling. Curr. Opin. Immunol. 15:308-314), which differs from CD160 GPI-anchored cell surface molecule (Le Bouteiller, P., A. Barakonyi, J. Giustiniani, F. Lenfant, A. Marie-Cardine, M. Aguerre-Girr, M. Rabot, I. Hilgert, F. Mami-Chouaib, J. Tabiasco, L. Boumsell, and A. Bensussan. 2002. Engagement of CD160 receptor by HLA-C is a triggering mechanism used by circulating natural killer (NK) cells to mediate cytotoxicity. Proc. Natl. Acad. Sci. USA 99:16963-16968). 2B4/CD244 is an NK cell receptor that provides a co-stimulatory signal to other activation receptors including NCR or NKG2D (Moretta, L., M. Mingari, C. Bottino, D. Pende, R. Biassoni, and A. Moretta. 2003. Cellular and molecular basis of natural killer and natural killer-like activity. Immunol. Letters 88:89-93).

Data from this study shows that stimulation of CD160 receptor on NK cells may lead to enhancement of both innate immunity (through specific cell killing) and adaptive immunity (through cytokine secretion). Strikingly, it has been shown that the HLA-C ligand of CD160 is protected from degradation or endocytosis mediated by US2 or US11 CMV-derived proteins (Tortorella, D., B. Gewurz, M. Furman, D. Schust, and H. Ploegh. 2000. Viral subversion of the immune system. Ann. Rev. Immunol. 18:861-926) or Nef HIV-1 proteins (Cohen, G., R. Gandhi, D. Davis, O. Mandelboim, B. Chen, J. Strominger, and D. Baltimore. 1999. The selective downregulation of class I Major Histocompatibility Complex proteins by HIV-1 protects HIV-infected cells from NK cells. Immunity 10:661-671), respectively. This suggests that CD160 may still be functional soon after viral infection.

The signals that transform a circulating resting NK cell into an activated cytokine-secreting cell in vivo are not fully understood. This mainly depends on the outcome of signals derived from activating and inhibitory receptors upon engagement by their specific ligands. Knowing that CD158a/CD158b inhibitory receptors engage HLA-C molecules on target cells, we hypothesize that the level of expression of HLA-C may be a key factor to trigger either the KIR or CD160 receptors. When the level of HLA-C is normal, KIR inhibitor receptor engagement would control CD160. In contrast, when the level of expression of HLA-C is down modulated, KIR receptors might no longer be efficiently engaged, allowing the activating function of CD160 receptor to take place.

In conclusion, this study demonstrates that functional activation of CD160 NK cell receptor by HLA-C physiological ligand initiates both cytotoxicity and cytokine production after optimal receptor triggering. The present results strongly suggest that CD160 mediates the activating effector functions through a unique signaling pathway to limit viremia and tumor burden or pathogen-infected cells.

Example 2

Cutting Edge: Soluble HLA-G1 Inhibits Angiogenesis Through the Binding to CD160 Receptor Expressed by Endothelial Cells Material and Methods
Cells and Reagents HUVEC and human microvascular endothelial cells (HMVEC) [HUVEC CC-2517, and neonatal HMVEC-C (CC-2505); Cambrex Bio Science, Walkersville, Maryland, U.S.A.] were maintained in EBM (BioWhittaker) supplemented with 5% FCS and 1 ng/ml VEGF or FGF-2 (R & D systems, Minneapolis, IL) every other day.

Human Jurkat T cells are available from ATCC Number TIB 152.

Jurkat cells transfected with CD160 (Jurkat-CD160) were produced by transfection of CD160 in Jurkat cells as reported by Anumantha, A., A. Bensussan, L. Boumsell, A. Christ, R. Blumberg, S. Voss, A. Patel, M. Robertson, L. Nadler, and G. Freeman, 1998 ("Cloning of BY55, a novel Ig superfamily member expressed on NK cells, CTL, and intestinal intraepithelial lymphocytes", Journal of Immunology 161:2780.) NK92 is a human NK cell line expressing CD160 (ATCC Number CRL-2407). CD4+ T cells were purified from PBMC using the MACS separation system (Miltenyi Biotec, Auburn, Calif.). The sHLA-G1-β2m fusion monochain gene was engineered by connecting the last residue of the α3 domain of HLA-G to the first codon of the human β2m sequence through a 15-residue spacer (Fournel, S., M. Aguerre-Girr, A. Campan, L. Salauze, A. Berrebi, Y. Lone, F. Lenfant, and P. Le Bouteiller. 1999. Soluble HLA-G: purification from eucaryotic transfected cells and detection by a specific ELISA. American Journal of Reproductive Immunology 42:22). sHLA-G1 and sHLA-G1mono were purified from eucaryotic cell culture supernatants, using immunoaffinity columns, as previously described (Fournel, S., M. Aguerre-Girr, A. Campan, L. Salauze, A. Berrebi, Y. Lone, F. Lenfant, and P. Le Bouteiller. 1999. Soluble HLA-G: purification from eucaryotic transfected cells and detection by a specific ELISA. American Journal of Reproductive Immunology 42:22). VEGF 165 was expressed in a baculovirus system as described (Plouët, J., F. Moro, S. Bertagnolli, N. Coldeboeuf, H. Mazarguil, S. Clamens, and F. Bayard. 1997. Extracellular cleavage of the vascular endothelial growth factor 189-amino acid form by urokinase is required for its mitogenic effect. J Biol Chem 272:13390). mAbs used included:

CL1-R2 (anti-CD160 IgG1; hybridoma TM60 available from C.N.C.M. Institut Pasteur 25, rue du Docteur Roux F-75724 PARIS CEDEX 15 FRANCE under C.N.C.M. deposit number=I-3204), anti-CD8 (B9.11, Coulter Immunotech, Marseille, France), anti-CD85j (BD Biosciences Pharmingen, San Diego, Calif., USA), anti-CD106 (1G11 Coulter-Immunotech), dialyzed mouse IgG1 or IgG2a isotype controls (Coulter-Immunotech).

HLA-G tetramers were produced essentially as previously described (Allan, D. S., M. Colonna, L. L. Lanier, T. D. Churakova, J. S. Abrams, S. A. Ellis, A. J. McMichael, and V. M. Braud. 1999. Tetrameric complexes of human histocompatibility leukocyte antigen (HLA)-G bind to peripheral blood myelomonocytic cells. J Exp Med 189:1149), using synthetic self-peptide RIIPRHLQL (SEQ ID NO:7) and after addition of streptavidin-PE (Pharmingen) (Lee, N., A. R. Malacko, A. Ishitani, M. C. Chen, J. Bajorath, H. Marquardt, and D. E. Geraghty. 1995. The membrane-bound and soluble forms of HLA-G bind identical sets of endogenous peptides but differ with respect to TAP association. Immunity 3:591). Labeling of HUVEC, Jurkat and Jurkat-CD160 by PE-conjugated HLA-G tetramers was performed at 37° C. for 1 h. For Jurkat-CD160 and Jurkat, tetramers were cross-linked with anti-class HLA class I W6/32 mAb.

Lewis lung carcinoma cells are available from ECACC [European Collection of Cell Cultures; Health Protection Agency; Porton Down; SP4 0JG Salisbury, Wiltshire UK] (human Caucasian lung carcinoma cell line COR-L23/R; deposit number ECACC 96042339).

Cell Proliferation and Migration Assays

For the proliferation analysis, HUVEC ($8 \times 10^3$) were seeded in 12-well plates coated with 0.3% gelatin. Cells were incubated with saline or VEGF (1 ng/ml) in the presence of absence of various concentrations of sHLA-G1 or sHLA-G1mono. 7 days later, cells were trypsinized and counted in a Coulter counter ZM (Margency, France). Migration assays were performed on growth arrested confluent HUVEC or BAEC. Cell monolayers were wounded with a rubber policeman. The dishes were washed with serum-free medium and each well was photographed at 100× magnification. Dishes were then incubated for 16 h in serum free medium containing of sHLA-G1 or sHLA-G1mono (100 ng/ml) in the presence or not of VEGF (50 ng/ml). A second photograph of each well was taken and the cells which had migrated were counted by superposing the two photographs.

Cell Binding of VEGF and sHLA-G1

VEGF and sHLA-G1 were iodinated with the iodogen procedure with a specific activity of 240,000 and 110,000 cpm/ng, respectively (Plouët, J., F. Moro, S. Bertagnolli, N. Coldeboeuf, H. Mazarguil, S. Clamens, and F. Bayard. 1997. Extracellular cleavage of the vascular endothelial growth factor 189-amino acid form by urokinase is required for its mitogenic effect. J Biol Chem 272:13390). Wells containing $2 \times 10^5$ serum-starved HUVEC were either pre-treated with 50 ng/ml VEGF or sHLA-G1 at 37° C. for various time intervals (0.1-24 h) or processed immediately for binding assays. Briefly dishes were rinsed in cold DMEM supplemented with 0.2% gelatin and 20 mM Hepes pH 7.3 and incubated at 4° C. for 2 h with 2 ng/ml $^{125}$I-VEGF or sHLA-G1 in the absence or presence of unlabeled ligand. Cells were then rinsed in the same medium and lysed in RIPA buffer and the radioactivity counted in a Packard gamma counter.

In Vitro Capillary Tube Formation

Growth factor reduced Matrigel (BD Biosciences) was diluted in collagen (1/6 v/v) and kept on ice. 160 µl of this solution was added to each well of 8-well culture slides pre-coated with type I rat tail collagen and left at 37° C. for 1 h. Following gel formation, a HUVEC suspension, mixed or not with control, FGF-2, sHLA-G1 or mAb CD160 was seeded on Matrigel/collagen gels for 24 h at 37° C. in a humidified 5% CO2 incubator. Angiogenesis was quantified as previously described (Ruggeri B, Singh J, Gingrich D, Angeles T, Albom M, Yang S, Chang H, Robinson C, Hunter K, Dobrzanski P, Jones-Bolin S, Pritchard S, Aimone L, Klein-Szanto A, Herbert J M, Bono F, Schaeffer P, Casellas P, Bourie B, Pili R, Isaacs J, Ator M, Hudkins R, Vaught J, Mallamo J, Dionne C. "CEP-7055: a novel, orally active pan inhibitor of vascular endothelial growth factor receptor tyrosine kinases with potent antiangiogenic activity and antitumor efficacy in preclinical models", Cancer Res. 2003 Sep. 15; 63(18):5978-91; Erratum in: Cancer Res. 2003 Nov. 1; 63(21):7543.

Briefly, the culture medium was removed, cells rinsed twice with PBS and fixed for 30 min at room temperature in a 4% PFA solution. Then, the cells were washed twice with PBS and stained with Masson's Trichrom stain. The extent of the microcapillary network was measured using an automated computer-assisted image analysis system (Imagenia, Biocom, Les Ulis, France), and the total length of the capillaries in each well was determined. The mean microcapillary network length (µm) was calculated for each experimental condition. Experiments were performed in triplicate and repeated 3 times.

Flow Cytometry Analysis

Subconfluent HMVEC in normoxia or in hypoxia (24 hours incubated at 37° C. in a 5% O2 atmosphere) or HUVEC (Biowitthaker) were scrapped in PBS-BSA and incubated or not with 100 ng/ml of sHLA-G1 at 4° C. After 2 h cells were incubated with either CD8, CD85d, CD85j (Plouët, J., F. Moro, S. Bertagnolli, N. Coldeboeuf, H. Mazarguil, S. Clamens, and F. Bayard. 1997. Extracellular cleavage of the vascular endothelial growth factor 189-amino acid form by urokinase is required for its mitogenic effect. J Biol Chem 272:13390.1), CD106 (BD), CL1-R2 BY55 (Fournel, S., M. Aguerre-Girr, A. Campan, L. Salauze, A. Berrebi, Y. Lone, F. Lenfant, and P. Le Bouteiller. 1999. Soluble HLA-G: purification from eucaryotic transfected cells and detection by a specific ELISA. American Journal of Reproductive Immunology 42:22) specific mAbs or isotypic control Abs 20 μg/ml followed by F(ab')2-FITC conjugated goat anti-mouse IgG. Non viable cells were excluded by the use of propidium iodide. Cells were analyzed by a Coulter-Epics ELITE flow cytometer.

RT-PCR and cDNA Sequencing

CD160 transcripts were detected by RT-PCR using the following primers: 5'-3' (sense) TGCAGGATGCTGTTGGAACCC (SEQ ID NO:1) and 3'-5' (reverse) TCAGCCTGAACTGAGAGTGCCTTC (SEQ ID NO:2; cDNA quality was confirmed by amplification of β actin using the following primers: 5'-3'GCGGGAAATCGTGCGTGCGTGACA (SEQ ID NO:3) and 3'-5' GATGGAGTTGAAGGTAGTTTCGTG (SEQ ID NO:4). Amplification conditions for CD160 and β-actin were 95° C. for 45 s, 60° C. 30 s, and 72° C. for 1 min, for 35 cycles. For CD160 sequencing, a Taq High Fidelity was used (Invitrogen). PCR product was purified (qiaex II, Qiagen) and analyzed with the following primers: BY01 (5'-3' sense) (TGCAGGATGCTGTTGGAACCC; SEQ ID NO:1), BY03 (3'-5' reverse) (TCAGCCTGAACTGAGAGTGCCTTC; SEQ ID NO:2; BY02 (5'-3' sense) CAGCTGAGACTTAAAAGGGATC; SEQ ID NO:5) and BY04 (3'-5' reverse) (CACCAACACCATCTATCCCAG; SEQ ID NO:6).

Syngenic Tumor for Histological Studies

Sub-confluent Lewis lung carcinoma cells were trypsinized, washed twice and resuspended in PBS. $2.10^5$ cells were inoculated subcutaneously into the right posterior lateral flank of anaesthetised (pentobarbital, IP) female C57B16 mice (IFFA CREDO, France). Mice were killed 21 days after cell injection with an overdose of pentobarbital; tumors were removed and fixed in 10% neutral buffered formalin (Sigma) overnight at 4° C., paraffin embedded (Embedder Leica) and then sectioned (5 μm) with a microtome (Leica). After rehydration (toluene/ethanol/PBS), slides were heated for 20 min in a citrate buffer solution at pH 6.1. Sections were placed in a DAKO Autostainer and incubated with TNB Blocking buffer (TSA Kit, NEN), peroxidase-blocking reagent (Dako) and Mouse on Mouse immunoglobulin blocking reagent (Vector Laboratories). Tumours vessels were stained with the monoclonal antibody CL1-R2 at a final concentration of 10 μg/ml (Dilution 1/500 de la solution) during 30 min at room temperature. Sections were then incubated with biotin-labelled goat anti-rabbit IgG for 10 min followed by incubation with Avidin-Biotin Complex (Vector Laboratories) for 30 min. Sections were then stained with DAB (Vector Laboratories) and counterstained with hematoxylin. Immunostained tissues were viewed on a Nikon microscope (E-800) and digitised using a DMX 1200 camera (Nikon) with 40× objective.

Results sHLA-G1 Inhibits VEGF- or FGF2-Induced Endothelial Cell Proliferation, Migration and Capillary-Like Tube Formation VEGF is the more potent mitogenic and motogenic factor for vascular EC. Therefore we investigated whether sHLA-G1 could interfere with VEGF functions on EC in vitro. We found that sHLA-G1 inhibited VEGF-induced proliferation of HUVEC (FIG. 4A) whereas it did not affect basal proliferation of these cells. In contrast, when sHLA-G1 was fused to β2m, the single chain protein did not affect the proliferation of EC induced by VEGF, therefore suggesting that folding of the molecule was critical for its biological activity. Moreover, sHLA-G1 inhibited VEGF-induced proliferation of bovine EC derived from aorta or adrenal gland microvessels, suggesting a mechanism conserved among species and organ of origin of the EC.

Figure 4:
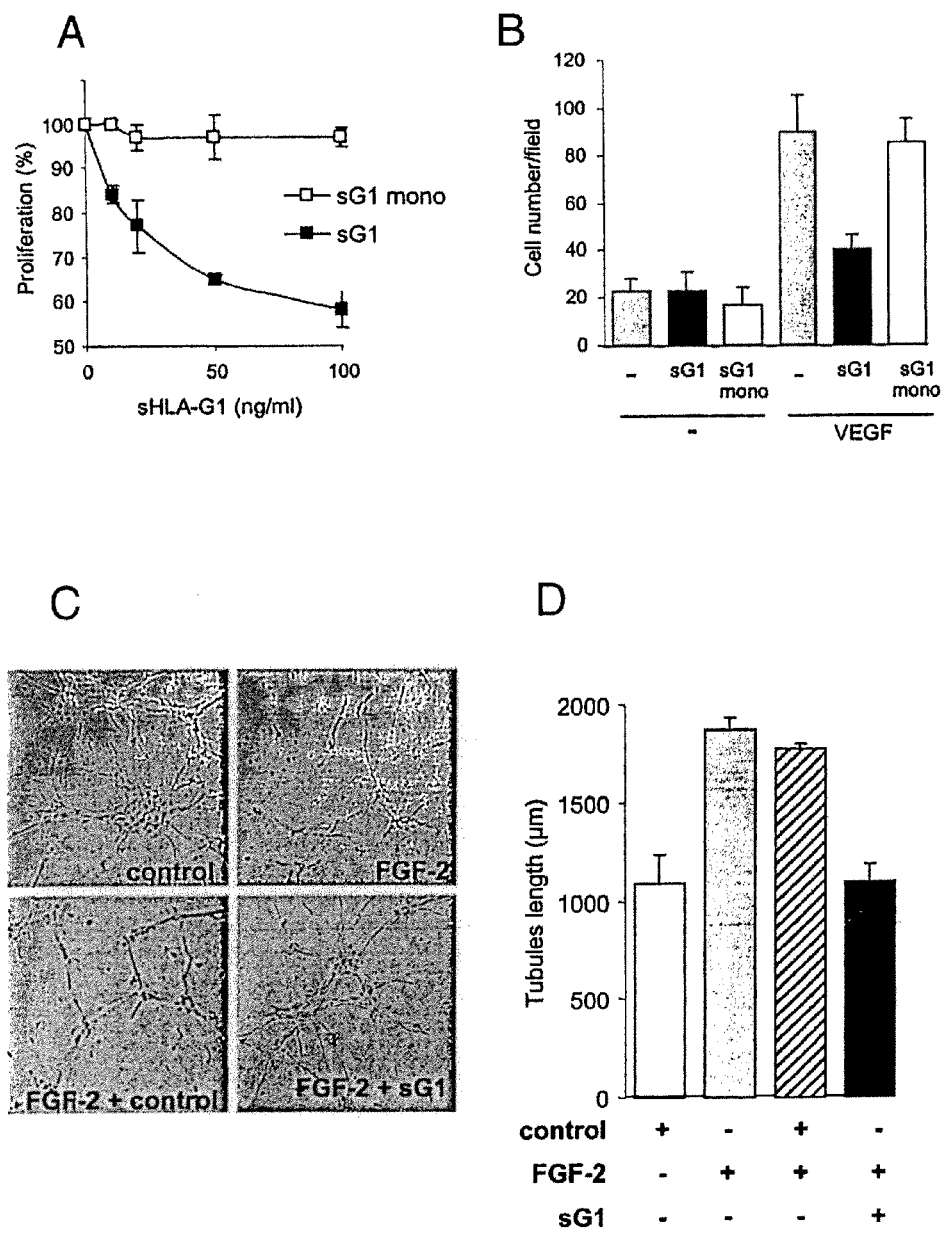
FIGS. 4A, 4B, 4C, 4D. Effect of sHLA-G1 on VEGF or FGF2-induced EC proliferation, migration and capillary-like tube formation.
Figure 5:
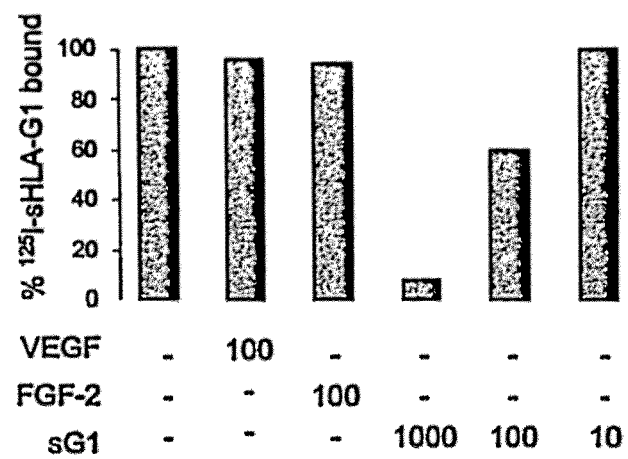
FIGS. 5A, 5B. sHLA-G1 does not bind to VEGF receptors.
Figure 5:
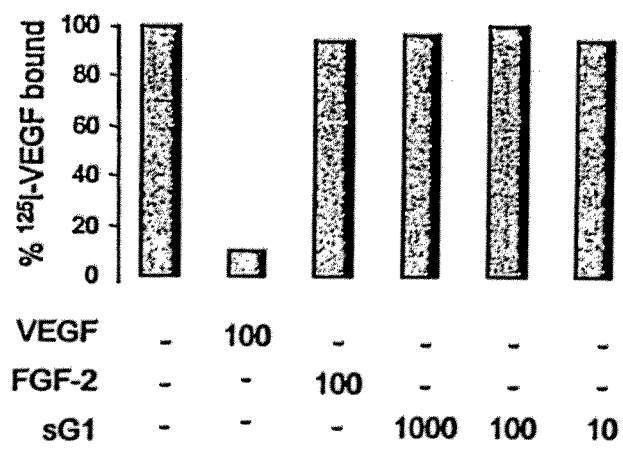

In a migration assay using HUVEC as endothelial cell model no migration occurred whether or not sHLA-G1 or sHLA-G1mono were added in the absence of VEGF (FIG. 4B). In contrast, after addition of VEGF, a significant increase in the number of migrated cells was detected. In these conditions, addition of sHLA-G1 inhibited migration, whereas sHLA-G1 mono had no significant effect (FIG. 4B). To evaluate whether sHLA-G1 was able to block tube formation after stimulation by pro angiogenic factors, HUVEC were subjected to FGF-2 in the Matrigel model. For this purpose, the Matrigel was diluted with collagen to limit spontaneous angiogenesis which normally occurs after 3 days in culture. Morphology of the cells in Matrigel is shown in FIG. 4C and the quantification of the total tubules length is shown in FIG. 4D. The results indicate that FGF-2 induced a potent angiogenic response and that addition of sHLA-G1 to FGF-2 significantly inhibited tube formation.

Altogether, these results demonstrate that sHLA-G1 is able to inhibit pro-angiogenic factor-induced EC proliferation, migration and in vitro vessel formation.

sHLA-G1 did not Interfere with VEGF Receptors

In this study, both $^{125}$I-VEGF and $^{125}$I-sHLA-G1 were used as ligands. Total binding of radiolabelled ligands to HUVECs cells at 4° C. was time dependent and reached equilibrium 45 min after the beginning of the experiment. After 60 min, incubation with unlabelled ligand almost totally dissociated $^{125}$I-VEGF or $^{125}$I-sHLA-G1 binding from the endothelial cells. Thus, equilibrium binding experiments were performed by setting the incubation time at 60 min. Whatever the radio-ligand used, total binding was dose-dependent and non-specific binding, measured in the presence of a high concentration of unlabelled ligands, was linear with the concentration of radioligand. The non-specific binding did not exceed 20% of the total binding. In competition experiments using $^{125}$I-sHLA-G1 as ligand, while sHLA-G1 rapidly displaced the binding to HUVEC with IC50 values in a nanomolar range, VEGF preincubated or not with the cells did not affect this binding (FIG. 2A). In competition experiments using now $^{125}$I-VEGF as ligand, while VEGF rapidly displaced the binding of $^{125}$I-VEGF to HUVEC with IC50 values in a nanomolar range, sHLA-G1 pre-incubated or not with the cells did not affect this binding (FIG. 2B). These results demonstrate that sHLA-G1 was able to bind specifically to endothelial cells and that this binding was not modulate by VEGF. Moreover we clearly demonstrates that sHLA-G1 did not interfere with the VEGF receptors on endothelial cells.

CD160 Receptor is Expressed by Endothelial Cells

Using specific mAbs and flow cytometry analysis, we found that HUVEC did not express CD8, nor CD85j. In contrast, these cells were strongly stained by an anti-CD160 mAb (FIG. 6A) like HMVEC. To provide additional evidence that CD160 was expressed by HUVEC, we performed RT-PCR analysis on these cells by comparison to CD160$^+$ (NK92) and CD160$^-$ (CD4$^+$ T) control cells, using CD160 specific primers. Similarly to NK92, CD160 mRNA was detected in HUVEC, whereas CD4$^+$ T cells were negative (FIG. 6B). Then HUVEC and NK92 cDNAs were isolated and sequenced. Predicted amino acid sequence alignment of HUVEC and NK92 CD160 proteins showed that they were both similar to the CD160 sequence already described (Anumantha, A., A. Bensussan, L. Boumsell, A. Christ, R. Blumberg, S. Voss, A. Patel, M. Robertson, L. Nadler, and G. Freeman. 1998. Cloning of BY55, a novel Ig superfamily member expressed on NK cells, CTL, and intestinal intraepithelial lymphocytes. Journal of Immunology 161:2780) (FIG. 6C). Altogether these data demonstrate that CD160 was expressed by EC.

sHLA-G1 Interacts with CD160 Expressed at the Cell Surface of HUVEC

Figure 7A:
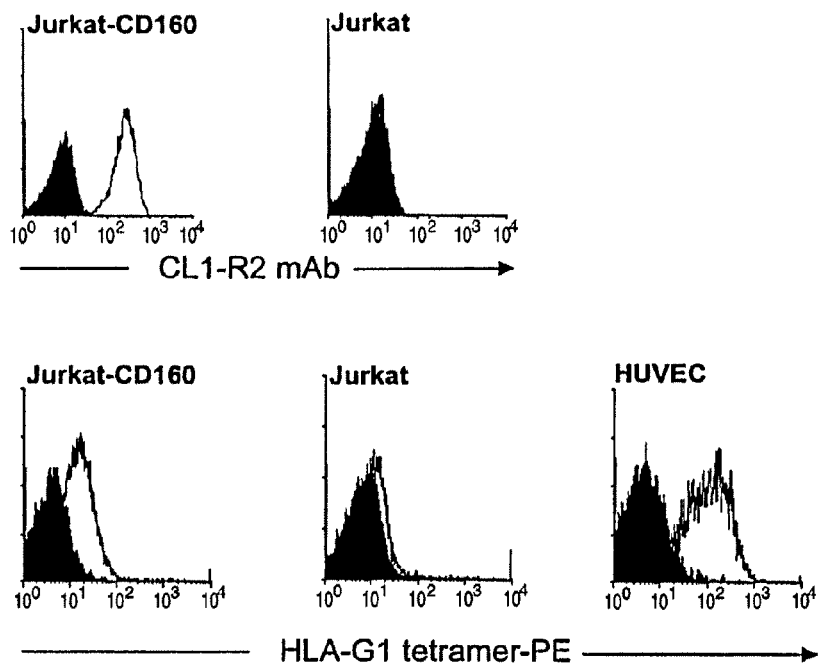
FIGS. 7A, 7B. HLA-G tetramers bind to Jurkat-CD160 and HUVEC.
Figure 7B:
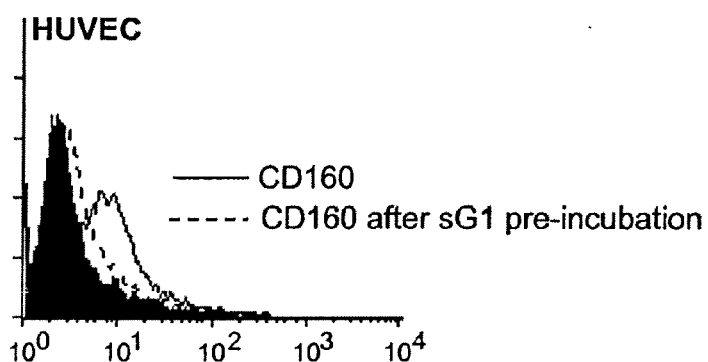
Figure 8:
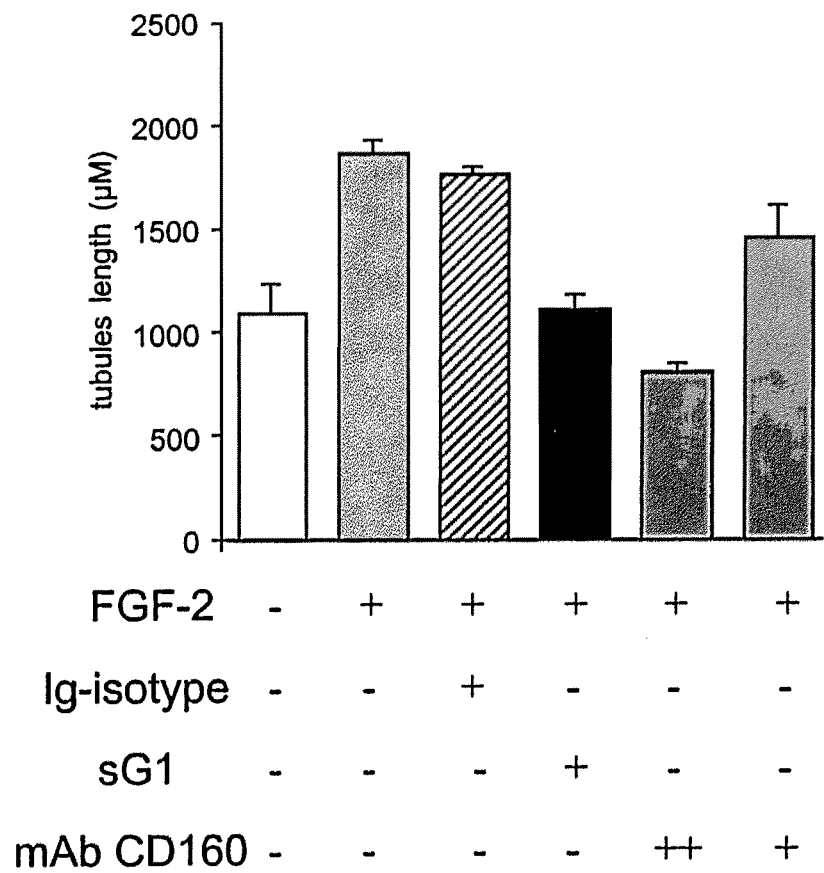
FIG. 8. mAb cross-linking of CD160 triggers inhibition of in vitro angiogenesis.

Having shown that CD160 was present on EC, we investigated whether sHLA-G1 could be a potential ligand. The direct interaction of CD160 with sHLA-G1 on HUVEC was demonstrated by using HLA-G1 tetramers. We first showed that these tetramers specifically bound to Jurkat-CD160, but not to untransfected Jurkat (FIG. 7A), demonstrating the specificity of CD160 for sHLA-G1 ligand. When HUVEC were incubated with HLA-G1 tetramers, a clear staining was detected, suggesting that sHLA-G1 bound to CD160 expressed by this cell (FIG. 7A). CD160-sHLA-G1 interaction was further evaluated by flow cytometry on HUVEC which were pre-incubated or not with sHLA-G1. We found that pre-incubation of HUVEC with sHLA-G1 down-modulated CD160 cell surface expression (FIG. 7B). This demonstrates that sHLA-G1 directly interacts with CD160 at the cell surface of HUVEC.

mAb Cross-Linking of CD160 Expressed by Endothelial Cells Triggers Inhibition of Capillary-Like Tube Formation Next, we investigated whether CD160-mAb cross-linking could mimic the sHLA-G1 anti-angiogenic activity. Using the in vitro Matrigelassay, we found that CD160-mAb cross-linking leads to the inhibition of FGF2-mediated tubule vessel growth (FIG. 8). These data further demonstrated that CD160, expressed by EC was a functional receptor able to trigger an anti-angiogenic cell response.

Hypoxia Induced an Increase in the Expression of CD160 on Endothelial Cells

While many of the individual phenotypic process in angiogenesis such as cell migration or endothelial tube formation can be induced by hypoxic culture conditions, we determined the expression of CD160 in HMVEC cultured under hypoxic conditions (Luttun, A., M. Autiero, M. Tjwa, and P. Carmeliet. 2004. Genetic dissection of tumor angiogenesis: are P1GF and VEGFR-1 novel anti-cancer targets? Biochim Biophys Acta 1654:79). Using specific CD160 mAb and flow cytometry analysis, we found that hypoxia strongly increased CD160 expression on endothelial cells (FIG. 9).

Immunohistochemical Staining of LLC Tumors Demonstrate that Only EC Expressed CD160 in the Tumor Finally, we observed a strong staining for CD160 on EC in LLC tumors (FIGS. 10A, 10B, 10C, 10D) whereas no staining was observed with non-specific IgG. Tumors cells did not express CD160 but EC of lymphatic vessels at the periphery of the tumor or microvessels inside the tumors express a high level of CD160.

Discussion

In this study, we identified a new receptor, CD160, able to trigger an anti-angiogenic response in endothelial cells. We demonstrated, for the first time, that this MHC class I-dependent receptor is expressed by EC.

CD160 triggers inhibition of VEGF- or FGF-2-induced in vitro angiogenesis upon engagement with its physiological ligand, sHLA-G1, or following specific mAb cross-linking (CL1-R2).

CD160 differs from the previously described CD36 receptor, a transmembrane glycoprotein bound by thrombospondin 1 (TSP-1), a potent inhibitor of angiogenesis (Dawson, D. W., S. F. Pearce, R. Zhong, R. L. Silverstein, W. A. Frazier, and N. P. Bouck. 1997. CD36 mediates the In vitro inhibitory effects of thrombospondin-1 on endothelial cells. J Cell Biol 138: 707). In contrast to CD36, CD160 is a GPI-anchored molecule having no transmembrane domain, nor cytoplasmic tail (Anumantha, A., A. Bensussan, L. Boumsell, A. Christ, R. Blumberg, S. Voss, A. Patel, M. Robertson, L. Nadler, and G. Freeman. 1998. Cloning of BY55, a novel Ig superfamily member expressed on NK cells, CTL, and intestinal intraepithelial lymphocytes. Journal of Immunology 161:2780).

We further found that sHLA-G1 was an EC CD160 ligand. Knowing that various HLA class I molecules may bind to CD160 (Le Bouteiller, P., A. Barakonyi, J. Giustiniani, F. Lenfant, A. Marie-Cardine, M. Aguerre-Girr, M. Rabot, I. Hilgert, F. Mami-Chouaib, J. Tabiasco, L. Boumsell, and A. Bensussan. 2002. Engagement of CD160 receptor by HLA-C is a triggering mechanism used by circulating natural killer (NK) cells to mediate cytotoxicity. Proc Natl Acad Sci USA 99:16963; Agrawal, S., J. Marquet, G. J. Freeman, A. Tawab, P. Le Bouteiller, P. Roth, W. Bolton, G. Ogg, L. Boumsell, and A. Bensussan. 1999. Cutting edge: MHC class I triggering by a novel cell surface ligand costimulates proliferation of activated human T cells. J Immunol 162:1223), other soluble MHC class I molecules may also trigger this receptor to exert anti-angiogenic functions. We indeed observed that a recombinant soluble HLA-B7 could also inhibit HUVEC proliferation. These observations suggest that the anti-angiogenic function of sHLA-G1 and sHLA-B7 could be generalized to all soluble HLA.

The anti-angiogenic activity of sHLA-G1 reported here is the first non immune function described to date. Spatial and temporal regulation of angiogenesis at the materno-fetal interface plays an important role in ensuring adequate blood supply to nourish the developing embryo, suggesting that there are local acting factors that regulate vascular growth (Ong, S., G. Lash, and P. N. Baker. 2000. Angiogenesis and placental growth in normal and compromised pregnancies. Baillieres Best Pract Res Clin Obstet Gynaecol 14:969). sHLA-G1 is secreted by extravillous trophoblast, including endovascular trophoblast (Morales, P. J., J. L. Pace, J. S. Platt, T. A. Phillips, K. Morgan, A. T. Fazleabas, and J. S. Hunt. 2003. Placental cell expression of HLA-G2 isoforms is limited to the invasive trophoblast phenotype. J Immunol 171: 6215) that replaces EC of the maternal spiral arteries, thereby increasing by several fold the diameter of these vessels (Loke, Y., and A. King. 2000. Immunology of implantation. Baillière's Clinical Obstetrics Gynaecology 14:827). We hypothesize that sHLA-G1 anti-angiogenic effect might contribute to such replacement. Lack of HLA-G expression in preeclamptic placentas, characterized by a shallow cytotrophoblast invasion and a reduced flow of maternal blood to the feto-placental unit (Lim, K. H., Y. Zhou, M. Janatpour, M. McMaster, K. Bass, S. H. Chun, and S. J. Fisher. 1997. Human cytotrophoblast differentiation/invasion is abnormal in pre-eclampsia. Am J Pathol 151:1809), favors such hypothesis.

Hypoxia has been shown to regulate the expression of multiple angiogenic endothelial markers as CD54, CD105 or tie-2 receptor. Over-expression of tie-2 suggests that it is involved in a positive angiogenic reponse to hypoxia. Up-regulation of CD160 by hypoxia could be generate a negative regulation of angiogenesis and could prevent neovessels formation. Moreover, immunohistochemical on mouse tumor with CD160 antibody shows that this receptor is not expressed by tumor cells themselves but is expressed by EC of the tumoral vasculature. All these results demonstrate that CD160, up-regulated by hypoxia, is an inhibitory signaling receptor for angiogenesis and that its activation may be useful for experimental anti-angiogenic therapy to prevent tumoral cell growth.

Example 3

CD160 is not Restricted to the Cytotoxic T and NK Subset, but is also Expressed by CD4+ T Cells Freshly isolated peripheral blood (PB)-CD4+ cells were obtained from lymphocytes of normal individual using the immunomagnetic CD4 cell isolation kit (Miltenyi Biotec). PB-CD4+ purity was shown to be >98% CD3+CD4+CD8− by flow cytometry. PB-CD4+ were further cultured for several days (between 3 to 6 days) in a standard culture medium containing 10% of heat inactivated human AB serum supplemented with a high concentration of IL-15. The CD160 transcripts were detected by RT-PCR using the following primers:

```
                                       (SEQ ID NO: 8)
5'-3' (sense):    TGCAGGATGCTGTTGGAACCC;

(SEQ ID NO: 9)
3'-5' (reverse):  TCAGCCTGAACTGAGAGTGCCTTC.
```

Illustrative results are shown on FIG. 11.

Example 4

Assessment of Apoptosis by Annexin-V and PI Double-Staining Flow Cytometry

Material and Methods $0.2 \times 10^6$ cells were seeded into a 6 wells/plate, serum-starved for 24 h and then treated with sHLA-G1 (1 µg/ml), CL1-R2 mAb CD160 (10 µg/ml) or control Ig-G1 (10 µg/ml) for 50 h in the presence of VEGF (50 ng/ml). At the end of the treatment, the floating cells were collected by centrifugation, whereas adherent cells were harvested by trypsin-EDTA solution to produce a single cell suspension. The cells were then pelleted by centrifugation and washed twice with PBS. Apoptotic cell death was identified by double staining with recombinant FITC (fluorescein isothiocyanate)-conjugated Annexin-V and PI (propidium iodide), using the Annexin V-FITC Apoptosis Detection kit (DAKO) according to manufacturer's instructions. Cells were analyzed by flow cytometry on a FACScan (Becton Dickinson) using the fluorescence 1 (FL1) signal detector for FITC conjugates and the FL3 signal detector for PI. Teen thousand events were recorded for each sample. The data were analyzed using CellQuest software.

Results

FIG. 18a: demonstrates that CD160 receptor is expressed on the cell surface of HUVEC and HMVEC but not of human fibroblast in primary culture nor smooth muscle cells.

FIG. 18b: demonstrates that CL1-R2 triggers specific apoptosis of HUVEC and not fibroblasts.

FIG. 18c: indicate that the CL1-R2 anti-CD160 monoclonal antibody mimics the anti-angiogenic effect of the soluble HLA-G1 natural ligand of CD160. Both soluble HLA-G1 as well as the anti-CD60 monoclonal antibody mediate endothelial cell (HUVEC) specific apoptosis, the IgG1 isotype control being inefficient. Accordingly, Annexin V binding experiments establish the specificity of this effect: the CL1-R2 monoclonal antibody induces apoptosis of CD160 expressing HUVEC but not of CD160 negative primary fibroblast.

Example 5

Soluble HLA-G1 Inhibits Angiogenesis Through Apoptotic Pathway and by Direct Binding to CD160 Receptor Expressed by Endothelial Cells Abstract HLA-G is a Major Histocompatibility Complex class Ib molecule whose constitutive tissue distribution is mainly restricted to trophoblast cells at the maternal-fetal interface during pregnancy. In this study we demonstrate the ability of soluble HLA-G1 (sHLA-G1) isoform to inhibit vascular endothelial growth factor-induced endothelial cell proliferation and migration, and to decrease fibroblast growth factor-2-induced capillary-like tube formation. We identify potential mechanisms by which this occurs: sHLA-G1 induces apoptosis through binding to CD160, a glycosylphosphatidylinositol-anchored receptor expressed by endothelial cells. Furthermore, we show that the specific CL1-R2 anti-CD160 monoclonal antibody mimics sHLA-G1-mediated inhibition of endothelial cell tube formation and induction of apoptosis. Thus, engagement of CD160 in endothelial cells may be essential for the inhibition of angiogenesis. sHLA-G1/CD160-mediated anti-angiogenic property may participate in the vascular remodeling of maternal spiral arteries during pregnancy, and offers an attractive therapeutic target to prevent pathologic neovascularization as we found that CD160 is strongly expressed in the vasculature of a murine tumor.

Introduction

HLA-G is a human major histocompatibility class Ib gene characterized by a unique promoter region, limited polymorphism, restricted constitutive tissue distribution and the occurrence of several spliced transcripts encoding either membrane-bound or soluble proteins[1]. The actively secreted soluble HLA-G1 (sHLA-G1) isoform derives from mRNA retaining intron 4[2], which contains a stop codon that precludes translation of the transmembrane domain. This 37 kDa intron-retaining sHLA-G1 isoform associates with β2-microglobulin (β2m)[2]. The predominant expression of sHLA-G1 in the placenta at a time when polymorphic HLA-A and HLA-B class Ia molecules are repressed is consistent with important immunological functions during pregnancy[3]. sHLA-G1 induces apoptosis of activated CD8+ T and NK cells[4,5] and down-regulates CD4+ T cell allo-proliferation response[6]. The observation that some anti-HLA-G monoclonal antibodies (mAb) bound to placental endothelial cells[7,8] led to our hypothesis that HLA-G might also be involved in the modulation of placental angiogenesis and uterine vessel remodeling[7]. Several further observations are in line with such a novel function of HLA-G: first, a defect of HLA-G expression in extravillous cytotrophoblast is associated with preeclampsia[9,10], a common complication of pregnancy in which HLA-G+ endovascular trophoblast invasion of maternal spiral arteries is abrogated, compromising blood flow to the maternal interface[9]; second, it has been shown that HLA-G inhibited the transendothelial migration of NK cells[11] and the rolling adhesion of activated NK cells on endothelial cells[12]. To date, the potential role of sHLA-G1 in the modulation of angiogenesis has not been addressed.

Angiogenesis, the formation of new capillaries from pre-existing blood vessels, is a crucial component of embryonic vascular development and differentiation, wound healing, and organ regeneration, but it also contributes to the progression of pathologies that depends on neovascularization, including tumor growth, diabetes, ischemic ocular disease, and rheumatoid arthritis [13-15]. While the most important mediators of angiogenesis, the endothelial growth factor (VEGF) and the fibroblast growth factor (FGF) families are well defined[16], angiogenesis exists as a complex process involving multiple gene products expressed by different cell types, all contributing to an integrated sequence of events[17].

To test our hypothesis that sHLA-G1 is a regulator of endothelial cell activity, we investigated its in vitro effect. This study demonstrates that sHLA-G1 inhibits VEGF- and FGF-induced angiogenesis and induces apoptosis of endothelial cells by interaction with the glycosylphosphatidylinositol (GPI)-anchored CD160 receptor[18,19] expressed on endothelial cells. Interestingly, we show by immunohistochemistry performed ex vivo that CD160 is expressed at the vascular level in a mouse tumor model.

Figure 12:
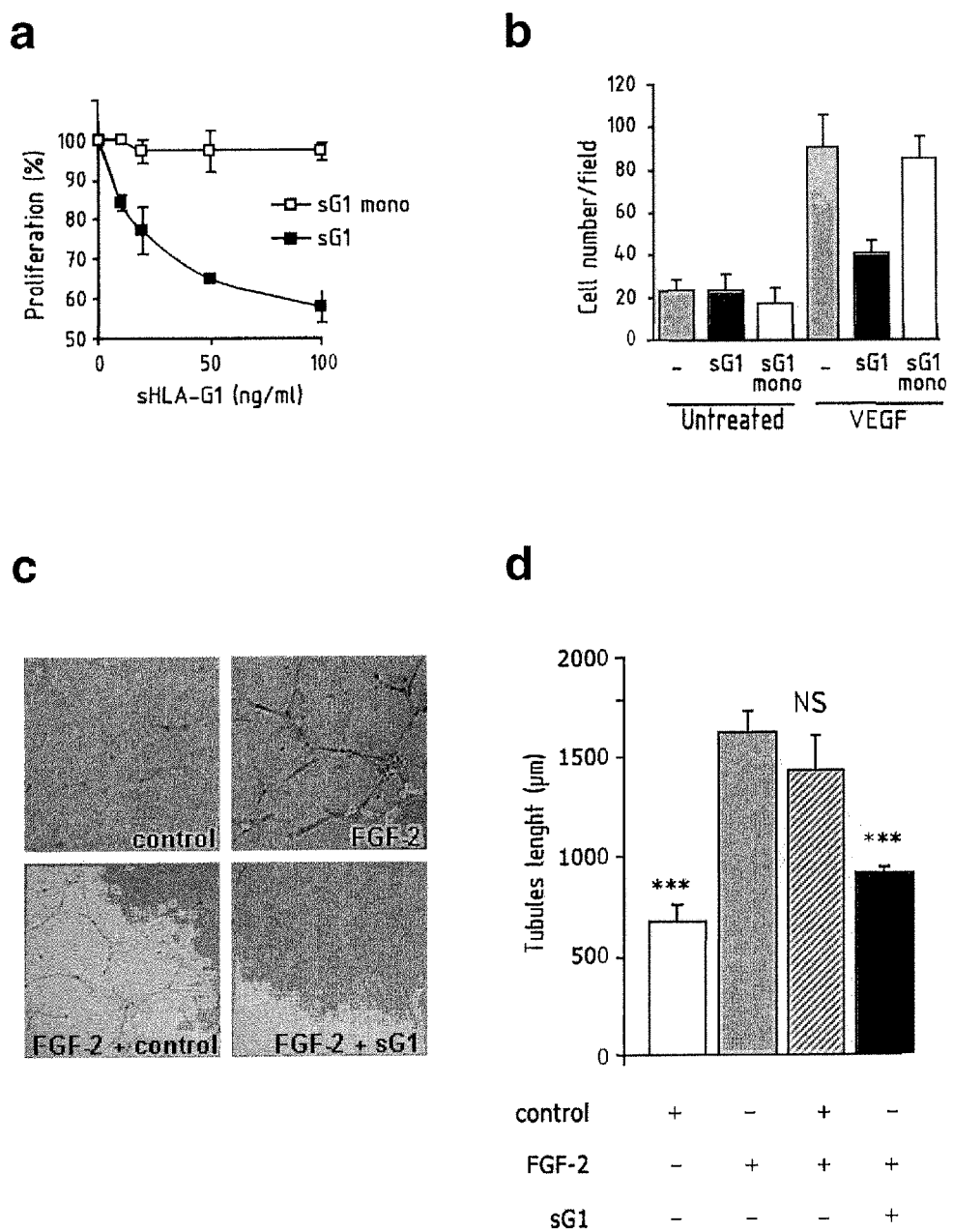

Results sHLA-G1 Inhibits VEGF- or FGF2-Mediated Endothelial Cell Proliferation, Migration and Capillary Tubule Formation VEGF is the most potent mitogenic and motogenic factor for endothelial cells[16]. Therefore, we investigated whether sHLA-G1 could interfere with VEGF functions in vitro. Purified recombinant sHLA-G1, when added exogenously to HUVEC, inhibited the proliferative response to VEGF in a dose-dependent manner (FIG. 12a). In contrast, the single chain protein sHLA-G1 fused to β2m (sHLA-G1mono) had no effect, indicating that folding of sHLA-G1 was critical for its biological activity. Moreover, sHLA-G1 also inhibited VEGF-mediated proliferation of bovine endothelial cells derived from aorta or adrenal gland microvessels (data not shown), suggesting a mechanism conserved among species and endothelial cells originating from different tissues.

We then examined the effect of sHLA-G1 on endothelial cell migration, using a migration assay. When HUVEC were incubated in the absence of VEGF, marginal, spontaneous migration occurred, whether or not sHLA-G1 was added (FIG. 12b, untreated). In contrast, after addition of VEGF, a significant increase in the number of migrated cells was detected. Under these conditions, addition of sHLA-G1 inhibited their migration (FIG. 12b, VEGF-treated). The inhibition of migration was not observed with sHLA-G1mono.

We next evaluated the capacity of sHLA-G1 to inhibit capillary tubule formation by endothelial cells cultured on Matrigel. sHLA-G1 significantly inhibited FGF-2-induced tube-like formation (FIG. 12c, morphology and FIG. 12d, quantification). Collectively, these findings indicate that sHLA-G1 inhibits in vitro pro-angiogenic factor-mediated endothelial cell proliferation, migration, and capillary tube formation.

sHLA-G1 Induces Apoptosis of Endothelial Cells

Figure 13:
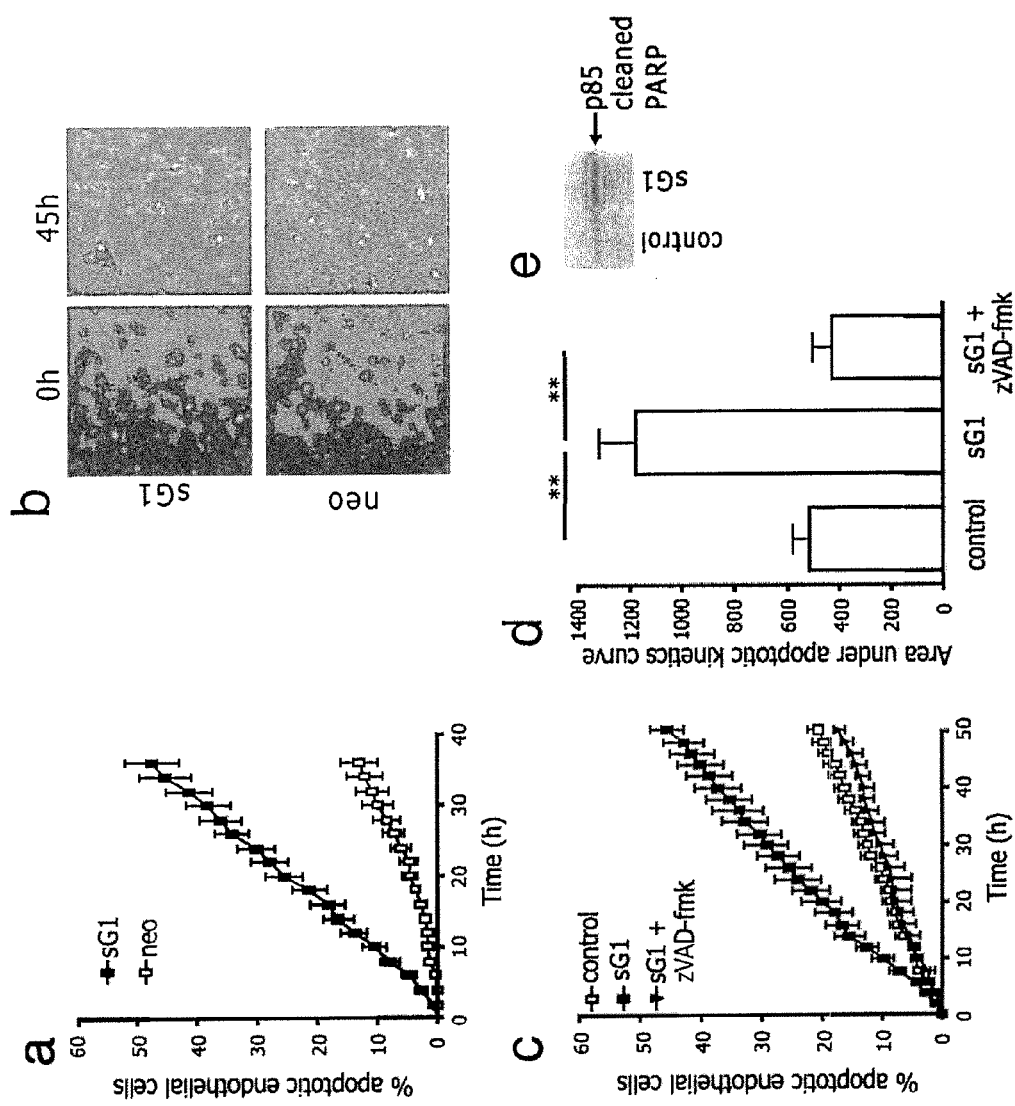

In order to determine the mechanisms involved in these sHLA-G1-induced inhibitory effects, we examined, using time lapse microscopy, whether apoptotic morphological changes occurred in endothelial cells after sHLA-G1 treatment. Using HUVEC-derived endothelial cells, we found that incubation of these cells with conditioned medium containing sHLA-G1 clearly induced apoptosis, as determined by time-lapse digital image microscopy (FIG. 13a, b). Images from the end of the experiment (FIG. 13b) and video data show that sHLA-G1-treated cell morphology is characterized by cytoplasmic and nuclear shrinkage and a change to a phase bright appearance, as well as the formation of membrane blebs/blisters. By comparison, incubation of these cells in control conditioned medium had no effect. Experiments in which recombinant sHLA-G1 (100 ng/ml) was used showed similar apoptotic effects (FIG. 13c,d). Use of the broad-spectrum caspase inhibitor zVAD-fmk prevented recombinant sHLA-G1-mediated apoptosis (FIG. 13c,d). Induction of apoptosis by sHLA-G1 was further demonstrated by the detection of cleaved poly (ADP-ribose) polymerase (PARP) by Western blot analysis (FIG. 13e).

sHLA-G1 Binds Directly to the CD160 Receptor

Next, it was important to identify the receptor involved in the sHLA-G1-mediated inhibitory effects on endothelial cells. We first tested whether sHLA-G1 interfered with VEGF receptors, by performing radioreceptor-assay binding experiments at 4° C. on HUVEC incubated for 2 hours (equilibrium time) with $^{125}$I-VEGF or $^{125}$I-sHLA-G1 in the presence of various concentrations of cold competitors. We first analyzed the binding of $^{125}$I-sHLA-G1 to HUVEC and found that cold VEGF or FGF-2 competitors had no effect, whereas unlabeled sHLA-G1 inhibited this binding as a function of the concentration with IC50 values in the nanomolar range (FIG. 14a). In competition experiments using $^{125}$I-VEGF as ligand, we found that cold VEGF rapidly displaced its binding to HUVEC with IC50 values in a nanomolar range, whereas sHLA-G1 had no effect (FIG. 14b). Furthermore, we found that cold sHLA-G1 competitor did not inhibit the binding of $^{125}$I-VEGF to PAEC-VEGF-R2 or PAEC-NPL1 transfectants (data not shown). However other inhibitors of VEGF-dependent proliferation and migration, such as dopamine[20], may act through internalization of VEGF receptors without competing with VEGF cell binding. Pre-incubation of HUVEC with VEGF at 37° C. almost totally abolished the binding of $^{125}$I-VEGF within 1 h, whereas that of sHLA-G1 up to 24 h had no effect on its binding (data not shown), thus demonstrating that it did not modulate the internalization or the expression of VEGF receptors. These results demonstrate that sHLA-G1 bound specifically to endothelial cells without interfering with VEGF receptors.

Then we investigated whether HUVEC expressed some of the HLA-G receptors described to date, including CD8[4], CD85d[21], CD85j[21], and CD160[22]. Flow cytometry analysis revealed that HUVEC were stained by anti-CD160 mAb, although not with constant levels, but not by anti-CD8, -CD85d nor -CD85j mAbs (FIG. 15a). Similarly, HMVEC also bound anti-CD160 mAb (FIG. 15a), as did bovine endothelial cells (data not shown), suggesting that the CD160 epitope recognized by the mAb was conserved among species. To further demonstrate that CD160 is expressed by HUVEC, we performed RT-PCR analysis on these cells by comparison to CD160$^+$ (NK cell line NK92) and CD160$^-$ (CD4$^+$ T) control cells, using CD160 specific primers. Similarly to NK92, CD160 mRNA was detected in HUVEC, whereas CD4$^+$ T cells were negative (FIG. 15b). Then HUVEC and NK92 cDNAs were isolated and sequenced. Predicted amino acid sequence alignment of HUVEC and NK92 CD160 proteins showed that they were both similar to the CD160 sequence already described[19], with the exception of two substituted residues indicating a possible allelic form (FIG. 15c).

To demonstrate that CD160 is also expressed on endothelial cells in vivo and that its expression could not result from culture conditions, we performed a specific immunohistochemical staining of a grafted Lewis lung carcinoma mouse tumor. We found that the anti-CD160 mAb strongly stained endothelial cells of micro vessels at the periphery of (FIG. 16a,b) and inside the tumor (FIG. 16c,d), whereas no staining was detected with IgG isotypic control (data not shown). In contrast, tumor cells remained unstained. Such reactivity of the CL1-R2 anti-CD160 mAb is not surprising as the previous identification and sequencing of both human and mouse CD160 encoding cDNA revealed a strong homology between the two species[19].

We then demonstrated that sHLA-G1 did effectively bind to the CD160 receptor expressed by endothelial cells. We first found that a HLA-G1 tetramer specifically bound to HUVEC like it did on CD160-transfected Jurkat (FIG. 17a). sHLA-G1-CD160 direct interaction on HUVEC was further demonstrated by showing that pre-incubation of HUVEC with recombinant sHLA-G1 specifically blocks the binding of anti-CD160 mAb (FIG. 17b), whereas a pre-incubation with VEGF did not (data not shown).

Figure 17:
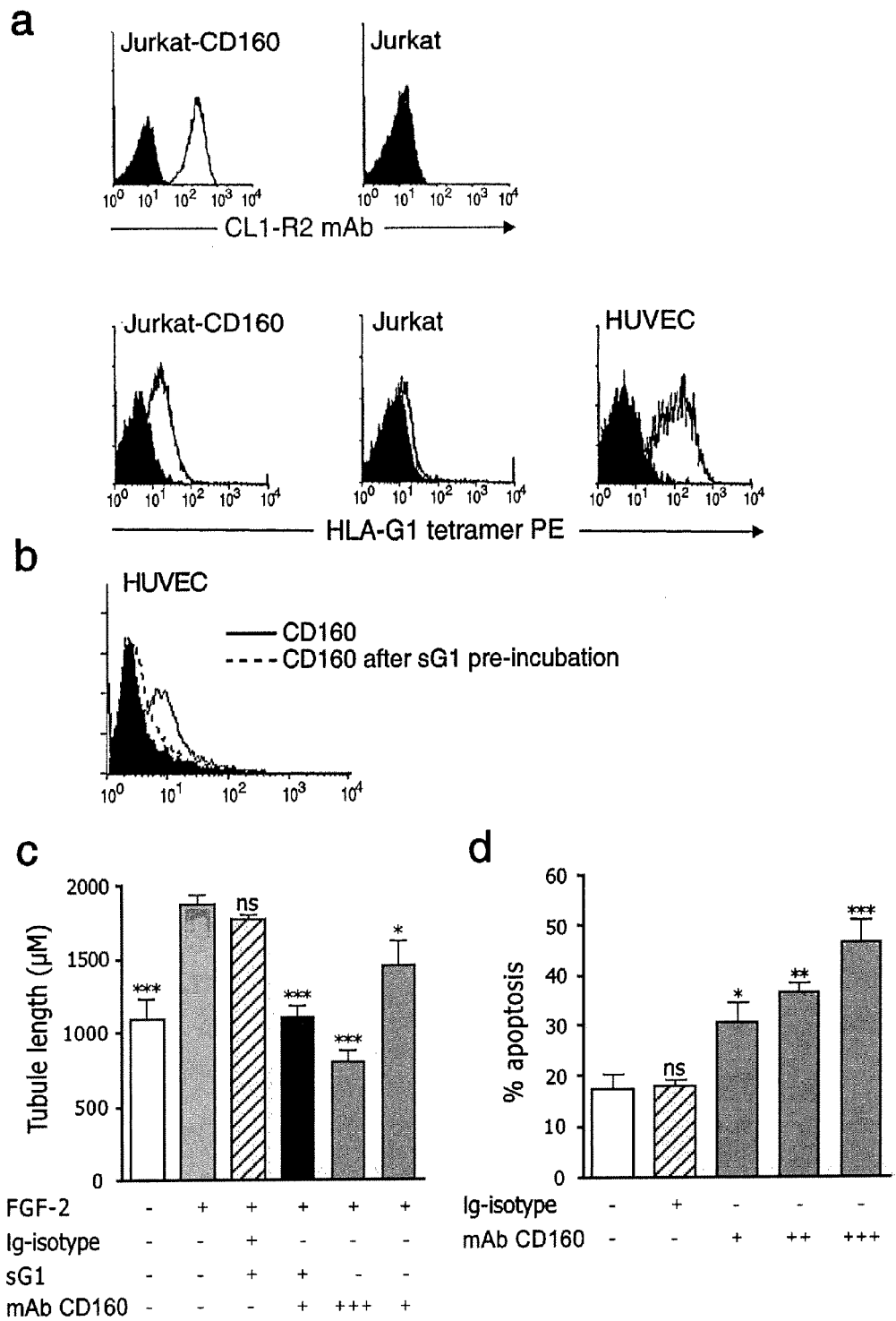

To further demonstrate that sHLA-G1 function is mediated through interaction with CD160, we tested whether soluble anti-CD160 mAb could mimic the sHLA-G1 anti-angiogenic activity in the in vitro Matrigel assay and the pro-apoptotic effect. The results clearly showed that addition of 1 to 10 µg/ml of purified CL1-R2 mAb led to the inhibition of FGF-2-mediated tubule vessel growth (FIG. 17c) and induction of endothelial apoptosis (FIG. 17d). These data further demonstrate that CD160 expressed by endothelial cells is a functional receptor able to trigger an anti-angiogenic cell response.

Discussion

In this study, we demonstrated that the sHLA-G1 molecule could exert a non immune function, namely angiogenesis inhibition. Spatial and temporal regulation of the vasculature at the maternal-fetal interface plays an important role in ensuring adequate blood supply to nourish the developing embryo, suggesting that there are locally acting factors that regulate vascular cells[23]. sHLA-G1 is secreted by extravillous trophoblast, including endovascular trophoblast[3] that replaces endothelial cells and remodels the maternal spiral arteries, thereby increasing the diameter of these vessels several fold[24]. We hypothesize that sHLA-G1 effects on endothelial cells might contribute to such replacement. Defects of HLA-G expression, including diminishment of soluble HLA-G in preeclamptic placentas, characterized by a shallow cytotrophoblast invasion and a reduced flow of maternal blood to the feto-placental unit[9,10], favors such hypothesis.

Different mechanisms have been reported to explain the activity of angiogenesis inhibitors, including induction of endothelial cell apoptosis[25], inhibition of matrix metalloproteinase activity[26], or chemorepulsion of endothelial cells[27]. In this report we demonstrate novel inhibitory actions of sHLA-G1, including significant blockade of endothelial cell migration, proliferation and vessel formation. In addition, we suggest that these effects may involve induction of endothelial cell apoptosis since sHLA-G1-treated endothelial cells progressively showed apoptotic morphology. Whether this apoptosis is mediated by endothelial FasL expression, like in activated CD8+ T cells[4], remains to be demonstrated. It is interesting that a role for apoptosis and Fas/FasL interactions in the remodeling of uterine arteries during pregnancy has recently been demonstrated[28].

The direct inhibitory effect of sHLA-G1 on vessel formation is most likely mediated through the functional CD160 receptor, as the CL1-R2 anti-CD160 mAb mimics the inhibition of FGF-2-induced capillary tubule formation by endothelial cells cultured in Matrigel and the induction of endothelial apoptosis. In contrast to other angiogenesis inhibitors like semaphorin 3F which is a competitor of VEGF binding to neuropilin receptor[27], sHLA-G1 acts directly on CD160 receptor. Knowing that various HLA class I molecules may bind to CD160[29], it cannot be excluded that other soluble MHC class I molecules could also trigger this receptor to exert anti-angiogenic functions. Collectively these findings provide important mechanistic insights into anti-angiogenic action of sHLA-G1. Further investigation is needed to determine the signaling pathways used by endothelial cells and NK cells following CD160 engagement and leading to apoptosis for the former and cytokine production[30] and cytotoxicity[29] for the latter.

In addition to the clear importance in the placental/uterine environment, the identification of CD160 as an inhibitory signaling receptor for angiogenesis could be useful for experimental anti-angiogenic therapy to prevent tumor cell growth. Our immunohistochemical analysis of a mouse graft tumor showed that CD160, encoded by a gene conserved in this species[31], was present in endothelial cells of the tumoral vasculature but was not expressed by tumor cells. Future goals are therefore to examine the potential CD160/sHLA-G1 mediated anti-angiogenic effect in different tumors and explore the possible therapeutic use of CD160 in the regulation of pathological neovascularization.

Methods

Cells and reagents. Human umbilical vein endothelial cells (HUVEC) and human microvascular endothelial cells (HM-VEC) (BioWhittaker, San Diego, Calif.) were maintained in EBM (BioWhittaker) supplemented with 5% FCS and 1 ng/ml VEGF or FGF-2 (R & D systems, Minneapolis, Ill.) every other day. SGHEC-7 cells are a HUVEC-derived cell line, cultured as previously described[32]. Porcine aortic endothelial cell (PAEC)-VEGF-R2 (KDR), PAEC-NPL1 transfectants, human Jurkat T cells and Jurkat transfected with CD160 (Jurkat-CD160)[29] were produced locally. NK92 is a human NK cell line expressing CD160[29]. CD4+ T cells were purified from PBMC using the MACS separation system (Miltenyi Biotec, Auburn, Calif.). Prostate adenocarcinoma PC3 cells transfected with PCDNA vector containing intron 4-retaining sHLA-G1 cDNA and PC3 cells transfected with empty vector (PC3-neo)[33] were grown to confluence for 4 days and conditioned media collected. Media was removed, centrifuged to remove cell debris and stored at −20° C. The sHLA-G1-β2m fusion monochain gene was engineered by connecting the last residue of the α3 domain of HLA-G to the first codon of the human β2m sequence through a 15-residue spacer[34]. sHLA-G1 and sHLA-G1mono were purified from eukaryotic cell culture supernatants, using immunoaffinity columns, as previously described[34]. VEGF 165 was expressed in a baculovirus system as described[35]. mAbs used included CL1-R2 (IgG1) anti-BY55/CD160[29], produced in one of our laboratories, anti-CD8 (OKT8, Coulter Immunotech), anti-ILT4/CD85d (gift of M. Colonna), anti-ILT2/CD85j, anti-CD106 (Beckton Dickinson), and dialyzed mouse IgG1 or IgG2a isotype controls (DAKO or Sigma). HLA-G1 tetramers were produced essentially as previously described[36], using synthetic self-peptide RIIPRHLQL[37] and after addition of streptavidin-PE (Pharmingen). Labeling of HUVEC, Jurkat and Jurkat-CD160 by PE-conjugated HLA-G tetramers was performed at 37° C. for 1 h. For Jurkat-CD160 and Jurkat, tetramers were cross-linked with anti-HLA class I W6/32 mAb, as previously described[22].

Endothelial cell proliferation and migration assays. For the proliferation analysis, HUVEC were seeded into 12-well plates (8,000 cells/well) coated with 0.3% gelatin in PBS. Cells were incubated with saline or VEGF (1 ng/ml) in the presence or absence of various concentrations of sHLA-G1 or sHLA-G1mono. Seven days later, cells were trypsinized and counted using a Coulter counter ZM. Migration assays were performed on growth arrested confluent HUVEC or BAEC. Cell monolayers were wounded with a rubber policeman, washed with serum-free medium and each well was photographed at 100× magnification. Dishes were then incubated for 16 h in serum free medium containing of sHLA-G1 or sHLA-G1mono (100 ng/ml) in the presence or not of VEGF (50 ng/ml). A second photograph of each well was taken and the cells which had migrated were counted by superposing the two photographs.

VEGF and sHLA-G1 cell binding. Purified recombinant VEGF and sHLA-G1 were radilabeled with $Na^{125}I$ to a specific activity of $2,4\times10^4$ and $1,1\times10^5$ cpm/ng, respectively[35]. Wells containing $2\times10^5$ serum-starved HUVEC were either pre-treated with 50 ng/ml of VEGF or sHLA-G1 at 37° C. for various time intervals (0.1-24 h) or processed immediately for binding assays. Briefly, dishes were rinsed in cold DMEM supplemented with 0.2% gelatin and 20 mM Hepes (pH 7.3) and incubated at 4° C. for 2 h with 2 ng/ml $^{125}I$-VEGF or $^{125}I$-sHLA-G1 in the absence or presence of indicated concentrations of cold competitors. Cells were then rinsed in the same medium, lysed in RIPA buffer and radioactivity counted in a γ counter.

In vitro capillary tube formation. Growth factor reduced Matrigel (BD Biosciences) was diluted in collagen (1/6 v/v) and kept on ice. 160 µl of this solution was added to each well of 8-well culture slides precoated with type I rat tail collagen and left at 37° C. for 1 h. A HUVEC suspension, mixed or not with control, FGF-2, sHLA-G1 or mAb CD160 was seeded into Matrigel/collagen gels for 24 h at 37° C. Microtubules were quantified by microscopy as previously described[38]. Briefly, the culture medium was removed, cells rinsed twice with PBS and fixed for 30 min at room temperature in a 4% PFA solution. Then, the cells were washed twice with PBS and stained with Masson's Trichrome. The extent of the microcapillary network was measured using an automated computer-assisted image analysis system (Imagenia, Biocom), and the total length of the capillaries in each well was determined. The mean microcapillary network length (µm) was calculated for each experimental condition. Experiments were performed in triplicate and repeated three times.

Flow cytometry analysis. Sub confluent HUVEC or HVMEC were scraped in PBS-EDTA and incubated in the presence or absence of 100 ng/ml of sHLA-G1 at 4° C. After 2 h, cells were incubated with anti-CD8, -CD85d, -CD85j, -CD106 or CL1-R2 anti-CD160 specific mAbs or Ig-isotype control (20 µg/ml) followed by $F(ab')_2$—FITC- or PE-conjugated anti-mouse IgG. Non-viable cells were excluded by the use of propidium iodide. Samples were analyzed on a Coulter-Epics ELITE flow cytometer.

RT-PCR and cDNA sequencing. CD160 transcripts were detected by RT-PCR using the following primers: 5'-TGCAGGATGCTGTTGGAACCC-3' (SEQ ID NO: 8) and 3'-TCAGCCTGAACTGAGAGTGCCTTC-5' (SEQ ID NO: 9). cDNA quality was confirmed by amplification of β-actin using the appropriate primers. Amplification conditions for CD160 and β-actin were 95° C. for 45 s, 60° C. 30 s, and 72° C. for 1 min. For CD160 sequencing, a Taq High Fidelity was used (Invitrogen). PCR product was purified (qiaex II, Qiagen) and analyzed with the following primers: BY01 (5'-TGCAGGATGCTGTTGGAACCC-3' (SEQ ID NO: 8)), BY03 (3'-TCAGCCTGAACTGAGAGTGCCTTC-5' (SEQ ID NO: 9)), BY02 (5'-CAGCTGAGACTTAAAAGGGATC-3' (SEQ ID NO: 5)) and BY04 (3'-CACCAACACCATC-TATCCCAG-5' (SEQ ID NO: 6)).

Immunohistochemistry. Sub-confluent Lewis lung carcinoma cells were trypsinized, washed twice and suspended in PBS. $2\times10^5$ cells were injected subcutaneously into the dorsal midback region of C57BL/6 female mice (IFFA Credo, France). Tumors were taken on day 21, fixed with 10% formalin (Sigma) overnight at 4° C., and embedded in paraffin (Embeder Leica). 5 µm sections were placed in a Dako Autostainer and incubated with TNB blocking buffer (TSA kit, NEN), peroxidase-blocking reagent (DAKO) and mouse immunoglobulin blocking reagent (Vector Laboratories). Sections were incubated with CL1-R2 anti-CD160 mAb (10 µg/ml), followed by biotin-labeled goat anti-mouse IgG and avidin-biotin complex (Vector Laboratories). They were stained with DAB (Vector Laboratories), counterstained with hematoxylin, viewed on a Nikon microscope (E-800) and digitized using a DMX 1200 camera (Nikon) with 40× objective.

Time-lapse microscopy. SGHEC-7 cells were seeded into 6-well plates ($2.5\times10^5$ cells/well in normal culture medium. After 15 h, conditioned media from PC3-sG1 or PC3-neo cells, recombinant sHLA-G1 (100 ng/ml), CL1-R2 anti-CD160 mAb (1-10 µg/ml), IgG1 isotype control (10 µg/ml) or zVAD-fmk (50 µmol/l, Calbiochem) were added to the wells. The plate was transferred to an Olympus IX70 inverted fluorescence microscope with motorized stage and cooled CCD camera and enclosed in a heated, humidified chamber at 37° C. with 5% $CO_2$ in air. Images were taken every 15 min for 36-50 h and time-lapse sequences were analyzed using ImagePro Plus (Media Cybernetics). In each field of view 40 cells were randomly chosen. The experiments were repeated at least four times. Apoptotic cells were scored according to the time at which clear apoptotic morphology was first observed[39].

Western blot analysis of cleaved PARP expression. SGHEC-7 endothelial cells were seeded in culture plates. After 16 h the cells were stimulated with recombinant sHLA-G1 (100 ng/ml) for 60 h. Cells were lysed in RIPA buffer with 0.1 mg/ml PMSF, 30 µl/ml aprotinin, and 1 mmol/l sodium orthovanadate at 4° C. for 30 min. The samples were separated by SDS-PAGE and transferred to a nitrocellulose membrane. Following incubation in blocking buffer for 1 h at room temperature, the membrane was incubated with rabbit polyclonal anti-human cleaved PARP (Promega) for 1 h. Anti-rabbit IgG peroxidase (A6154, Sigma) was added for 1 h. Detection of membrane bound antibodies was carried out by chemiluminescence (ECLPlus, Amersham).

Statistical analysis. Results are expressed as mean±SEM or SD of "n" independent experiments and assessed using the Mann Whitney U test or ANOVA test as appropriate and Everstat or GraphPadPrism software with $P<0.05$ considered statistically significant.

1. Le Bouteiller, P. & Blaschitz, A. The functionality of HLA-G is emerging. Immunol. Rev. 167, 233-244 (1999).
2. Ishitani, A. & Geraghty, D. E. Alternative splicing of HLA-G transcripts yields proteins with primary structures resembling both class I and class II antigens. Proc. Natl. Acad. Sci. USA 89, 3947-3951 (1992).
3. Morales, P. J. et al. Placental cell expression of HLA-G2 isoforms is limited to the invasive trophoblast phenotype. J. Immunol. 171, 6215-6224 (2003).
4. Fournel, S. et al. Cutting Edge: Soluble HLA-G1 triggers CD95/CD95 ligand-mediated apoptosis in activated CD8+ cells by interacting with CD8. J. Immunol. 164, 6100-6104 (2000).
5. Contini, P. et al. Soluble HLA-A, -B, -C and -G molecules induce apoptosis in T and NK CD8+ cells and inhibit cytotoxic T cell activity through CD8 ligation. Eur. J. Immunol. 33, 125-134 (2003).
6. Lila, N., Rouas-Freiss, N., Dausset, J., Carpentier, A. & Carosella, E. D. Soluble HLA-G protein secreted by allo-specific CD4+ T cells suppresses the allo-proliferative response: A CD4+ T cell regulatory mechanism. Proc. Natl. Acad. Sci. USA 98, 12150-12155 (2001).
7. Blaschitz, A. et al. Endothelial cells in chorionic fetal vessels of first trimester placenta express HLA-G. Eur. J. Immunol. 27, 3380-3388 (1997).

8. Dye, J. F. et al. Phenotype of the Endothelium in the Human Term Placenta. Placenta 22, 32-43 (2001).
9. Lim, K. H. et al. Human cytotrophoblast differentiation/invasion is abnormal in pre-eclampsia. Am. J. Pathol. 151, 1809-1818 (1997).
10. Yie, S. M., Li, L. H., Li, Y. M. & Librach, C. HLA-G protein concentrations in maternal serum and placental tissue are decreased in preeclampsia. Am. J. Obstet. Gynecol. 191, 525-529 (2004).
11. Dorling, A., Monk, N. & Lechler, R. HLA-G inhibits the transendothelial migration of human NK cells. Eur. J. Immunol. 30, 586-593 (2000).
12. Forte, P. et al. HLA-G Inhibits Rolling Adhesion of Activated Human NK Cells on Porcine Endothelial Cells. J. Immunol. 167, 6002-6008 (2001).
13. Risau, W. Mechanisms of angiogenesis. Nature 386, 671-674 (1997).
14. Carmeliet, P. Angiogenesis in health and disease. Nat. Med. 9, 653-660 (2003).
15. Folkman, J. Angiogenesis in cancer, vascular, rheumatoid and other disease. Nat. Med. 1, 27-31 (1995).
16. Ferrara, N., Gerber, H. P. & LeCouter, J. The biology of VEGF and its receptors. Nat. Med. 9, 669-76. (2003).
17. Ferrara, N. Vascular endothelial growth factor and the regulation of angiogenesis. Recent Prog. Horm. Res. 55, 15-35; discussion 35-36 (2000).
18. Maiza, H. et al. A novel 80-kD cell surface structure identifies human circulating lymphocytes with natural killer activity. J. Exp. Med. 178, 1121-1126 (1993).
19. Anumantha, A. et al. Cloning of BY55, a novel Ig superfamily member expressed on NK cells, CTL, and intestinal intraepithelial lymphocytes. J. Immunol. 161, 2780-2790 (1998).
20. Basu, S. et al. The neurotransmitter dopamine inhibits angiogenesis induced by vascular permeability factor/vascular endothelial growth factor. Nat. Med. 7, 569-574 (2001).
21. Shiroishi, M. et al. Human inhibitory receptors Ig-like transcript 2 (ILT2) and ILT4 compete with CD8 for MHC class I binding and bind preferentially to HLA-G. Proc. Natl. Acad. Sci. USA 100, 8856-8861 (2003).
22. Agrawal, S. et al. Cutting edge: MHC class I triggering by a novel cell surface ligand costimulates proliferation of activated human T cells. J. Immunol. 162, 1223-1226 (1999).
23. Ong, S., Lash, G. & Baker, P. N. Angiogenesis and placental growth in normal and compromised pregnancies. Baillieres Best Pract. Res. Clin. Obst. Gynaecol. 14, 969-980 (2000).
24. Loke, Y. & King, A. Immunology of implantation. Baillière's Clin. Obst. Gynaecol. 14, 827-837 (2000).
25. Folkman, J. Angiogenesis and apoptosis. Sem. Cancer Biol. 13, 159-167 (2003).
26. Kim, Y. M. et al. Endostatin inhibits endothelial and tumor cellular invasion by blocking the activation and catalytic activity of matrix metalloproteinase. Cancer Res 60, 5410-5453 (2000).
27. Bielenberg, D. R. et al. Semaphorin 3F, a chemorepulsant for endothelial cells, induces a poorly vascularized, encapsulated, nonmetastatic tumor phenotype. J. Clin. Invest. 114, 1260-1271 (2004).
28. Ashton, S. et al. Uterine spiral artery remodeling involves endothelial apoptosis induced by extravillous trophoblast through Fas/FasL interactions. Arterioscler. Thromb. Vasc. Biol. 25, 102-108 (2005).
29. Le Bouteiller, P. et al. Engagement of CD160 receptor by HLA-C is a triggering mechanism used by circulating natural killer (NK) cells to mediate cytotoxicity. Proc. Natl. Acad. Sci. USA 99, 16963-16968 (2002).
30. Barakonyi, A. et al. Cutting Edge: Engagement of CD160 by its HLA-C physiological ligand triggers a unique cytokine profile secretion in the cytotoxic peripheral blood NK cell subset. J. Immunol. 173, 5349-5354 (2004).
31. Bensussan, A. BY55 (CD160). Protein Review Web 1, 72-73 (2000).
32. Cartwright, J. E., Whitley, G. S. & Johnstone, A. P. The expression and release of adhesion molecules by human endothelial cell lines and their consequent binding of lymphocytes. Exp. Cell. Res. 217, 329-335 (1995).
33. Solier, C. et al. Secretion of pro-apoptotic intron 4-retaining soluble HLA-G1 by human villous trophoblast. Eur. J. Immunol. 32, 3576-3586 (2002).
34. Fournel, S. et al. Soluble HLA-G: purification from eucaryotic transfected cells and detection by a specific ELISA. Am. J. Reprod. Immunol. 42, 22-29 (1999).
35. Plouët, J. et al. Extracellular cleavage of the vascular endothelial growth factor 189-amino acid form by urokinase is required for its mitogenic effect. J. Biol. Chem. 272, 13390-13396 (1997).
36. Allan, D. S. et al. Tetrameric complexes of human histocompatibility leukocyte antigen (HLA)-G bind to peripheral blood myelomonocytic cells. J. Exp. Med. 189, 1149-1156 (1999).
37. Lee, N. et al. The membrane-bound and soluble forms of HLA-G bind identical sets of endogenous peptides but differ with respect to TAP association. Immunity 3, 591-600 (1995).
38. Ruggeri, B. et al. CEP-7055: a novel, orally active pan inhibitor of vascular endothelial growth factor receptor tyrosine kinases with potent antiangiogenic activity and antitumor efficacy in preclinical models. Cancer Res. 63, 5978-5991 (2003).
39. Dash, P. R., Cartwright, J. E., Baker, P. N., Johnstone, A. P. & Whitley, G. S. Nitric oxide protects human extravillous trophoblast cells from apoptosis by a cyclic GMP-dependent mechanism and independently of caspase 3 nitrosylation. Exp. Cell. Res. 287, 314-324 (2003).

The invention claimed is:

1. A method for inhibiting angiogenesis comprising administering to a subject a soluble, non-aggregated anti-CD160 compound selected from the group consisting of anti-CD160 antibody, anti-CD160 antibody fragment, and anti-CD160 antibody derivative, wherein said CD160 antibody derivative comprises all 6 CDRs of the anti-CD160 mAb CL1-R2.

2. The method of claim 1, wherein the anti-CD160 compound is administered in a pharmaceutical composition.

3. The method of claim 1, wherein the anti-CD160 compound is anti-CD160 mAb CL1-R2.

4. The method of claim 1, wherein administering the anti-CD160 compound has an anti-angiogenic effect.

5. The method of claim 4, wherein the anti-angiogenic effect is the inhibition of blood vessel formation and growth.

6. The method of claim 1, wherein administering the anti-CD160 compound does not induce apoptosis of T cells.

7. The method of claim 1, wherein the anti-CD160 compound is capable of competing with the anti-CD160 mAb CL1-R2 for binding to CD160.

8. The method of claim 1, wherein the anti-CD160 compound does not bind to CD8αβ.

9. The method of claim 1, wherein the anti-CD160 compound does not bind to CD85j.

10. A method of treating a neo-vascularization-favored pathology selected from the group consisting of tumor growth, pre-eclampsia, eclampsia, diabetes, ischemic ocular disease, and rheumatoid arthritis by administering to a subject a soluble, non-aggregated anti-CD160 compound selected from the group consisting of anti-CD160 antibody, anti-CD160 antibody fragment, and anti-CD160 antibody derivative, said anti-CD160 compound having an anti-angiogenic effect of inhibiting blood vessel formation and growth, thereby relieving the subject of one or more symptoms associated with the pathology.

11. The method of claim 10, wherein the pathology is tumor growth.

* * * * *

UNITED STATES PATENT AND TRADEMARK OFFICE
CERTIFICATE OF CORRECTION

Page 1 of 1

PATENT NO. : 8,444,978 B2
APPLICATION NO. : 13/175221
DATED : May 21, 2013
INVENTOR(S) : Armand Bensussan et al.

It is certified that error appears in the above-identified patent and that said Letters Patent is hereby corrected as shown below:

In the Claims:

Claim 1 at column 49, lines 22 to 28, should read:

1. A method for inhibiting angiogenesis comprising administering to a subject a soluble, non-aggregated anti-CD160 compound selected from the group consisting of anti-CD160 antibody, anti-CD160 antibody fragment, and anti-CD160 antibody derivative, wherein said anti-CD160 antibody derivative comprises all 6 CDRs of the anti-CD160 mAb CL1-R2, said CL1-R2 being obtainable from the hybridoma deposited as CNCM deposit number I-3204.

Claim 10 at column 50, lines 26 to 36, should read:

10. A method of treating a neo-vascularization-favored pathology selected from the group consisting of tumor growth, pre-eclampsia, eclampsia, diabetes, ischemic ocular disease, and rheumatoid arthritis by administering to a subject a soluble, non-aggregated anti-CD160 compound selected from the group consisting of anti-CD160 antibody, anti-CD160 antibody fragment, and anti-CD160 antibody derivative, wherein said anti-CD160 antibody derivative comprises all 6 CDRs of the anti-CD160 mAb CL1-R2, said CL1-R2 being obtainable from the hybridoma deposited as CNCM deposit number I-3204, said anti-CD160 compound having an anti-angiogenic effect of inhibiting blood vessel formation and growth, thereby relieving the subject of one or more symptoms associated with the pathology.

Signed and Sealed this
Seventeenth Day of September, 2013

Teresa Stanek Rea
*Deputy Director of the United States Patent and Trademark Office*

SEQUENCE LISTING

<160> NUMBER OF SEQ ID NOS: 9

<210> SEQ ID NO 1
<211> LENGTH: 21
<212> TYPE: DNA
<213> ORGANISM: Artificial sequence
<220> FEATURE:
<223> OTHER INFORMATION: primer

```
<400> SEQUENCE: 1
tgcaggatgc tgttggaacc c                                              21

<210> SEQ ID NO 2
<211> LENGTH: 24
<212> TYPE: DNA
<213> ORGANISM: Artificial sequence
<220> FEATURE:
<223> OTHER INFORMATION: primer

<400> SEQUENCE: 2
cttccgtgag agtcaagtcc gact                                           24

<210> SEQ ID NO 3
<211> LENGTH: 24
<212> TYPE: DNA
<213> ORGANISM: Artificial sequence
<220> FEATURE:
<223> OTHER INFORMATION: primer

<400> SEQUENCE: 3
gcgggaaatc gtgcgtgcgt gaca                                           24

<210> SEQ ID NO 4
<211> LENGTH: 24
<212> TYPE: DNA
<213> ORGANISM: Artificial sequence
<220> FEATURE:
<223> OTHER INFORMATION: primer

<400> SEQUENCE: 4
gtgctttgat ggaagttgag gtag                                           24

<210> SEQ ID NO 5
<211> LENGTH: 22
<212> TYPE: DNA
<213> ORGANISM: Artificial sequence
<220> FEATURE:
<223> OTHER INFORMATION: primer

<400> SEQUENCE: 5
cagctgagac ttaaaaggga tc                                             22

<210> SEQ ID NO 6
<211> LENGTH: 21
<212> TYPE: DNA
<213> ORGANISM: Artificial sequence
<220> FEATURE:
<223> OTHER INFORMATION: primer

<400> SEQUENCE: 6
gaccctatct accacaacca c                                              21

<210> SEQ ID NO 7
<211> LENGTH: 9
<212> TYPE: PRT
<213> ORGANISM: Artificial sequence
<220> FEATURE:
<223> OTHER INFORMATION: tetramer linker

<400> SEQUENCE: 7

Arg Ile Ile Pro Arg His Leu Gln Leu
1               5

<210> SEQ ID NO 8
<211> LENGTH: 21
```

```
<212> TYPE: DNA
<213> ORGANISM: Artificial sequence
<220> FEATURE:
<223> OTHER INFORMATION: primer

<400> SEQUENCE: 8
tgcaggatgc tgttggaacc c                                              21

<210> SEQ ID NO 9
<211> LENGTH: 24
<212> TYPE: DNA
<213> ORGANISM: Artificial sequence
<220> FEATURE:
<223> OTHER INFORMATION: primer

<400> SEQUENCE: 9
cttccgtgag agtcaagtcc gact                                           24
```